US012569132B2

(12) United States Patent
Kapoula

(10) Patent No.: US 12,569,132 B2
(45) Date of Patent: Mar. 10, 2026

(54) ANALYSIS OF EYE MOVEMENTS IN 3D REAL SPACE IN DIRECTION AND DEPTH

(71) Applicants: CENTRE NATIONAL DE LA RECHERCHE SCIENTIFIQUE (CNRS), Paris (FR); UNIVERSITE PARIS CITE, Paris (FR)

(72) Inventor: Zoi Kapoula, Paris (FR)

(73) Assignees: CENTRE NATIONAL DE LA RECHERCHE SCIENTIFIQUE (CNRS), Paris (FR); UNIVERSITE PARIS CITE, Paris (FR)

( * ) Notice: Subject to any disclaimer, the term of this patent is extended or adjusted under 35 U.S.C. 154(b) by 558 days.

(21) Appl. No.: 17/925,241

(22) PCT Filed: May 7, 2021

(86) PCT No.: PCT/EP2021/062224
§ 371 (c)(1),
(2) Date: Nov. 14, 2022

(87) PCT Pub. No.: WO2021/228724
PCT Pub. Date: Nov. 18, 2021

(65) Prior Publication Data
US 2023/0225611 A1      Jul. 20, 2023

(30) Foreign Application Priority Data

May 14, 2020      (FR) ........................................ 2004768
Oct. 7, 2020      (EP) ...................................... 20306166

(51) Int. Cl.
*A61B 3/113*      (2006.01)
*A61B 3/08*      (2006.01)
*A61B 5/16*      (2006.01)

(52) U.S. Cl.
CPC ................ *A61B 3/113* (2013.01); *A61B 3/08* (2013.01); *A61B 5/163* (2017.08)

(58) Field of Classification Search
CPC ............ A61B 3/113; A61B 3/08; A61B 5/163
(Continued)

(56) References Cited

U.S. PATENT DOCUMENTS

2006/0195076 A1*   8/2006   Blumenkranz ...... A61B 90/361
                                                606/4
2011/0299034 A1*   12/2011   Walsh .................... A61B 3/132
                                                351/206

(Continued)

FOREIGN PATENT DOCUMENTS

FR            2 953 711 B1      2/2012
WO      WO 2015/120438 A1      8/2015

OTHER PUBLICATIONS

English translation of the International Search Report and Written Opinion of the International Searching Authority for International Application No. PCT/EP2021/062224, dated Jul. 28, 2021.
(Continued)

*Primary Examiner* — Mohammed A Hasan
(74) *Attorney, Agent, or Firm* — Birch, Stewart, Kolasch & Birch, LLP

(57) ABSTRACT

The invention relates to a method of processing data representative of a person's binocular motricity, the method comprising the following steps: —stimulating the binocular motricity of a person by means of a binocular motricity stimulation device (21) configured to specifically stimulate saccades, vergences or a combination of both or of a reading test (22); physical stimuli in 3D real space seen with both eyes naturally (without artifices); acquiring the movement of the right eye (RE) and left eye (LE) of a person (P) during said stimulation and, if applicable, a stimulation signal from the binocular motor stimulation device; the method com-
(Continued)

prising the following steps implemented in a processing unit (3); determination from the movement of the left eye (LE) and the right eye (RE), of an effective trajectory (Tr1) of the eyes in response to each stimulation, an effective trajectory corresponding to a saccade and/or a vergence movement of the eyes.

22 Claims, 31 Drawing Sheets

(58) Field of Classification Search
USPC .......................................................... 351/209
See application file for complete search history.

(56) References Cited

U.S. PATENT DOCUMENTS

| 2012/0320336 A1 | 12/2012 | Kapoula et al. | |
|---|---|---|---|
| 2016/0262608 A1* | 9/2016 | Krueger | G16H 40/63 |
| 2018/0008141 A1* | 1/2018 | Krueger | A61B 5/7257 |
| 2018/0029513 A1 | 2/2018 | Jergenson et al. | |
| 2019/0029513 A1* | 1/2019 | Gunnerson | A61B 3/113 |
| 2019/0192063 A1* | 6/2019 | Samadani | A61B 3/0091 |

OTHER PUBLICATIONS

French Search Report for French Application No. 2004768, dated Jan. 20, 2021.

* cited by examiner

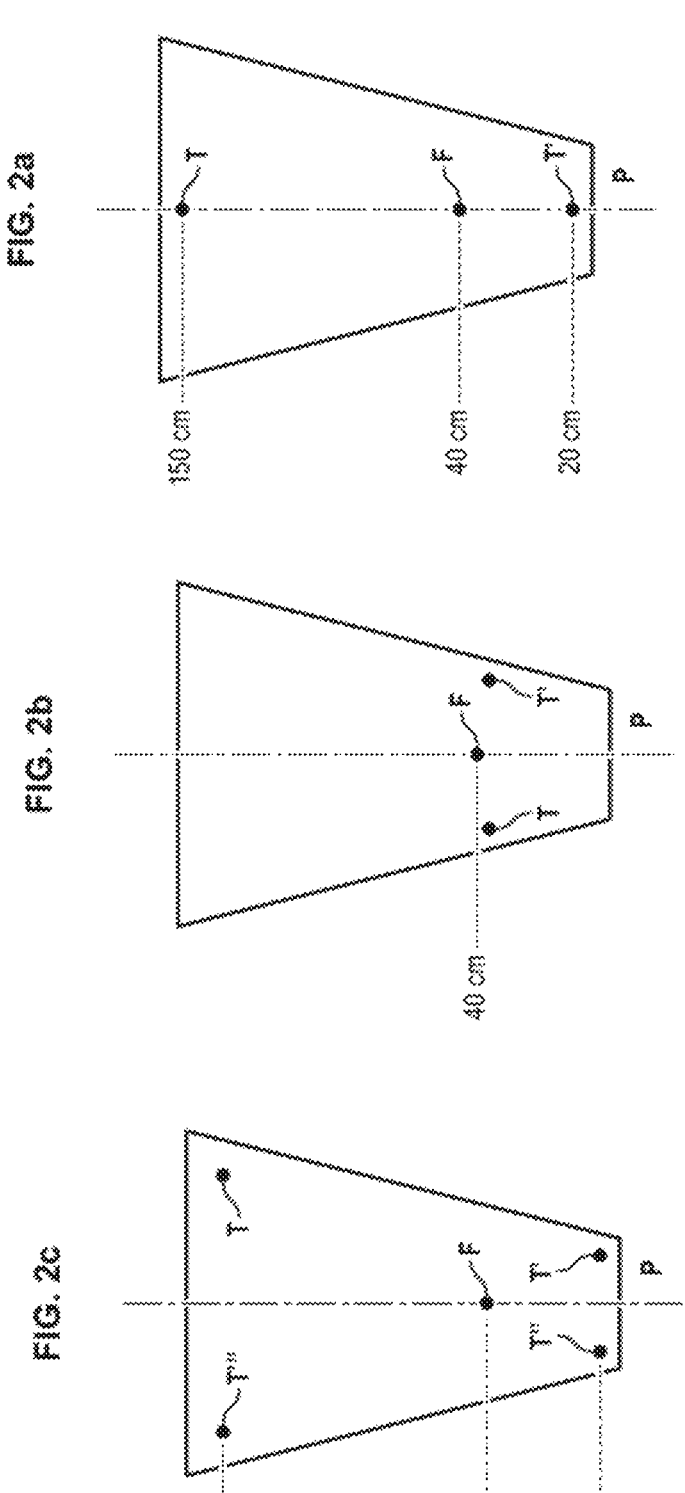

FIG. 2d

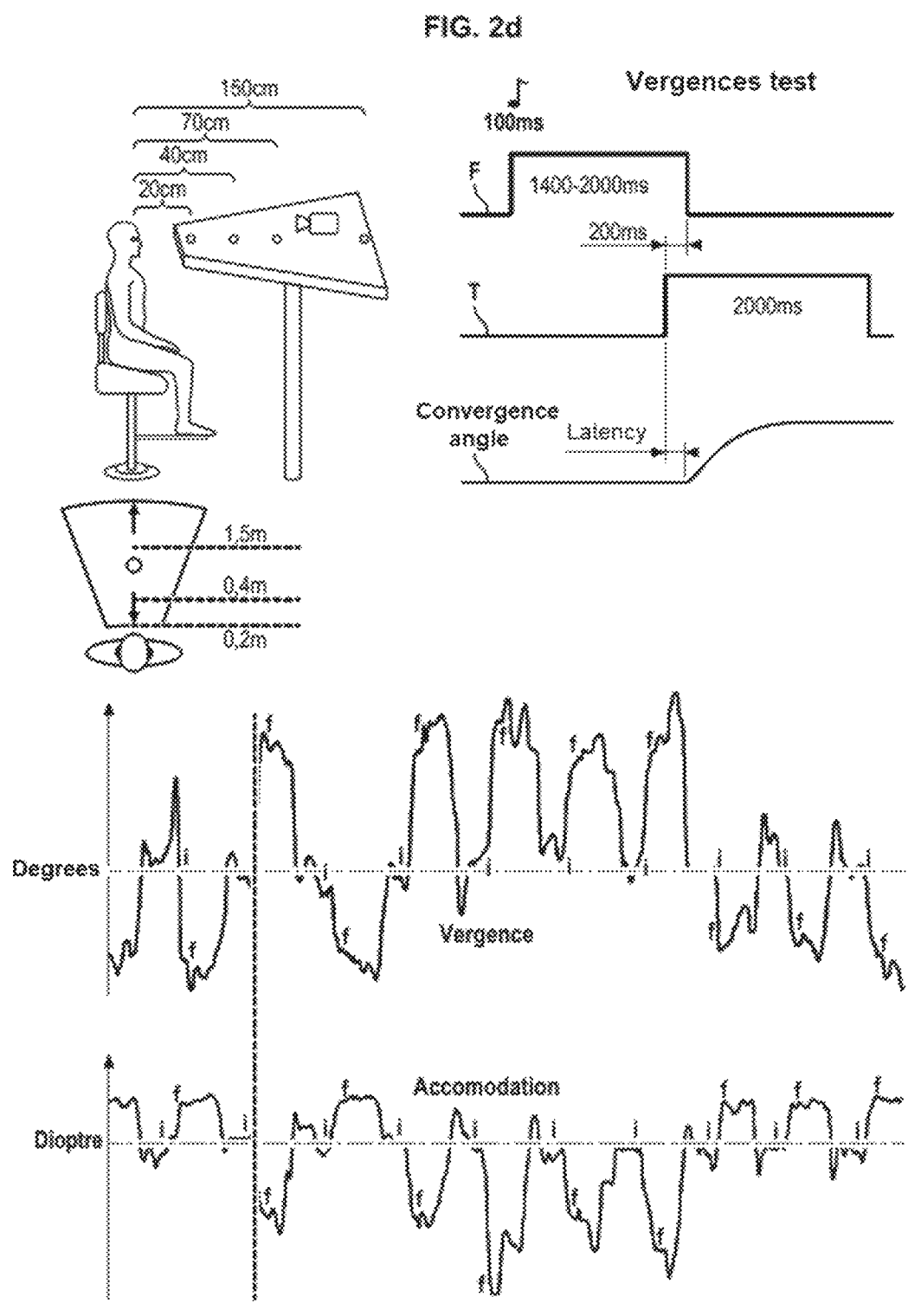

Vergences test

150cm
70cm
40cm
20cm

100ms
F
1400-2000ms
200ms
T
2000ms

Convergence
angle     Latency 1,5m
0,4m
0,2m

Degrees

Vergence

Dioptra

Accomodation

16-YEARS OLD DYSLEXIC INDIVIDUAL

D          Image analysis test

19-YEARS OLD DYSPRAXIC INDIVIDUAL

FIG. 15B and 15C

19-YEARS OLD DYSPRAXIC INDIVIDUAL

19-YEARS OLD DYSPRAXIC INDIVIDUAL

D    Image analysis test

12-YEARS OLD DYSPHASIC INDIVIDUAL

12-YEARS OLD DYSPHASIC INDIVIDUAL

D      Image analysis test p<0.05 (p= 0.041)

Wilcoxon test p<0.05 (p= 0.0125)

Wilcoxon test p<0.01 (p= 0.0069)

Wilcoxon test

4. Mean acceleration ML ~ HYPER *

FIG. 22

ANALYSIS OF EYE MOVEMENTS IN 3D REAL SPACE IN DIRECTION AND DEPTH

TECHNICAL FIELD OF THE INVENTION

The invention concerns the field of processing data representative of the binocular motricity of a person, the binocular motricity having been stimulated by means of a visual test, for example by means of a device dedicated to the stimulation of the binocular motricity or by means of a reading test. And the invention applies in particular to the diagnosis of pathologies related to binocular motricity, in particular learning disorders such as dyslexia or vertigo. It also applies to research on development or normal aging, and finally, to applications in work ergonomics, and to reading or exploring texts or images.

BACKGROUND ART

Binocular tests, and in particular those for testing binocular motricity, are often used to detect various neurological pathologies.

Indeed, binocular motor disorders can reflect different binocular pathologies but mainly neurological pathologies.

Therefore, there is a need for binocular motor testing modalities to be able to detect neurological pathologies efficiently, i.e. that are as little as possible subjective and practitioner-dependent.

SUMMARY OF THE INVENTION

The invention responds to this need.

To this end, the invention provides a method for processing data representative of a person's binocular motor skills, the method comprising the following steps:

stimulating the binocular motor skills of a person by means of a binocular motor skills stimulation device configured to specifically stimulate saccades, vergences or a combination of both or of a text or image reading test:

acquiring the movement of a person's right eye and left eye during said stimulation and, if applicable, a stimulation signal from the binocular motor stimulation device; the method comprising the following steps carried out in a processing unit;

determining from the movement of the left eye and the right eye an actual trajectory of the eyes in response to each stimulation, an effective trajectory corresponding to a saccade and/or a vergence movement of the eyes;

determining a representative (also referred to as "theoretical") eye trajectory for each stimulation;

comparing each effective trajectory with the corresponding representative trajectory so as to eliminate the erroneous effective trajectories furthest from the representative trajectory and thus obtain selected trajectories for each stimulation;

treating each selected trajectory so as to obtain saccade and/or vergence parameters, the parameters being characteristic of a possible pathology of a person in particular learning disorders such as dyslexia or vertigo.

The method according to the invention is advantageously complemented by the following characteristics, taken alone or in any of their technically possible combinations:

the determination consists in treating all the effective trajectories for a given stimulation so as to obtain a trajectory representative of this stimulation;

the method comprises a step of displaying an image of the stimulation device on which the trajectories of eye movement are represented;

the effective trajectory corresponding to a saccade is obtained by calculating a conjugate signal defined by the average of the position of the left eye with the position of the right eye;

the effective trajectory corresponding to a vergence is obtained by calculating a non-conjugated signal defined by the difference of the position of the left eye with the position of the right eye;

the movement of the right eye and the left eye are acquired with targets presented in 3D real space, the method comprising a step of transforming the movement of the right eye and the left eye into degrees;

a saccade parameter is the peak velocity of the saccade, or the average velocity;

a saccade parameter is the amplitude of a saccade, the amplitude being defined between the onset of the saccade and the offset of the saccade, the onset of the saccade being defined by the instant at which the saccade has a velocity of x % of the peak velocity of the saccade, the offset of the saccade being defined by the instant after peak velocity at which the saccade has a velocity of x % of the peak velocity, x being between 5 and 15°;

The visual or audiovisual saccade test consists of subjecting the person to a first visual or audiovisual stimulus and then subjecting him/her to a second visual or audiovisual stimulus located at a different place from the first visual or audiovisual stimulus (on the left or on the right of the first place, on the same isovergence arc), a saccade parameter being a latency defined by the time between the moment of activation of the second visual stimulus and the onset of the trajectory of the eyes to pass from the first visual or audiovisual stimulus to the second visual or audiovisual stimulus; these stimuli are physical, presented in real space, and seen by the person naturally with both eyes (without the known artifices, e.g. stereovision glasses, virtual reality 3D screens, or any other process creating artificial depth vision);

a saccade parameter is the duration of the saccade defined by the time between the offset of the eye movement and the onset of the eye movement;

a saccade parameter is the amplitude of the difference between the two eyes between the onset of the saccade and the offset of the saccade;

a saccade parameter is one of the dis-conjugation parameters: obtained on the basis of the signal of the difference between the position of the left eye and the right eye during a saccade test;

a dis-conjugation parameter, is one of the following parameters:

amplitude of the dis-conjugation expressed in degrees of the defined saccade: amplitude of the difference between the two eyes between the onset and the offset of the saccade;

drift 1 expressed in degrees: amplitude of the dis-conjugation between the offset of the saccade and up to 80 ms after the offset of the saccade;

drift 2 expressed in degrees: amplitude of the dis-conjugation between the offset of the saccade and up to 160 ms after the offset of the saccade;

a vergence parameter is the amplitude of a vergence, the amplitude being defined between the onset of the vergence and the offset of the vergence, the onset of the vergence being defined by the instant for which the vergence has a velocity of x % of the peak velocity of the vergence, the offset of the vergence being defined by the instant after peak velocity for which the vergence has a velocity of x % of the peak velocity, x being between 5 and 15°;

the visual or audiovisual vergence test consists of subjecting the person to a first visual or audiovisual stimulus and then subjecting him/her to a second visual or audiovisual stimulus located at a different place from the first visual or audiovisual stimulus (at a lower or higher depth, at the same eccentricity as the first place, generally in front of the person), a vergence parameter being a latency defined by the time between the moment of activation of the second visual stimulus and the onset of the trajectory of the eyes to move from the first visual stimulus to the second visual stimulus;

a vergence parameter is the duration of vergence defined by the time between the offset of eye movement and the onset of eye movement;

a vergence parameter is the amplitude of the difference between the two eyes between the onset of the vergence movement and the offset of the vergence movement;

a vergence parameter is the amplitude of the vergence drift during the 80 ms or 160 ms after the offset of the vergence movement;

a visual test is a test of the reading of a text, the trajectories being progressive saccades to the right and/or regression saccades to the left, i.e. returns to the previous word. It can also be a test of reading an image.

With the invention it is therefore possible to test and analyze the movements of both eyes in 3D (in direction and depth: saccades and vergences).

Moreover, the stimulations are physical: for example visual or audiovisual targets anchored at eccentricities and depths on the surface of the stimulation device (REMOBI), or during the reading of text, or the reading of an image. The person sees naturally with both eyes—i.e., no stereovision, virtual reality, or 3D screen glasses are used. Thus the person's vision is natural. It is therefore about stimulation in real 3D space.

The invention makes it possible to process data of the eye movements of a person stimulated by visual or audiovisual targets placed in real space at eccentricities and depths as provided in particular by the REMOBI device, or during the reading of text (on book or screen) or image reading on book or screen. All the stimulations used in the invention are physical and seen naturally with both eyes. Therefore, no stereovision, virtual reality, or other artificial vision process is used.

DESCRIPTION OF THE FIGURES

Other characteristics, purposes and advantages of the invention will be apparent from the following description, which is purely illustrative and non-limitative, and should be read in conjunction with the attached drawings on which:

FIGS. 2a, 2b, 2c, 2d illustrate ways of stimulating a person's binocular motor skills;

On all the figures, similar elements bear identical references.

(B) Vergence trajectories during a vergence test. (C) Saccades trajectories during a saccade test. (D) Eyes movements during an image analysis test.

Figures 17A, 17B:
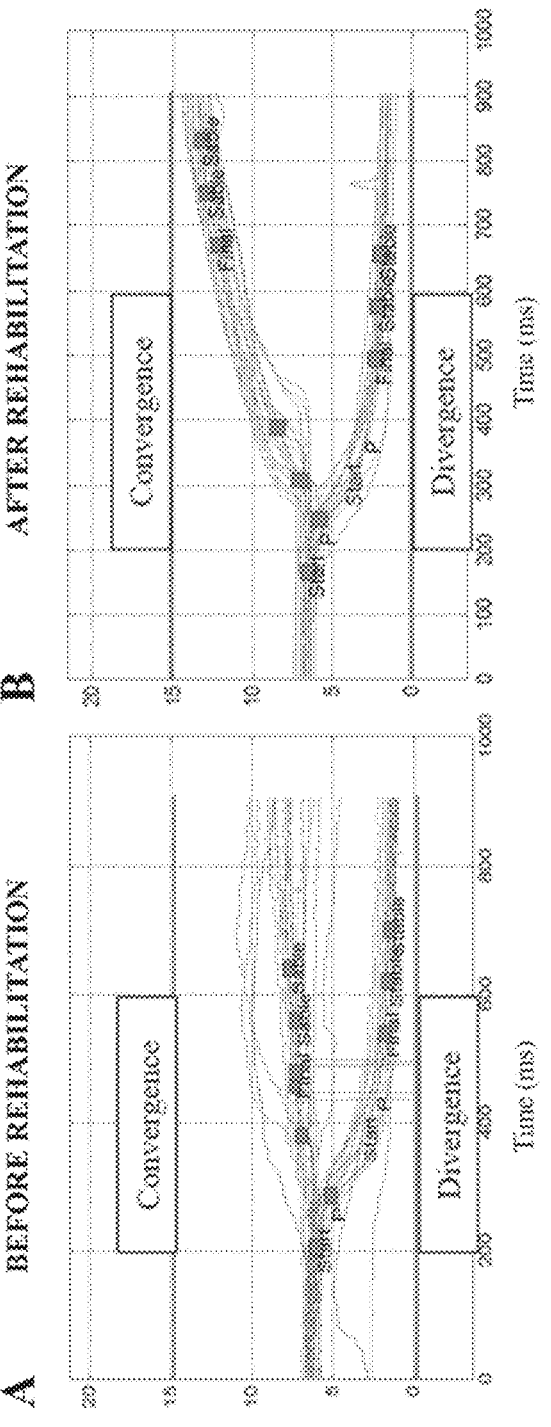

FIG. 17A: Trajectories of convergences and divergences from patient 5 (vestibular asthenopia, hypersensitivity) before rehabilitation with REMOBI; the target had appeared at zero time. After a latency of about 200 msec the vergence movement begins. The trajectories are slow, variable and hypsometric especially for the convergence which does not reach its target (indicated by the bold line). FIG. 17B: Trajectories of the vergences of the same patient 1 month after the end of the rehabilitation with REMOBI. Convergence trajectories increase to almost reach the target (high bold line), movement dynamics accelerate.

Figure 18:
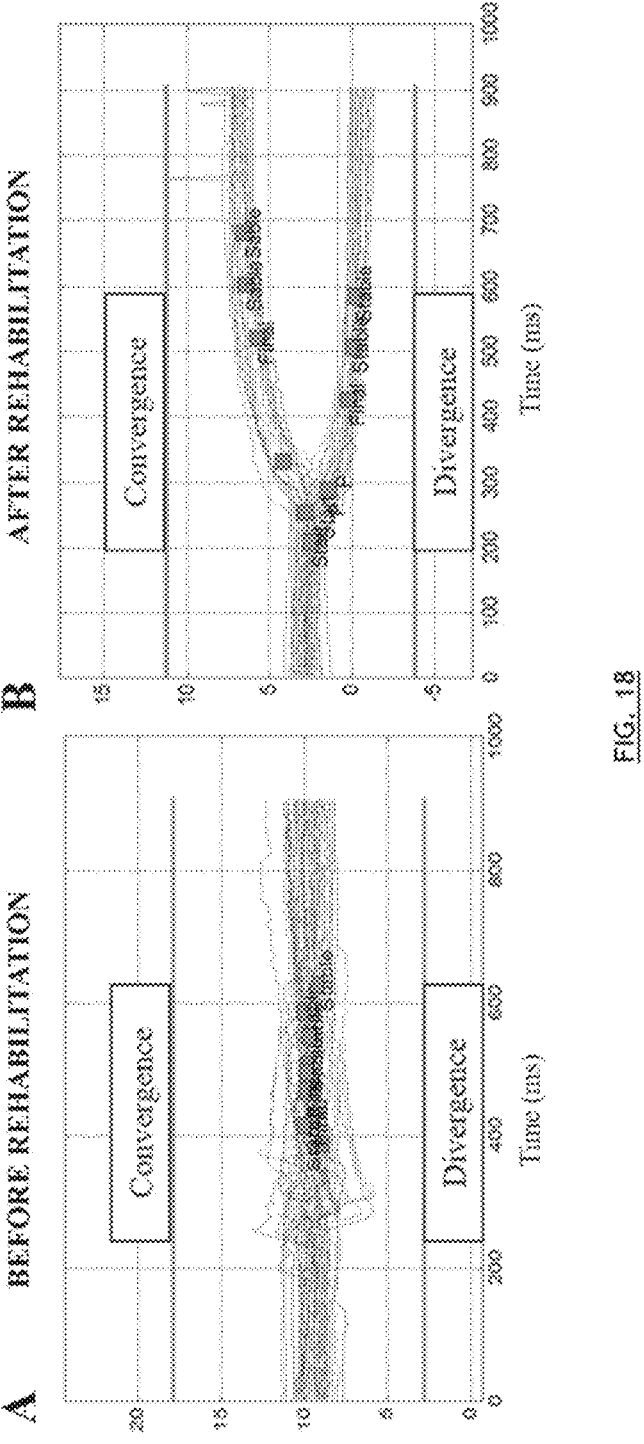

FIG. 18A: Trajectories up for convergence targets, down for divergence targets of patient 14 suffering from an old and well documented left Meniere's disease (chronic vertigo, right hyporeflectivity). The trajectory is deficient in both cases (other notations as in FIG. 7). FIG. 18B: Improved trajectories of the same patient after rehabilitation.

Figure 19:
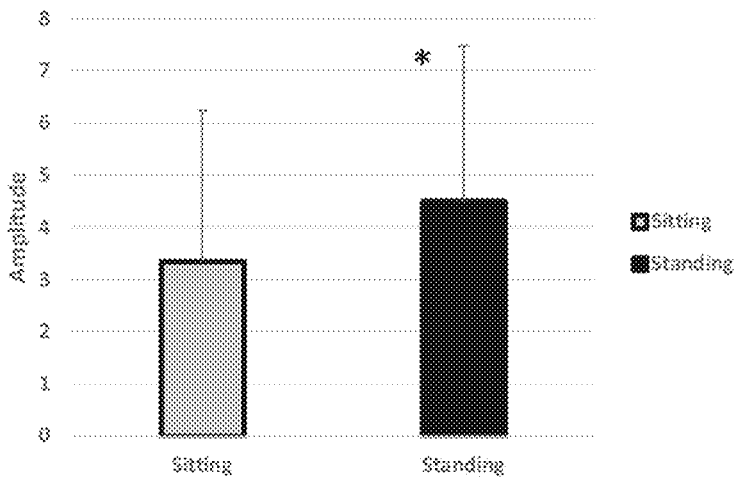
Figure 19:
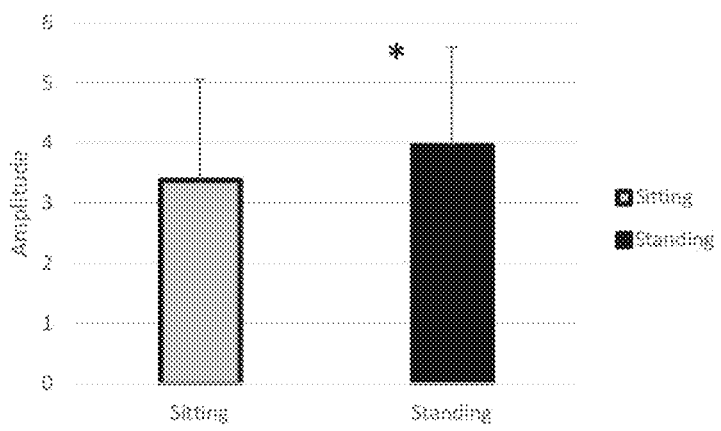

FIG. 19. (A) Amplitude of convergence in sitting and standing conditions in vergence test after rehabilitation, (B) Amplitude of divergence on sitting and standing conditions vergence test after rehabilitation.

Figure 20:
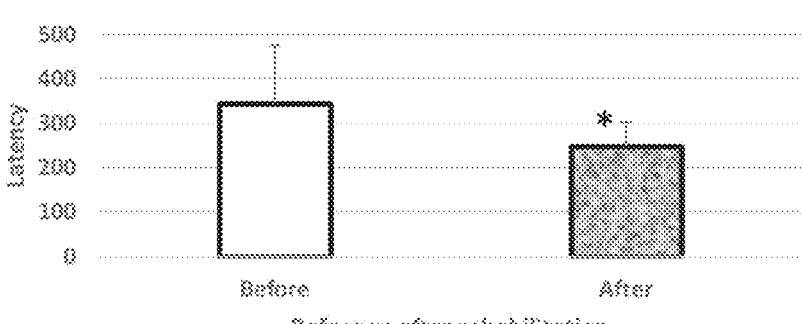

FIG. 20. Latency of divergence before and after eye rehabilitation in individuals with vertigo.

Figure 21:
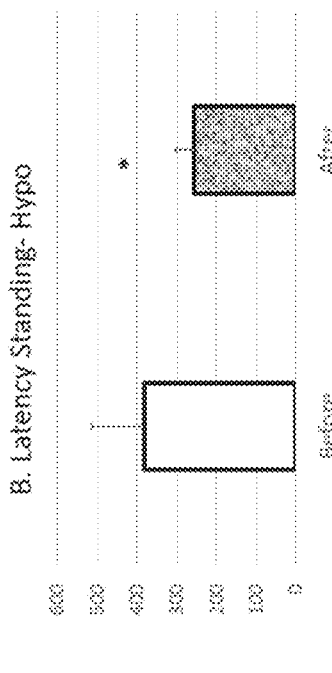
Figure 21:
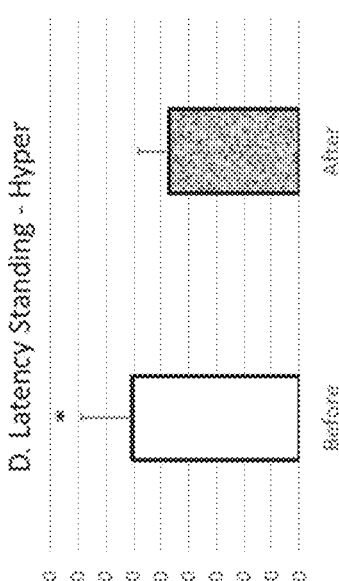
Figure 21:
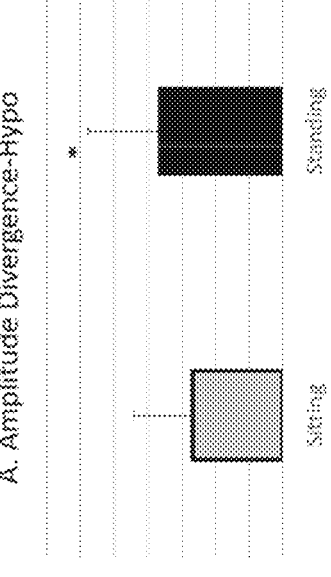
Figure 21:
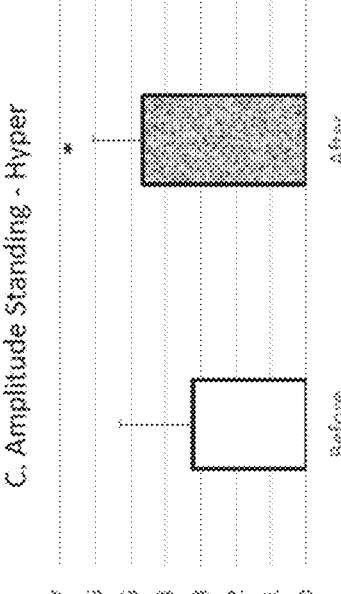

FIG. 21A: Amplitude of divergence in standing vs seated condition. FIG. 21B: Latency of the divergence in standing position before and after rehabilitation in patients with organic origin of the vertigo (hypo). FIG. 21C: Amplitude of the divergence in standing position before and after rehabilitation in patients with functional origin of the vertigo (hyper). FIG. 21D: Latency of the divergence in standing position before and after rehabilitation in patients with functional origin of the vertigo (hyper).

Figure 22:
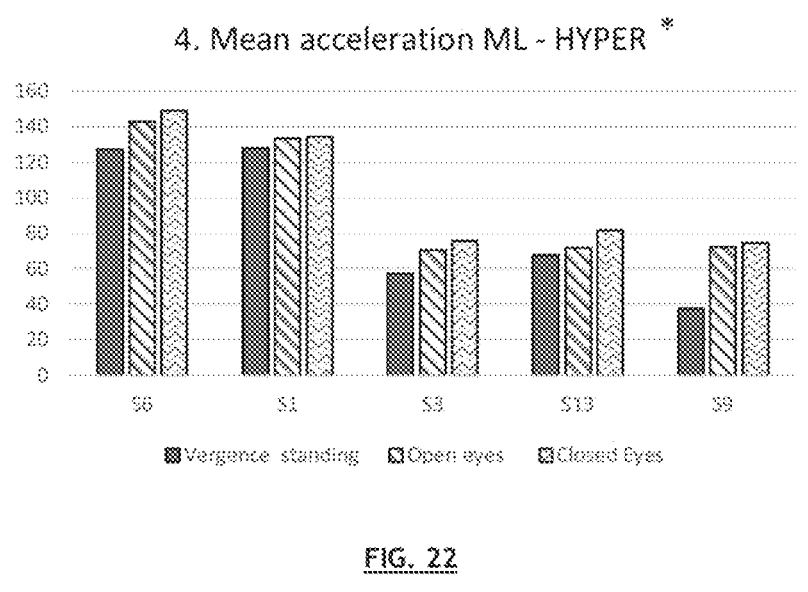

FIG. 22: Medio lateral accelerations of vergence standing, eyes open and eyes closed conditions on organic patients.

Figure 23:
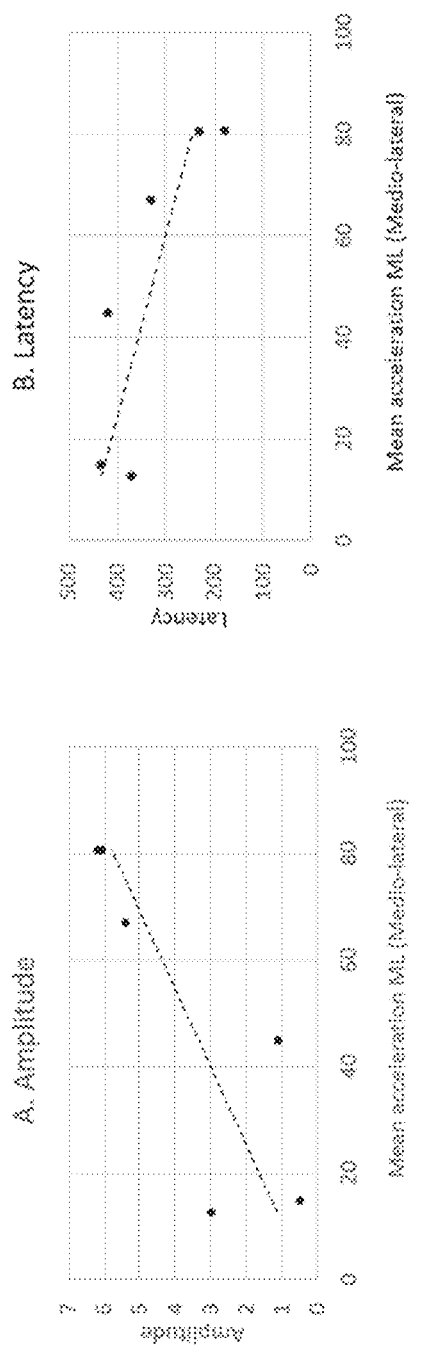
Figure 23:
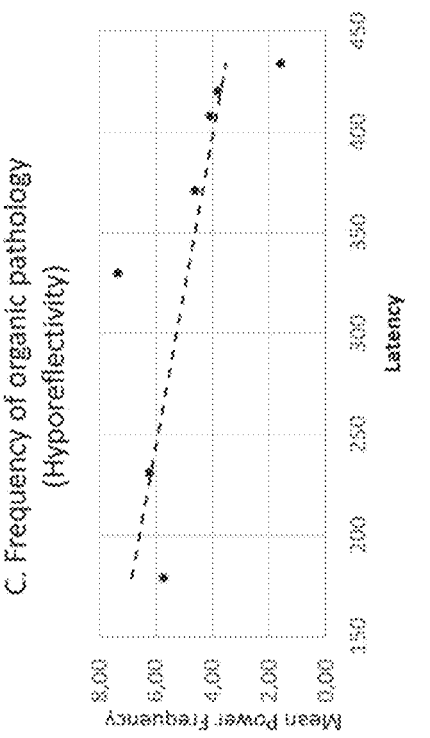

FIG. 23: Correlation between Medio lateral acceleration and amplitude (A) and latency (B) in hyporeflectivity patients. (C) Correlation between Mean power frequency and latency in Hyporeflectivity patients.

DETAILED DESCRIPTION OF THE INVENTION

In everyday life, subjects constantly make eye movements about three times a second to explore the 3D environment. The essential movements are saccade and vergence movements.

The saccades are rapid movements of refixation of the gaze from one point to another laterally, vertically, or both at the same time (we speak then of oblique saccades).

The movements of vergence are movements of the eyes in the opposite direction: to fix a close object, the left eye turns to the right and the right eye turns to the left; this convergent movement of the eyes makes it possible to increase the angle of the convergence of the axes.

To fix a distant object the left eye turns left, and the right eye turns right; this divergent movement allows to decrease the angle of convergence of the two optical axes, by making the optical axes almost parallel.

Usually, movements combining saccades and vergences are performed together. These movements are carried out almost simultaneously, at least for a certain time: indeed, the vergence being slower than the saccade, when combined with the saccade it accelerates considerably, then continues after the saccade if necessary.

The notions of saccade and vergence movement are presented below.

A saccade corresponds to a change in the position of the gaze. It results in a rotation of the binocular globes allowing a new target to be projected onto the fovea of both retinas. A saccade is very fast (up to 800°/s) and is therefore of very short duration (50 to 150 ms). It is the fastest movement that a human being can produce. A saccade is normally used to change the point of fixation, therefore to seek information elsewhere in the visual field. It does not, in itself, bring information at the visual level, although the retina and the visual system still function normally during its occurrence.

Vergence movements allow the eyes to rotate in opposite directions. They are the only dis-conjugated binocular movements of the visual system. The vergence movements allow to see at different distances in depth. The eyes converge to see a closer target and diverge to see a farther target. This adaptation to distance is done through the accommodation triad, or near triad, which includes vergence movements (fusion convergence), accommodation (lens deformation) and, to a lesser extent, pupil contraction/decontraction. These three components of vision are very closely related.

Although these parameters are classically used for the study and diagnosis of various pathologies, the Applicant has realized that to date there is no automatic, rapid analysis of these movements taking into account both eyes, in direction and depth.

Figure 1:
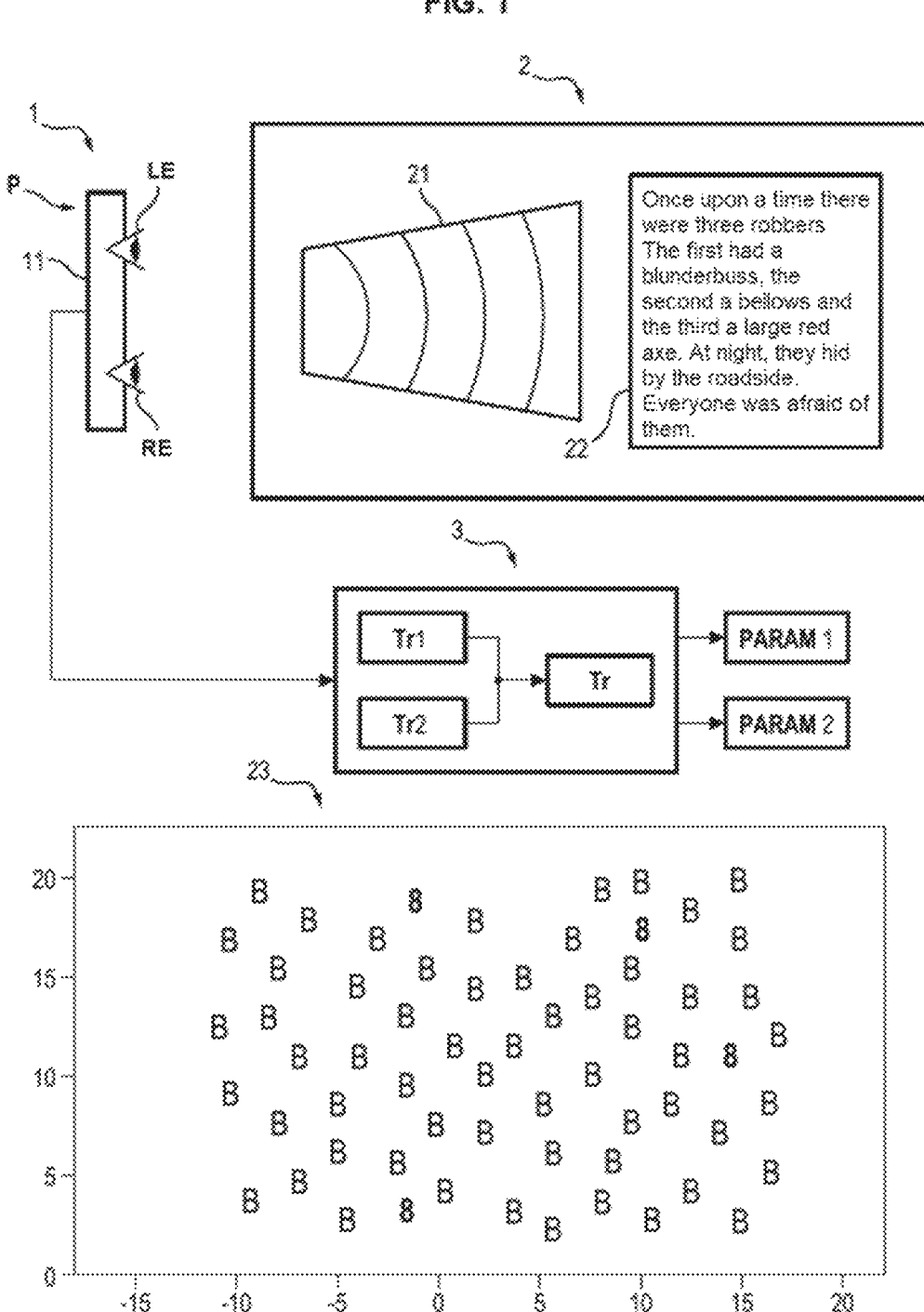
FIG. 1 illustrates a system for processing data representative of a person's binocular motricity.

In relation to FIG. 1, a system 1 for processing data representative of the binocular motricity of a person P comprises a stimulation part 2, a system for acquiring and recording 11 the eye movement of a person P, in particular, the movements of the right eye RE and the left eye LE of a person. In addition, the system includes a processing unit 3 configured to implement steps of a data processing procedure representative of the binocular motor skills of a person P and which will be described below. Such a process makes it possible in particular to obtain saccade parameters PARAM 1 and/or vergence movement parameters PARAM 2.

Advantageously, from saccade parameters PARAM 1 and/or vergence movement parameters PARAM 2 it is possible to evaluate a person's disorder.
Visual Tests Stimulation part 2 advantageously includes two types of stimulation of the binocular motricity of a person P. The effect of these stimulations is to provoke saccades or vergences and movements combining saccades and vergences.

A first type of stimulation is implemented by means of a device that stimulates binocular motricity by sensory stimulation means such as diodes and sound diffusion means that are arranged along different iso-vergence arcs in front of a person: an iso-vergence arc is such that the angle of vergence of the two eyes required to fix each point on this arc is the same. This device advantageously includes four iso vergence arcs. Preferably the sensory stimulation means are placed on a flat support. Such a device used for the first type of stimulation is described in patent EP 2 512 395 B1, patent CA 2 784 541 C, patent FR 2 953 711 B1, patent JP 5 671 055 B2, U.S. Pat. No. 8,851,669 B2. This device is called REMOBI device.

The sensory stimulation means are arranged on arcs at distances between 20 and 150 cm from a person and between each stimulation means placed on the same arc there is an angle of 10 degrees. The support is advantageously mounted on a height-adjustable foot allowing the device to be positioned appropriately at the level of a person's P face. The support of the sensory stimulation means is preferably trapezoidal and has appropriate dimensions to test the entire natural palette of eye movements (saccades at different depths iso-vergence arcs, vergences along the median plane, movements combining saccades and vergences) and to rehabilitate binocular motricity in direction (saccades), depth (vergences) or combining them. The stimulation offered by this type of device is modular, it can be audiovisual (thanks to light diodes and sound means), audible only or visual only. The visual and sound stimulation means are targets for the person. Each means of sensory stimulation is represented by a voltage so that it is possible to acquire a corresponding output signal that makes it possible to identify the active targets and, therefore, the type of movement that can be generated by the stimulation.

The device is advantageously driven by an embedded microprocessor which allows a controlled spatio-temporal activation of the diodes and loudspeakers. Different stimulation protocols, adapted to different types of pathologies, can thus be used and implemented to diagnose and rehabilitate eye movement disorders. These protocols are based on sequences allowing lateral and/or deep eye movements.

FIGS. 2a, 2b and 2c show three stimulation modalities using the binocular motor stimulation device. Visual stimulation using diodes is considered, without limitation. The diodes are switched on one by one, one diode is switched off before switching on the next so that only one diode is on at a time. In FIG. 2a, a vergence test is illustrated: the diode in position F is initially lit, then those in position T are lit. On FIG. 2b: a saccade test is illustrated: the diode in position F is initially lit, then those in position T and then T's are lit; the saccade test can be done, without limitation, with the targets at 40 cm as shown in FIG. 2B, but also at 20, 70 or 150 cm. On FIG. 2c: a combined movement test is illustrated: the diode at position F is initially lit, then those at position T then T', T" and T" are lit. The time the diodes are on is part of the test modalities and depends on the pathologies studied. Other tests use the so-called double step paradigm of the target and are used for the rehabilitation of binocular motor skills: the diode in position F is initially lit, then those in position T then T' and 200 ms later T" is lit; with repetition the brain quickly learns to program a single accelerated and ample movement aiming at the second position of the target T". One can also refer to the modalities described in the document EP 2 512 395 B1.

A second type of visual stimulation is that implemented by means of a reading test 22. This stimulation simply consists of having person P read a text and acquiring and recording eye movement during reading. The test is advantageously held by the person in a position that offers reading comfort. Also, this reading test includes the visualization of an image that is "read" by person P. Also, the test can be of the "bell barrage test" type 23 (see FIG. 1). Such a test consists of recognizing one character among others that are identical. In FIG. 1, the test 23 includes several letters B among which are arranged numbers 8, the test consists in identifying the 8. The trajectory followed by the eyes will be recorded. An alternative to this test is to position the letter L among several characters representing a symbol '⊥'. The test consists in identifying the L, again the trajectory of the eyes will be recorded during this identification.

During the stimulations described above, the person is equipped with an eye movement acquisition and recording system (see below) in order to be able to acquire and record the movements following the different stimulations or during reading.

Advantageously, each test on the REMOBI device includes twenty repetitions in a pseudo-random way for each target (e.g. left saccade, right saccade, convergence or divergence). Also, a typical trajectory for all saccades to the right can be predicted during reading.

Eye Movement Acquisition and Recording System

A system of acquisition and recording of eye movements 11 allows to measure the binocular movement, and more precisely the image of the pupil, constituting the center of analysis. It covers the following areas:

the follow-up (of the direction) of the glance of a subject (human being);

binocular control, i.e. the use of the gaze to activate/validate a function such as clicking on an icon, moving the mouse, etc.

The system for acquiring and recording eye movements works advantageously with a videoculograph, i.e. micro-cameras that focus their lenses on both eyes and record their movements when the person is staring at the device to stimulate binocular motor skills 21 or when he or she is reading a reading test 22.

In this case, the micro-cameras capture the contrast between the retina and the pupil using a projection of infra-red light, by analyzing the light reflected by the cornea of the human eye. By alternating contrasting reflections from the pupil (light/dark), it becomes possible to "follow the movement of the eye".

Such a system is for example an oculometer from the company Pupil Labs™ which allows not only the position of the eyes but also other parameters as well as video of the eyes and what the person sees. However, only the position of the eyes is useful in what is going to be described. Another type of eye movement acquisition system is the Powref III from the company PlusOptix™. Such a type of system is placed at a distance from the person, for example in front of the person on the REMOBI support. This system allows to measure the eye movement but also, at a distance, the change of eye accommodation for and to plot eye positions but also the plot of the change of eye accommodation. In this regard, one can refer to the document "HSOA Journal of Clinical Studies and Medical Case Reports", Kapoula Z, et al, J Clin Stud Med Case Rep 2019, 6:74. FIG. 2d shows a person in front of the REMOBI device with an eye movement acquisition system placed on the support. The person is subjected to a vergences test according to the modalities illustrated in this figure. The vergence movement and the change in accommodation are recorded and illustrated in this figure as well.

Treatment Process (Called AIDEAL, "Automatic Intelligent Eye Movement Analysis")

Figure 3:
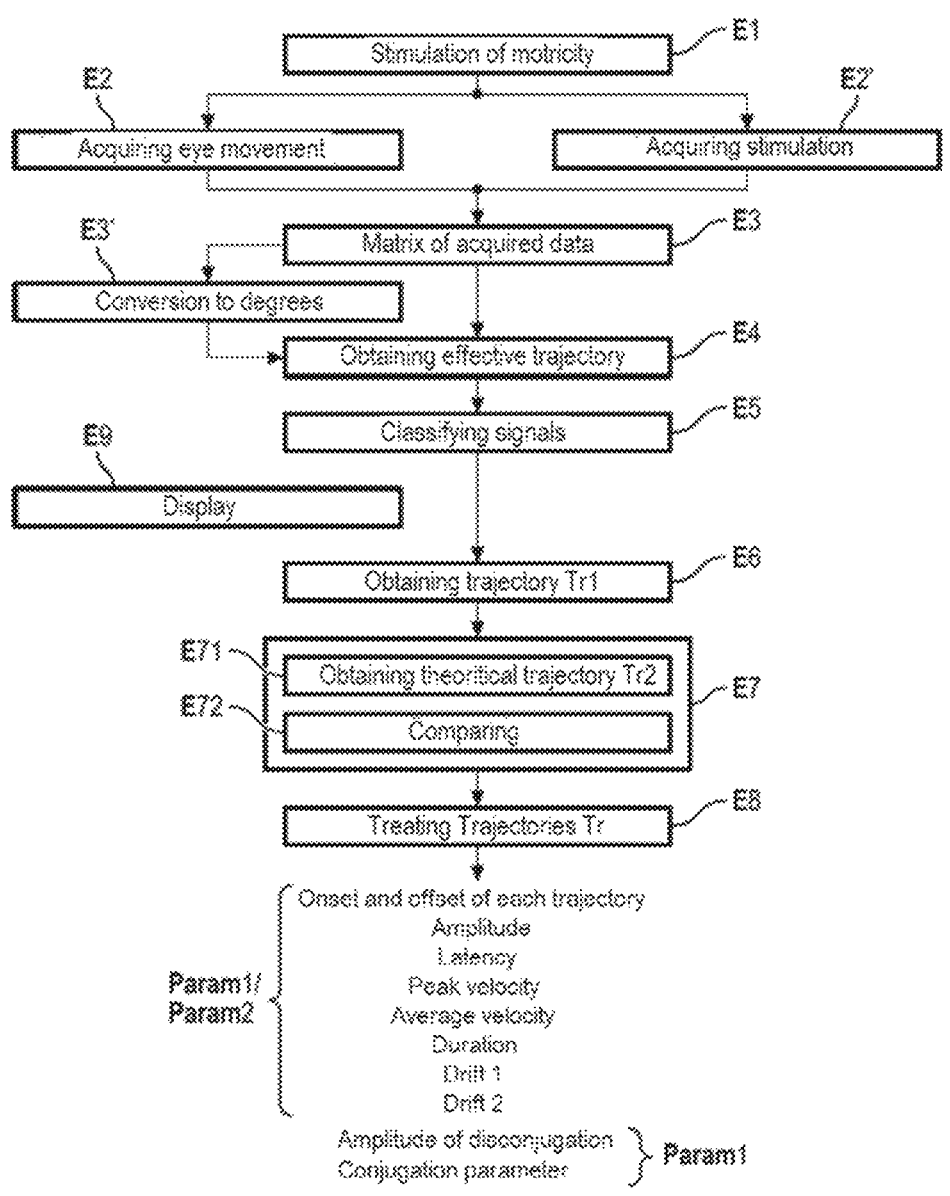
FIG. 3 illustrates steps in a process for processing data representative of a person's binocular motor skills.

FIG. 3 illustrates steps in a process for processing data representative of an individual's binocular motor skills.

The binocular motricity of a person P is stimulated E1 by means of a binocular motricity stimulation device 21 or by a text or image reading test 22.

During stimulation 21 or 22, E2 acquisition of the movement of the right and left eye is performed.

In addition, if the binocular motor stimulation device 21 is used, the E2' acquisition of a stimulation signal indicating which means of sensory stimulation is activated over time is implemented: which diodes, which loudspeaker if any.

The acquired data relating to eye movement is time-stamped in seconds, as is the stimulation signal.

Thus, at the end of the acquisition steps E2, E2' we obtain E3 data grouped in a matrix comprising nine columns:

column 1: time scale corresponding to the signal emitted by the binocular motor stimulation device (in seconds);

column 2: signal emitted by the binocular motricity stimulation device, this signal corresponds to the lighting of the luminous diodes (in volts);

column 3: time scale corresponding to the positions (in seconds);

columns 4, 5, 6: position in x, y, z of the right eye (in arbitrary units);

columns 7, 8, 9: position in x, y, z of the left eye (in arbitrary units).

Understandably, if the reading test is used then the first two columns are not filled. Advantageously, the data corresponding to the position of the eye in a 3D space of the eye are converted E3' into degrees as usually expressed. Indeed, the eyes make rotations around the vertical or horizontal axis and these rotations are measured in angular degrees.

From these data, the process includes an E4 determination of an effective trajectory (Tr1) of the eyes in response to each stimulation, an effective trajectory corresponding to a saccade and/or a vergence movement of the eyes. Indeed, it is assumed that it is known which test was used to stimulate a recorded movement.

In particular, the trajectory corresponding to a saccade is obtained by calculating a conjugated signal defined by the average of the position of the left eye with the position of the right eye.

Note that the type of movement depends on the test used. A saccade test sequence (see FIG. 2b) can only provoke saccade movements; a vergence type test (see FIG. 2a) can only provoke vergence movements.

Also, the effective trajectory corresponding to a vergence is obtained by calculating a non-conjugate signal defined by the difference of the left eye position with the right eye position.

If the binocular motor stimulation device 21 is used, the different saccades and vergence movements are classified as E5 to take into account the location of the sensory stimulation means used when the corresponding eye movements are analyzed. Indeed, in order to test the natural physiological oculomotor performance, it is important to have the targets unpredictably mixed to the left or right of the fixation point (for saccades) or forward or backward for vergences. This prevents the person from anticipating the direction or depth at which their gaze should move. For the analysis of eye movement properties it is important to characterize the parameters separately for each movement subclass. Indeed, it is possible to have deficits specific to the direction (left vs. right) or the type of vergence (convergence or divergence). There are even natural asymmetries between different subgroups of movements (e.g. convergence stronger than divergence, or saccades to the right better than saccades to the left even in the normal population). In the case of saccades, the signals are classified according to the lit diode (for a diode on the right, conjugated signal of the saccade upwards, for a diode on the left of the fixation diode, conjugated signal of the saccade downwards). Two data matrices are created (for right and left movements).

For vergence movements, the classification is made according to the diode on, for convergence (signal upwards) for divergence (signal downwards).

We understand that we obtain a set of Tr1 trajectories from the acquired signals.

Figure 4:
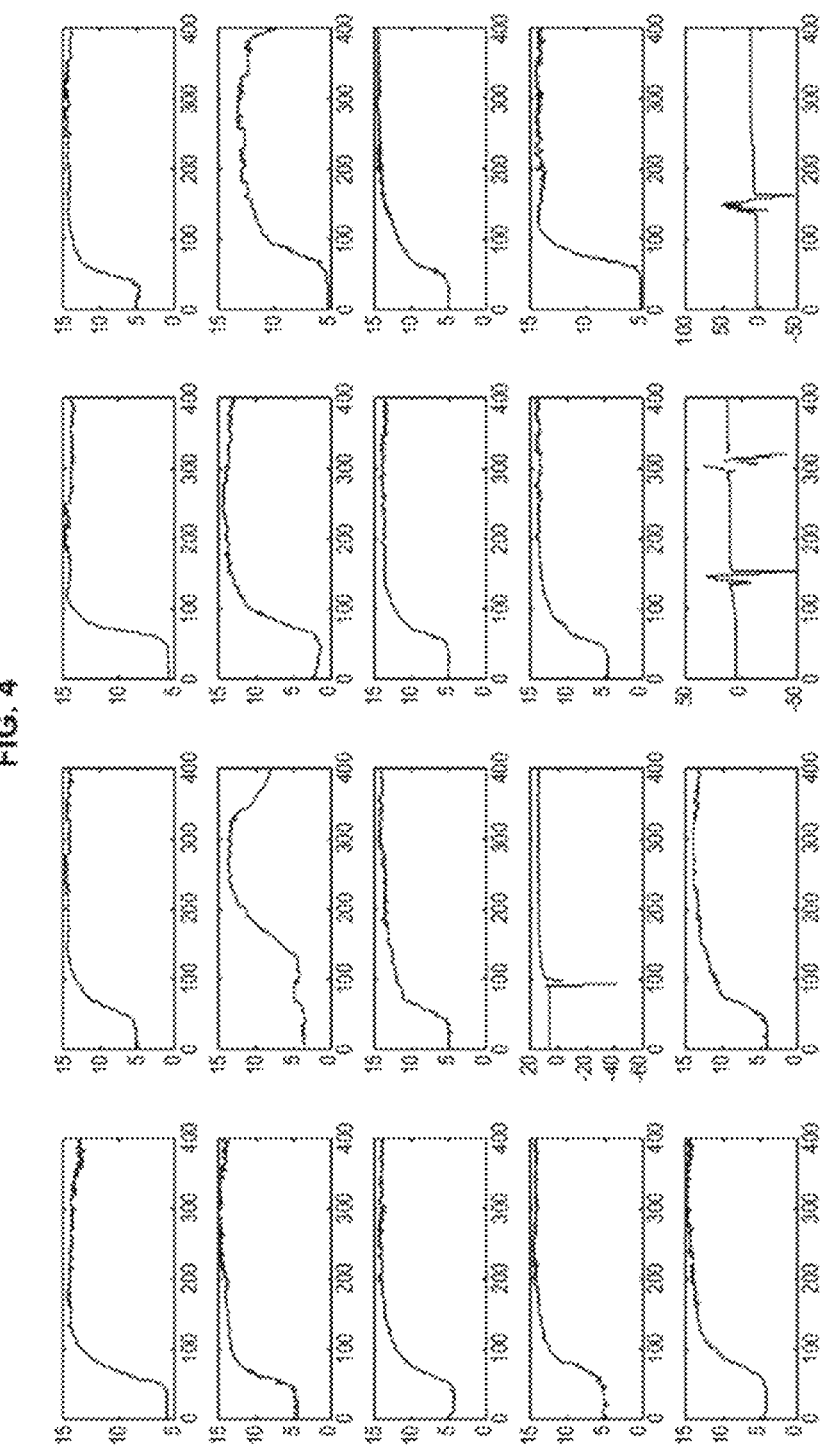
FIG. 4 illustrates several trajectories of the eyes performing a convergence movement.

FIG. 4 illustrates several eye trajectories that converge.

However, some trajectories may be wrong. As such, the process includes a treatment of the trajectories described below (step E7).

A set of representative trajectories Tr2 of the eye movement for each given stimulation is calculated (step E71). To do this, all the measured trajectories (so-called "effective trajectories") relating to this stimulation are used. Then (step E72) the trajectory Tr1 resulting from the measurement is compared for each stimulation with the representative trajectory Tr2 for this stimulation in order to eliminate the erroneous trajectories and thus obtain the selected trajectories Tr.

In particular, the comparison (step E72) consists in calculating a distance between the effective trajectory and the theoretical (also referred to as "representative") trajectory and if the distance is greater than a fixed threshold, the trajectory is eliminated. As a result, only those measures that correspond to the stimulus under consideration are included.

The elimination of erroneous trajectories is implemented by means of a DTW (Dynamic Time Warping) algorithm.

Such an algorithm measures the similarity between two sequences that may vary over time.

The DTW algorithm is classically exploited in video, audio, computer graphics, bioinformatics and can be applied in any situation where the data can be transformed into a linear representation.

In general, the DTW algorithm is a method that searches for an optimal match between two time series, under certain restrictions. Time series are distorted by a non-linear transformation of the time variable, to determine a measure of their similarity, independent of certain non-linear transformations of time. This method of time series alignment is often used in the context of hidden Markov models.

In the case described here, the aim is to eliminate trajectories that are too far from theoretical trajectories.

Figure 5:
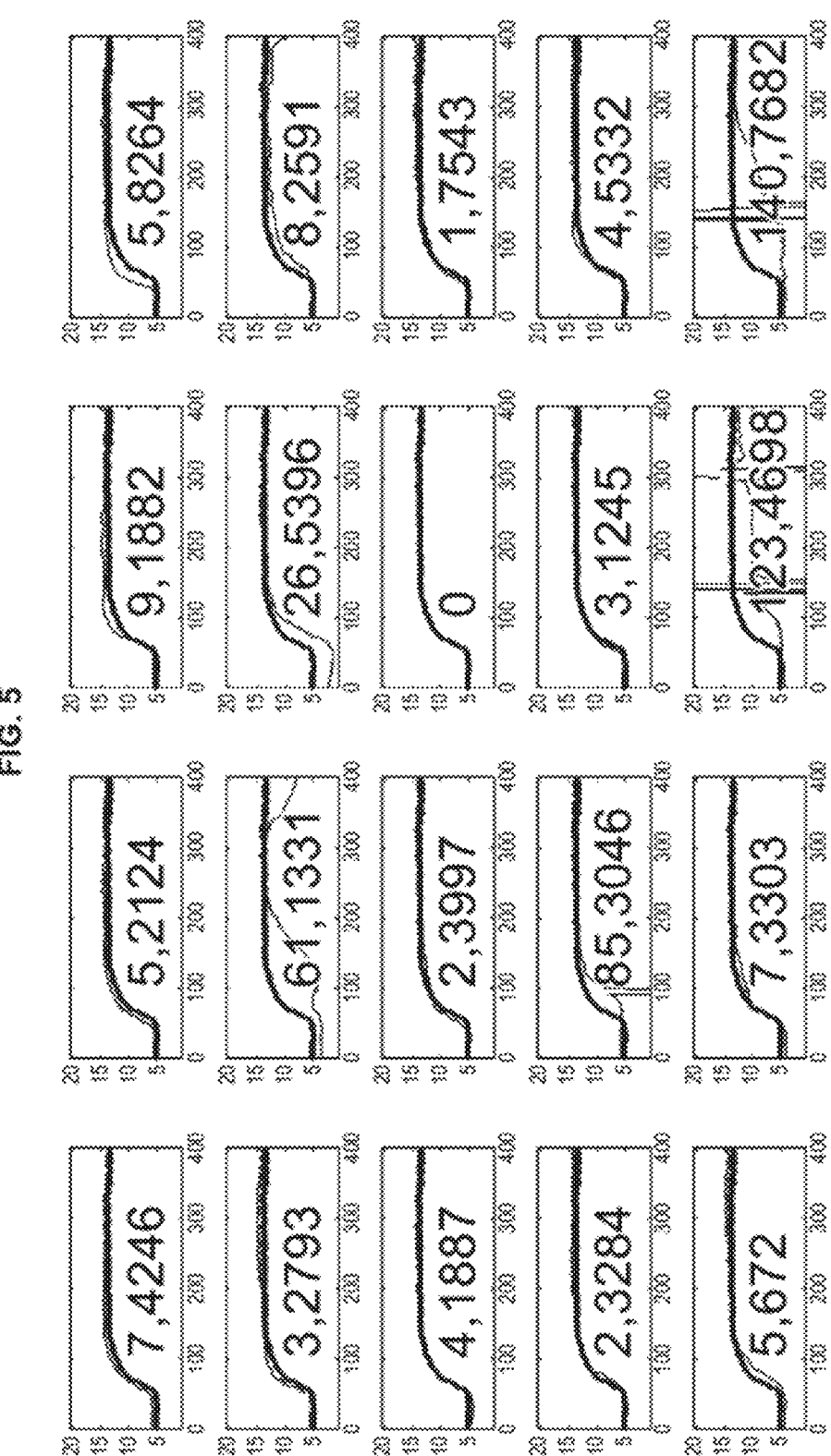
FIG. 5 illustrates an indicator showing the distance between the theoretical (also referred to as "representative") trajectory (thicker line) and the measured trajectory (thinner line)

FIG. 5 illustrates an indicator that shows the distance between the theoretical (also referred to as "representative trajectory") trajectory (thicker line) and the measured (or "effective") trajectory (thinner line). For example, the indicator (61.1331; 85.3046; 123.4698; 140.7682) is high, indicating that the measured trajectory is far from the theoretical trajectory. In this example, all cases with an indicator greater than 10 are eliminated, i.e. 5 here.

For each trajectory, the onset and offset of the eye movement is detected by calculating the velocity of the acquired trajectory signal (the derivative of the signal of the instantaneous eye position). In particular, the onset of the saccade or vergence is the point where the velocity exceeds x % (x % between 5 and 15%, preferably 10%) of the peak velocity, and the offset of the saccade or vergence is the point after peak velocity where the velocity is less than x % (x % between 5 and 15%, preferably 10%) of the peak velocity. Other velocity criteria, e.g., for saccades, a velocity >45 degrees per second for the onset of the saccade and less than 45 degrees per second for the offset can be used. Similarly, for vergences, a velocity >5 degrees/see for the onset of the vergence and less than 5 degrees per second for the offset can be used.

Then, once the trajectories are well selected, the process includes a step E8 of treatment of each selected trajectory Tr in order to obtain parameters of saccade and/or vergence, the parameters being characteristic of a possible pathology of a person.

Each saccade and vergence parameter are described below.

Before describing the parameters, it should be noted that the processing of the data relating to the stimulation by the reading test is similar to that for saccades. Indeed, during reading, the eyes make a succession of saccades followed by fixation, progressively from left to right, then a large saccade to the left and down to the next line.

Parameters of Saccades

Detection of the start of the stimulation signal (the ignition of the target diode of the binocular motor stimulation device) using the velocity of the signal. This target signal is used to measure saccade latency (see below);

Latency (in ms) is the time between the switching on of the target diode and the onset of the saccade (when pacing with the binocular motor stimulation device);

Amplitude is the difference in degrees between the offset of the saccade and the onset of the saccade. The onset of the saccade is defined by the instant at which the saccade has a velocity of x % the peak velocity of the saccade, the offset of the saccade is defined by the instant after peak velocity at which the saccade has a velocity of x % of the peak velocity, where x is between 5 and 15, preferably 10. Note that it is possible to set other criteria than the x % of peak velocity, such as a velocity criterion adjusted according to the magnitude of the saccades studied: for example, for large saccades (10, or 20 degrees), a velocity greater or less than 45 degrees per/sec allows to discern the onset and the offset of the saccade with a good precision;

Duration (ms): the time in msec between the onset and the offset of the movement;

Peak velocity (degrees/s): maximum value of the saccade velocity signal;

Average velocity (degrees/s): amplitude of the saccade in degrees divided by the duration of the saccade (in seconds);

Disconjugation parameters: obtained from the signal of the difference between the position of the left eye LE−right eye RE:

Amplitude of the dis-conjugation (in degrees) of the defined saccade: amplitude of the difference between the two eyes between the onset and the offset of the saccade (this is equivalent to the difference in the amplitude of the saccade between the two eyes);

Drift 1 (in degrees): amplitude of the dis-conjugation between the offset of the saccade and up to 80 ms after the offset of the saccade; the difference between these two points is taken to measure the amplitude. But one can also average the values of dis-conjugation between all the points from the offset of the saccade to 80 ms afterwards;

Drift 2 (in degrees): amplitude of the dis-conjugation between the offset of the saccade and up to 160 ms after the offset of the saccade.

Parameters of Vergence Movements

Detection of the start of the stimulation signal using the signal speed of the diode of the binocular motor stimulation device. From this signal the latency of the vergence is measured (see below);

Latency (ms): time (in ms) between the ignition of the target diode and the onset of the vergence (when the stimulation is performed by means of the binocular motor stimulation device);

Amplitude: difference in degrees between the offset of the vergence (the point where the velocity of the vergence is less than x % of the peak velocity, x being between 5 and 15, preferably 10, or the point where the velocity of the vergence falls below 5 degrees/sec) and the point of the onset of the movement (the point where the velocity is x % of the peak velocity, x being between 5 and 15, preferably 10, or the point where the velocity raises above 5 degrees/sec). Depending on the quality of the noise or not of the signal of the eye movements we can average five points around this value to be sure that the onset or the offset of the vergence is well identified;

Duration (ms): time between the onset and the offset of the movement considered;

Peak velocity (degrees/s): maximum value of the velocity signal;

Average velocity (degrees/s): amplitude of the movement in degrees divided by the duration of the movement (in seconds);

Drift 1 (degrees): amplitude of the vergence signal during the 80 msec following the offset of the movement; note that the average can also be considered;

Drift 2 (degrees): amplitude of the signal of the vergence during the 160 msec following the offset of the movement; note that the average can also be considered.

The saccade and vergence parameters can be used alone or in combination. In the case of combined movements, the latter include a saccade component (conjugated signal, i.e. left eye+right eye/2) and the vergence component (left eye−right eye).

In this case, the eye movement data is processed twice: once for saccades and once for vergences.

The parameters calculated for each component are the same as those previously indicated for saccade and vergence. The respective parameters for saccade and vergence are then obtained.

In a complementary way, it is possible to process the obtained data in an interdependent way. This is known as combined analysis. For this purpose, we use criteria for the detection of saccades and we evaluate the vergence (amplitude, duration, velocity) during the saccade and 80 and 160 msec after the saccade. We then obtain twice as many parameters, namely: right saccade and divergence, left saccade and divergence, right saccade and convergence, left saccade and convergence. These two analyses correspond to two different physiological hypotheses: independent control of two physiological systems of saccades and vergence; hypothesis of interaction and interdependence between the two, with the saccade guiding and accelerating the vergence.

As an illustration, a trajectory concerning a convergence and below it, the corresponding velocity signal, has been shown in FIG. 6.

Figure 7:
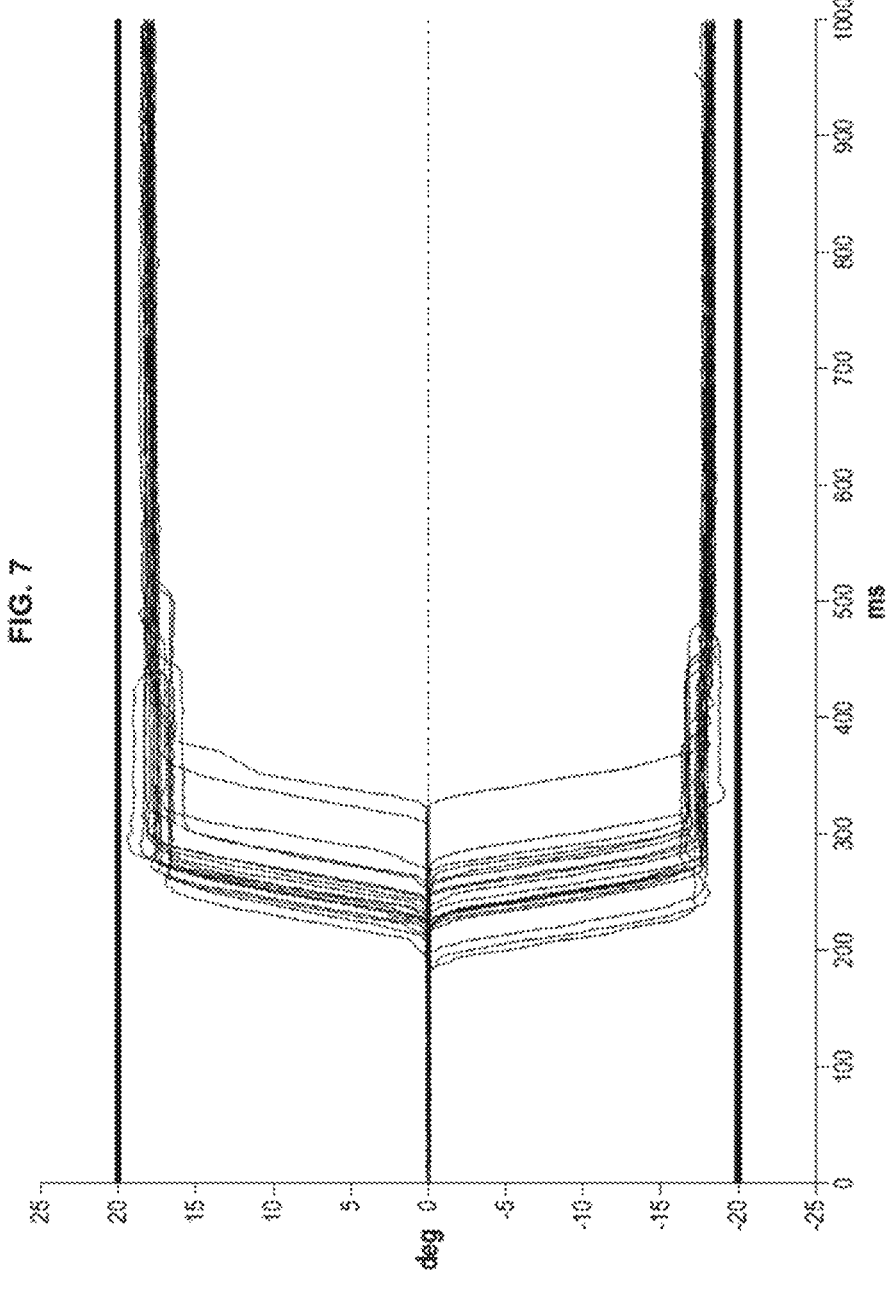
FIG. 7 illustrates saccade type trajectories to the right (top) and to the left (bottom)

FIG. 7 illustrates trajectories of the saccade type to the right (top) and to the left (bottom). These trajectories are superimposed when a diode on the REMOBI device is switched on. The ignition of the target is indicated in this figure by the horizontal lines placed 20 degrees to the left, 20 degrees to the right.

Figure 8:
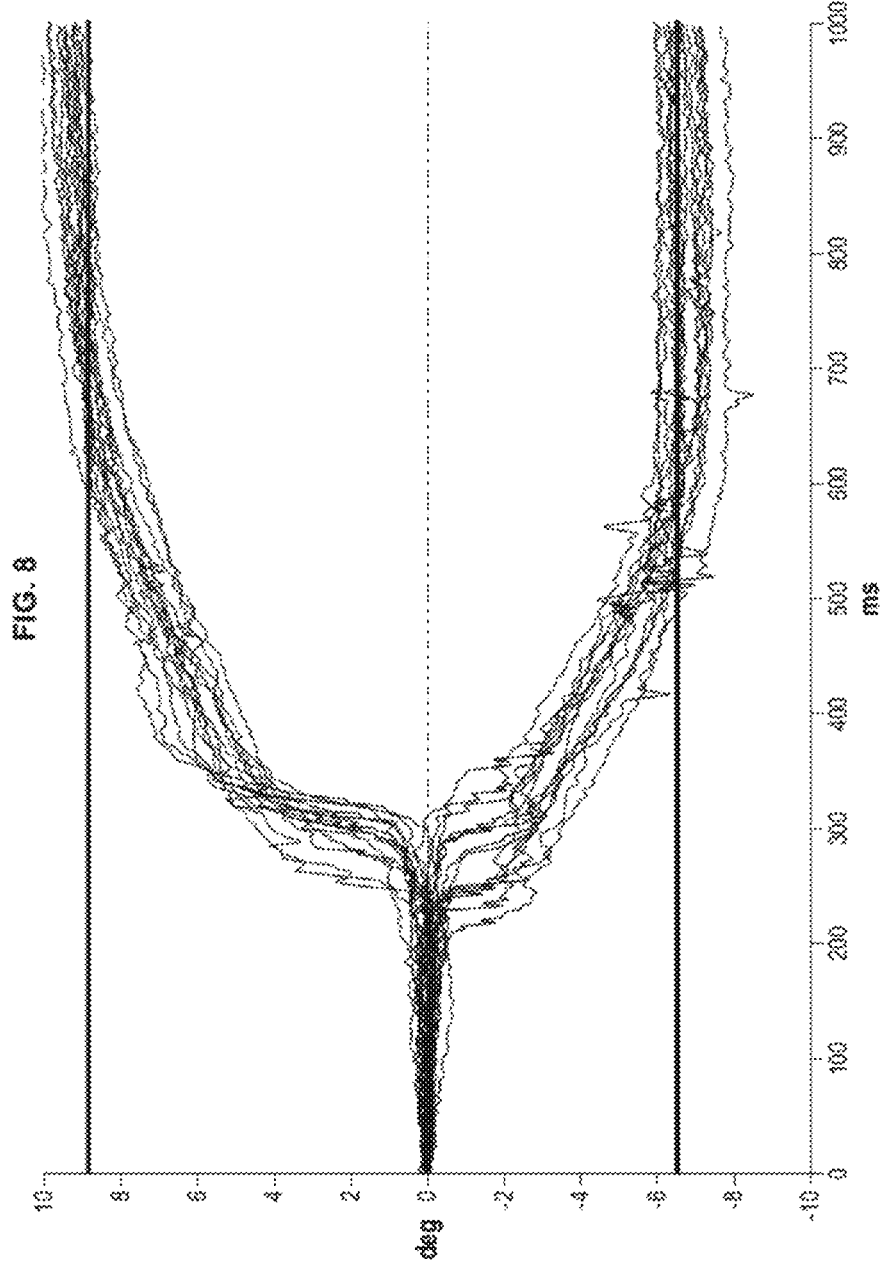
FIG. 8 illustrates trajectories of the vergence type: convergences (top), divergences (bottom)

FIG. 8 illustrates the vergences type trajectories: convergences (top), divergences (bottom). These trajectories are superimposed when a diode is lit on the REMOBI device. The ignition of the target is indicated in this figure by the horizontal lines placed at 9 degrees (convergence) and −6.5 degrees (divergence). Recall that the diode fixation is 40 cm from the person's eyes, for which the required angle of vergence is 9 degrees; the convergence target is 20 cm from the eyes for which the required angle of convergence is 18 degrees; the required range of convergence movement is therefore 8 degrees. The divergence target is 150 cm away or the required angle of vergence is 3.5 degrees. The amplitude of the required divergence movement is therefore 6.5 degrees.

In the case of the reading test, saccades are treated in the same way as saccades obtained after stimulation using the binocular motor stimulation device. The only difference is that the latency is not measurable and then there is no target signal and the reader himself decides when he triggers the next saccade. On the other hand, we measure the duration of fixation, i.e., the time between saccades. We also measure the reading speed, i.e. the number of words read per minute. A distinction is made between saccades to the right, i.e. progression saccades, saccades to the left on the same line (regression saccades) and large saccades to the left back to the next line.

Figure 9:
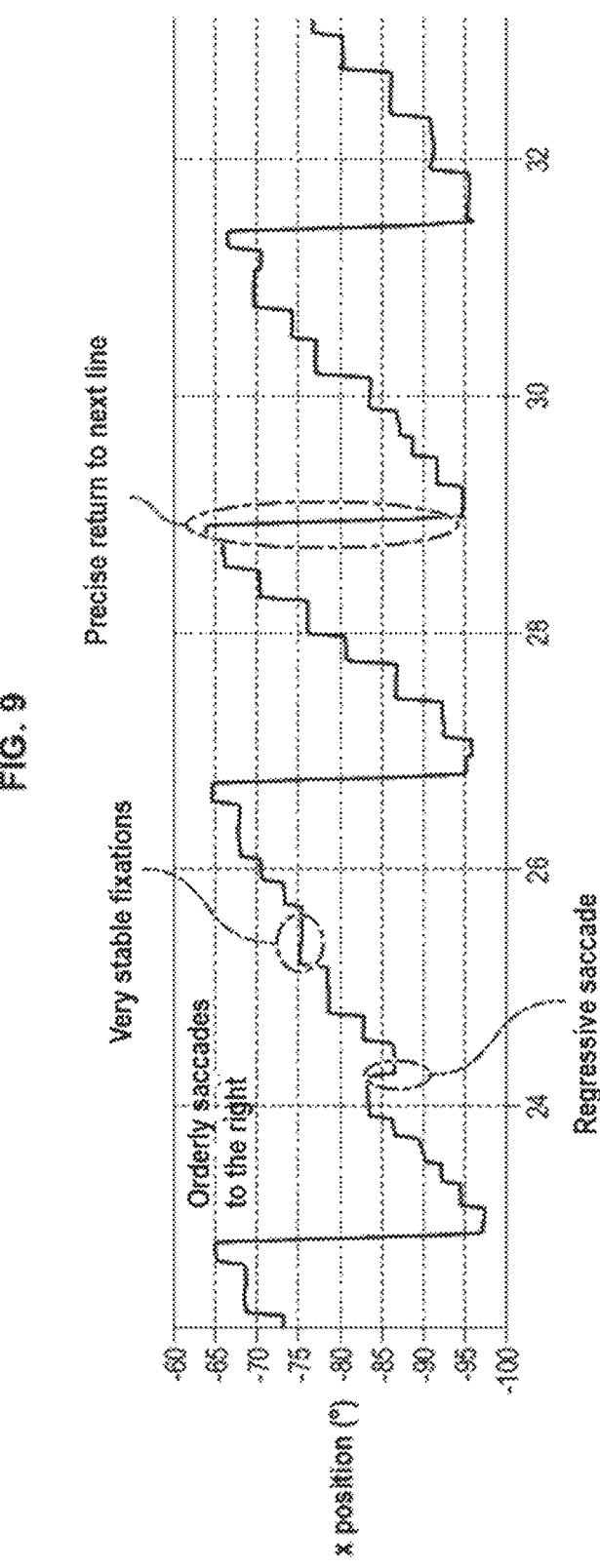
FIG. 9 illustrates the regular trajectory of the eyes of a reader who does not suffer from any pathology.

FIG. 9 illustrates the regular eye course of a reader who does not suffer from any pathology. In this figure, on the x-axis we have the time; on the y-axis the conjugated signal of the two eyes in degrees, showing the succession of saccades to the right followed by the fixations fixing the words one after the other, then the large saccade to the left to start reading the following line.

Figure 10:
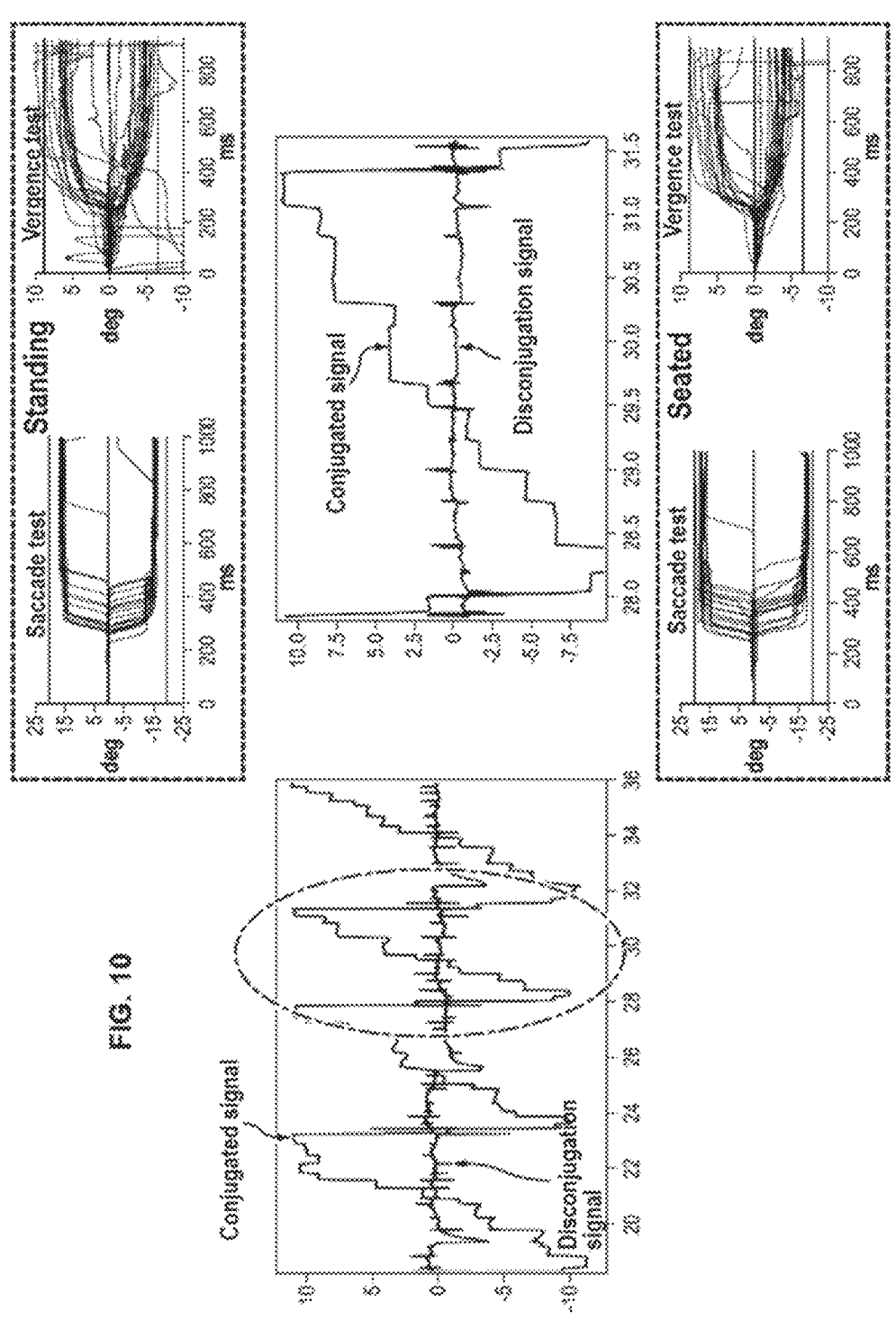
FIG. 10 illustrates a complete assessment of a dyspraxic person.

FIG. 10 illustrates a complete assessment of a person with dyspraxia. Trajectories of saccades and superimposed vergences tested in standing vs. sitting position.

For the saccade test, the upper tracings are the right-hand saccades acquired in the saccade test; the lower tracings are the left-hand saccades acquired in the same test. For the vergences test, the upper plots are the convergences and the lower plots are the divergences. As these tests are done in a standing or sitting position we can see some differences related to the positioning of the body interacting with the patterns of eye movements.

In the middle are illustrated saccades and fixations when reading four lines of text (left) or one line (right). One line is the horizontal conjugate signal (left eye+right eye/2). The saccades are the vertical lines and the fixations are the horizontal lines. The large vertical lines are the large saccades on the left to fix the next line of text. The weakest amplitude signal is disconjugation or vergence (left eye–right eye). The peaks of this signal show that at the onset of each saccade the vergence changes and then towards the offset of the saccade it returns to its initial angle. The disconjugation peaks are increased during large saccades. Display (called EYESCANART)

As a complement, the process includes a step of displaying (step E9) an image of the stimulation device on which the trajectories of eye movement are represented.

For example, one can represent on the image of the REMOBI device the superimposition of the eye trajectories according to the diodes lit according to the saccades or vergences test. Represent the trajectories either in the space of the REMOBI device or as a function of time.

For example, the text read can be represented by superimposing the trajectory followed by the eyes.

Figure 11A:
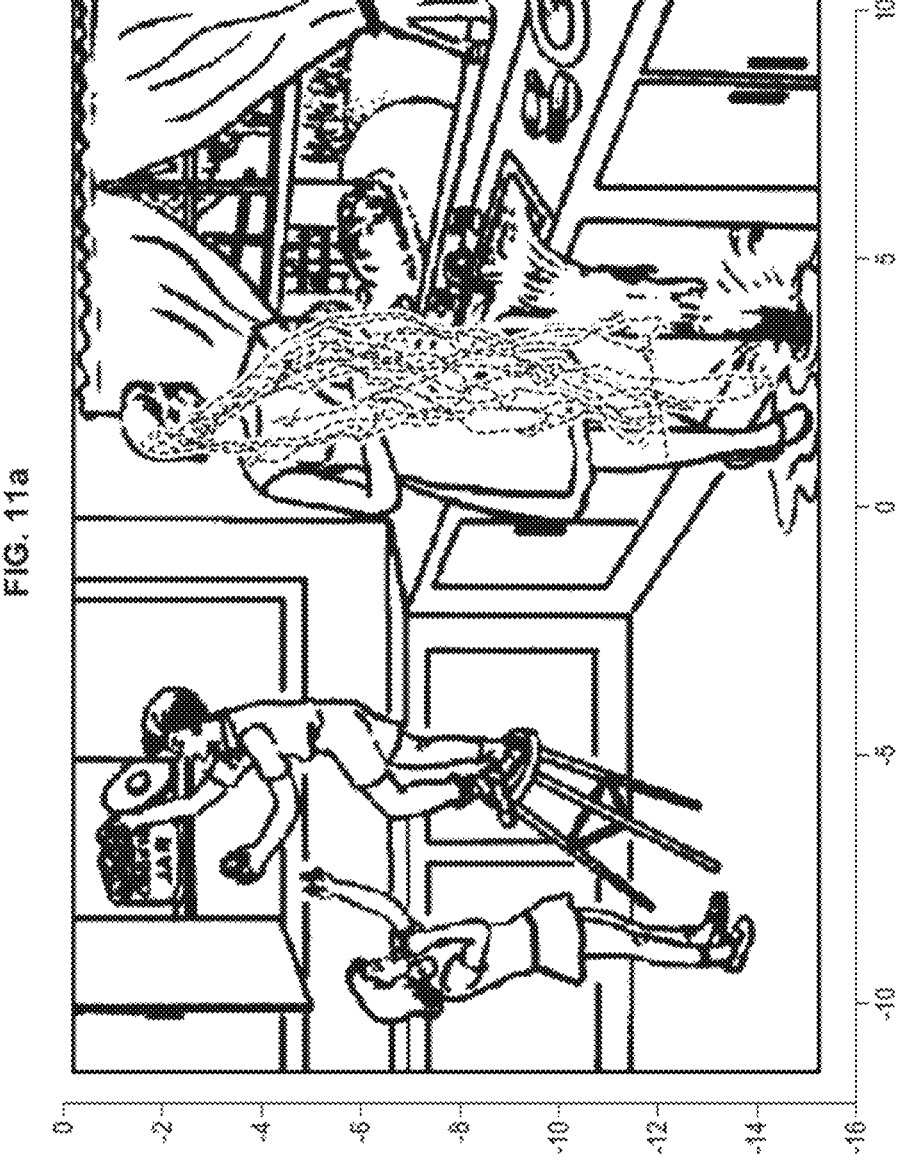
FIGS. 11a and 11b illustrate, respectively, an image used for eye movement stimulation with the superimposed eye trajectory and the trajectory followed by the eye movement.
Figure 11B:
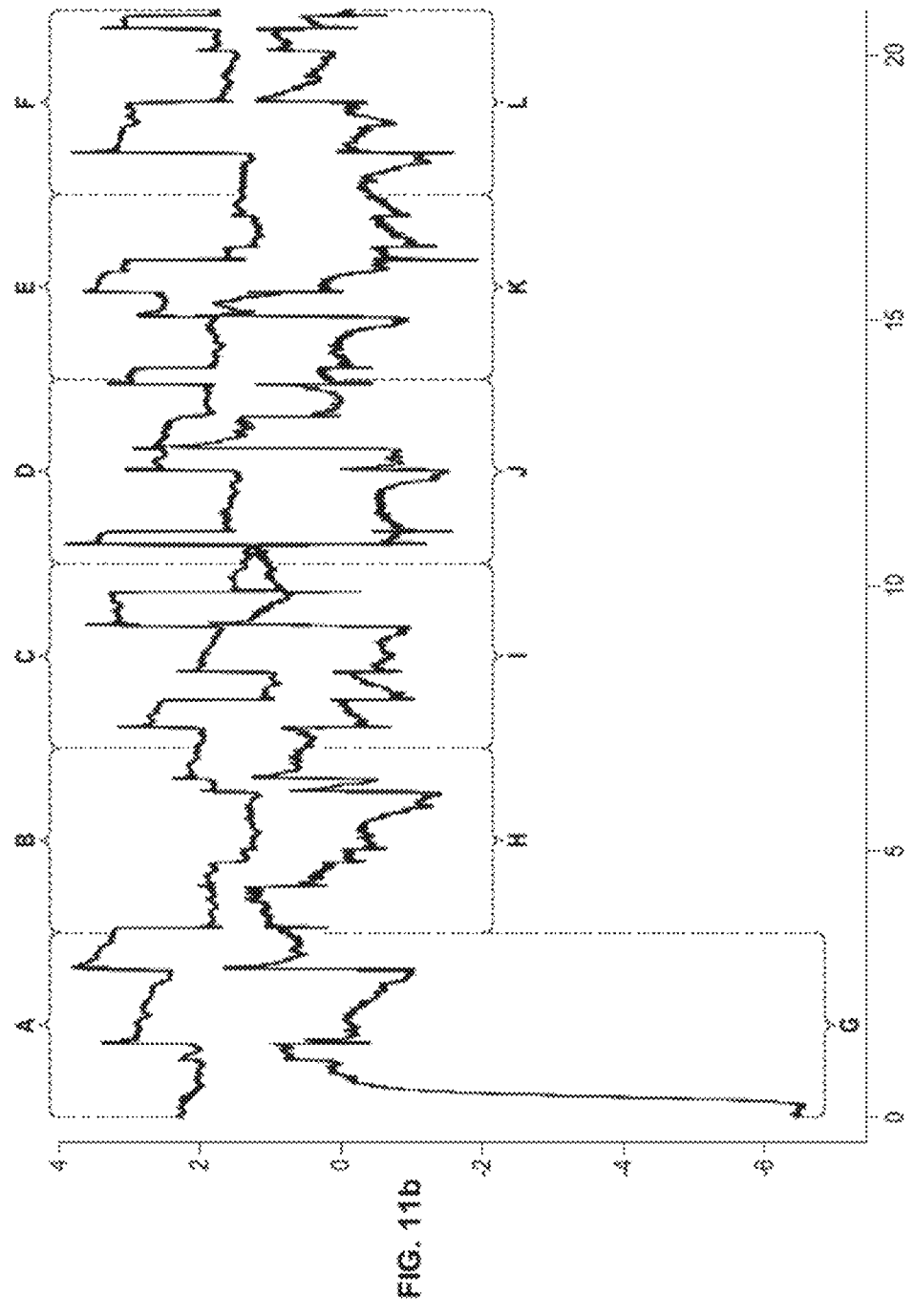

For example, one can represent the visualized image by superimposing the trajectory followed by the eyes on this image. FIG. 11a illustrates such a display and FIG. 11b illustrates the trajectory followed by the eye movement. It is this trajectory which is transposed on the image used as stimulation. The color of the trajectories changes with time every 5 sec (blue, orange, green, red, purple, brown), the operator can also produce several images separately by choosing the number of temporal segmentation desired, e.g. a pie image every 5 sec or more).

Application of the Method According to the Invention to Individuals Suffering from Learning Disorders, in Particular Dyslexic Individuals Dyslexia is a reading disorder that emerges in childhood. The primary deficit involves problems with word recognition, decoding words, and spelling, which translates into slower reading, decreased comprehension, and even difficulty writing (Raghuram, A. et al. *JAMA Ophthalmol* 136, 1089-1095, doi:10.1001/jamaophthalmol.2018.2797

(2018)). Traditionally, dyslexia has been viewed as a primary problem related to a linguistic deficit in phonological processing. The traditional therapy has therefore been educational rehabilitation and learning accommodation (e.g. use of computers for home or school work). However, there have been many studies that have shown dyslexic adolescents do have evidence of abnormal visual processing, including abnormal saccadic and vergence eye movements (Raghuram, A. et al. *JAMA Ophthalmol* 136, 1089-1095, doi:10.1001/jamaophthalmol.2018.2797 (2018); Bucci, M. P., et al. *PLOS One* 7, e33458, doi:10.1371/journal.pone.0033458 (2012); Bucci, M. P., et al. *Exp Brain Res* 188, 1-12, doi:10.1007/s00221-008-1345-5 (2008); Bucci, M. P., et al. *Graefes Arch Clin Exp Ophthalmol* 246, 417-428, doi:10.1007/s00417-007-0723-1 (2008); Jainta, S. & Kapoula, Z. *PLOS One* 6, e18694, doi:10.1371/journal.pone.0018694 (2011); Seassau, M., et al. *Front Integr Neurosci* 8, 85, doi:10.3389/fnint.2014.00085 (2014); Tiadi, A., et al. *Res Dev Disabil* 35, 3175-3181, doi:10.1016/j.ridd.2014.07.057 (2014)).

However, these studies are mainly clinically based and do not provide objective measurements of eye movements, but rather subjective evaluation of vergence and moreover using haploscopic conditions in which the two eyes are dissociated (via polarizers, prisms, or intermittent spectacles, virtual reality etc.). Other research studies using eye movement recording have identified deficits with binocular coordination during reading in dyslexics. Yet, there have been no differential studies that provide objective binocular measurements of saccades and vergences eye movements in the real space vs binocular eye movements in reading in the dyslexic population to determine if these deficits are due to a motor problem or if they are the consequence of poor reading.

Moreover, conclusions found in the prior art concerning abnormal saccades during reading for dyslexic individuals are conflicting, maybe due to the use of variable and inappropriate testing methods.

The same is true of learning disorders related to other developmental disorders, attention deficits/hyperactivity disorders, or any neurologic disorder affecting reading in which ocular motor abnormalities are clinically noticed, but it is not possible to conclude whether or not the ocular motor abnormalities are intrinsic.

The method according to the invention may thus be particularly implemented in the case of individuals suffering from learning disorders, notably dyslexic individuals.

In this case, the individual suffering from learning disorders (preferably dyslexic) is preferably submitted to at least a vergence test, a saccade test and a text reading test-optionally, the individual may also be submitted to a text reading test), and the method according to the invention then processes data from all these tests.

In addition, the inventors found that some vergence parameters obtained during a vergence test, some saccade parameters obtained during a saccade test, and some saccade parameters obtained during a text reading test, are significantly different between dyslexic and healthy individuals (see Examples 1 to 3) below.

During reading dyslexics performed many more backward saccades fixating the same word several times, the speed of reading (number of words measured per minute) was significantly lower and fixation durations were longer. Reading saccades also had abnormal velocity profile, e.g., lower average velocity, longer duration and the two eyes were poorly coordinated, showing increased disconjugacy during the saccade (see Example 1).

During vergence and saccade tests, the results showed statistically significant abnormalities in vergence and saccades. In vergence, dyslexics displayed a reduced amplitude of the 160 ms component of the convergence that follows an initial phasic component and a longer duration in the initial phasic component of divergence. In saccades, dyslexic adolescents demonstrated execution slowness' e.g. longer duration for both left and right saccades. They also showed increased deconjugate drift (convergent or divergent drifts of the eyes) in the first 80 or 160 ms of the fixation following saccades to the right, suggesting poor binocular coordination. For all movements, convergence, divergence, saccades to right or saccades to the left, the peak velocity which is achieved early during the acceleration phase of the movement, was significantly higher in dyslexics. In contrast, the average velocity was slower for dyslexics meaning that the deceleration phase of the movements was slower in dyslexics. Thus, these results indicate peculiar velocity profiles in dyslexics, particularly a slow deceleration phase in both vergence and saccades (see Example 2).

Moreover, using several distinct machine learning algorithms, they found in preliminary experiments that a general population of individuals comprising both healthy (non-dyslexic) and dyslexic individuals could be classified into two groups of non-dyslexic and dyslexic individuals based on vergence and saccade parameters measured in saccade and vergence tests using the REMOBI device with significant sensitivity and specificity, further confirming the relevance of measuring saccade and vergence parameters in saccade and vergence test as an aid for diagnosis and management of dyslexic individuals (see Example 3).

Therefore, in the case of an individual suffering from a learning disorder, in particular of a dyslexic individual, in step (E1), the person's binocular motricity is preferably stimulated by means of a binocular motricity stimulation device (21) configured to specifically stimulate vergences, saccades, and by a text reading test (22). Optionally, the person's binocular motricity may further be stimulated by an image reading test (22).

In addition, the vergence and saccade parameters calculated in step E8 by the method according to the invention are preferably selected from:

Vergence parameters during a vergence test:
duration of the initial phasic component of divergences, since these values are increased in dyslexic individuals compared to non-dyslexic individuals (see Example 2, Table 2, p-value of 0.00),
peak velocity or peak velocity of the initial phasic component (both values are equal) of convergences and divergences, since these values are increased in dyslexic individuals compared to non-dyslexic individuals (see Example 2, Table 2, p-values of 0.00 and 0.00 for convergences and divergences respectively),
average velocity of the initial phasic component of convergences and divergences, since these values are decreased in dyslexic individuals compared to non-dyslexic individuals (see Example 2, Table 2, p-values of 0.00 and 0.00 for convergences and divergences respectively),
total average velocity of convergences, since this value is decreased in dyslexic individuals compared to non-dyslexic individuals (see Example 2, Table 2, p-value of 0.03),
amplitude of the 80 ms and/or 160 ms component of convergences, since these values are decreased in dyslexic individuals compared to non-dyslexic individuals (see Example 2, Table 2, p-values of 0.00 and 0.01 for the 80 ms and 160 ms components respectively).

Saccade parameters during a saccade test:
duration of the initial phasic component of left and right saccades, since these values are increased in dyslexic individuals compared to non-dyslexic individuals (see Example 2, Table 3, p-values of 0.00 and 0.00 for left and right saccades respectively),
peak velocity or peak velocity of the initial phasic component (both values are equal) of right and left saccades, since these values are increased in dyslexic individuals compared to non-dyslexic individuals (see Example 2, Table 3, p-values of 0.00 and 0.00 for left and right saccades respectively),
average velocity of the initial phasic component of right and left saccades, since these values are decreased in dyslexic individuals compared to non-dyslexic individuals (see Example 2, Table 3, p-values of 0.00 and 0.00 for left and right saccades respectively),
post-saccadic disconjugacy parameters:
disconjugacy 80 ms after right saccades, since this value is increased in dyslexic individuals compared to non-dyslexic individuals. With respect to left saccades, disconjugacy 80 ms after left saccades shows a tendency to be increased in dyslexic individuals compared to non-dyslexic individuals (see Example 2, Table 3, p-value of 0.03).
disconjugacy 160 ms after right saccades, since this value is increased in dyslexic individuals compared to non-dyslexic individuals. With respect to left saccades, disconjugacy 160 ms after left saccades also shows a tendency to be increased in dyslexic individuals compared to non-dyslexic individuals (see Example 2, Table 3, p-value of 0.02).

Saccade parameters during a text reading test:
average velocity of saccades during reading,
disconjugacy 80 ms and/or 160 ms after right saccades during reading, and
number or proportion of regression saccades, and reading speed (number of words per minute).

In particular, velocity abnormalities have been observed in dyslexic individuals for both vergence and saccades during vergence and saccade tests, as well as increased disconjugacy 80 ms to 160 ms (such as 80 ms or 160 ms) after right saccades. Notably, it should be noted that, despite non-deficient and even somewhat improved peak velocity (corresponding to a faster initial eye movement), dyslexic are characterized by a decreased and thus deficient average velocity and thus an increased duration of vergences and saccades during vergence and saccade tests, corresponding of a slowing of the vergence or saccade eye movements after an initial normal or even improved start. This slowing of eyes movement after quick initiation of vergences and saccades, resulting in decreased average velocity and increased duration of vergences and saccades, appears to be characteristic of dyslexic individuals.

During saccade test, dyslexic is also characterized by increased disconjugacy 80 ms or 160 ms after right saccades.

Therefore, when the individual is a dyslexic individual, based on the vergence and saccade tests, parameters calculated in step E8 by the method according to the invention based on a saccade and a vergence test are preferably selected from:

at least one vergence velocity or duration parameter, preferably average velocity or duration of convergences and/or divergences (preferably both convergences and divergences), at least one saccade velocity or duration parameter, preferably average velocity or duration of left and/or right saccades (preferably both left and right saccades), at least one post-saccadic disconjugacy parameter, preferably disconjugacy 80 ms or 160 ms after right saccades, or any combination thereof.

Parameters calculated in step E8 by the method according to the invention based on a saccade and a vergence test may notably comprise at least one vergence velocity or duration parameter, at least one saccade velocity or duration parameter, and at least one post-saccadic disconjugacy parameter obtained in vergence and saccade tests. However, the inventors also found that abnormalities in vergence velocity parameters and in post-saccadic disconjugacy parameter were correlated, so that both types of parameters do not need to be calculated simultaneously. For instance, based on the vergence and saccade tests, parameters calculated in step E8 by the method according to the invention may notably comprise only:

at least one vergence velocity parameter and at least one saccade velocity parameter, or at least one vergence duration parameter and at least one saccade duration parameter, or at least one saccade velocity parameter, and at least one post-saccadic disconjugacy parameter.

Particularly preferred combinations of parameters to be calculated based on the vergence and saccade tests include at least:

i) average velocity of convergences, divergences, and left and right saccades, ii) duration of convergences, divergences, and left and right saccades, iii) disconjugacy 80 ms and/or 160 ms after right and left saccades, or after right saccades only, iv) combination of i) and ii), v) combination of i) and iii), vi) combination of ii) and iii), and vii) combination of i), ii) and iii).

When integrating a vergence test, a saccade test and a text reading test, preferred combinations of parameters to be calculated in step E8 of the method according to the invention comprise:

a preferred combination of vergence and saccade parameters during vergence and saccade tests respectively, in particular combinations i) to vii) disclosed above, and/ or (preferably and)

preferred parameters calculated based on a text reading test (average velocity of saccades, disconjugacy 80 ms and/or 160 ms after right saccades, number or proportion of regression saccades, and reading speed).

The inventors also found that saccade parameters during a saccade test, vergence parameters during a vergence test and saccade and other parameters during a text reading test are also of interest for individuals suffering from other learning disorders (see Example 3), such as:

dyslexia, a reading disorder that emerges in childhood, involving problems with word recognition, decoding words, and spelling, which translates into slower reading, decreased comprehension, and even difficulty in writing;

dyspraxia, also referred to as developmental co-ordination disorder, a condition affecting physical co-ordination and causing a child to perform less well than expected in daily activities for their age, and appear to move clumsily;

dysphasia, a type of disorder where a person has difficulties comprehending language or speaking due to some type of damage in the parts of the brain responsible for communication. The symptoms of dysphasia vary based on the region of the brain that was damaged. There are different regions responsible for understanding language, speaking, reading, and writing, though typically they are found in the left side of the brain;

dyscalculia, involving problems with mathematics and difficulties with problem-solving;

dysgraphia, involving problems with spelling, written expression, or handwriting;

attention-deficit/hyperactivity disorder (ADHD), which is characterized by excessive activity, short attention span and impaired inhibitory control.

Application of the Method According to the Invention to Individuals Suffering from Vertigo According to clinical studies binocular motor coordination problems exist systematically in patients with vertigo. Vergence eye movements are the ones that concern the correct movement of one eye relative to the other so that the angle of the optic axes is adjusted appropriately according to the depth we are fixating (increase the convergence angle for fixating a near target, decrease it for fixating a far target). During saccades (left right eye movements or up down, the eyes should move the same way, and no vergence should be involved. However, vergence errors occur during saccades that are small physiologically in healthy persons, but could be substantial in patients with vertigo. Vergence eye movements and vergence errors during saccades enable to characterize the quality of binocular motor coordination and they are related. Indeed, vergence errors during saccades are large when the vergence eye movements are poor (see Kapoula Z, Morize A, Daniel F, Jonqua F, Orssaud C, Brémond-Gignac D. Objective Evaluation of Vergence Disorders and a Research-Based Novel Method for Vergence Rehabilitation. Transl Vis Sci Technol. 2016 Mar. 11; 5(2):8; and Morize A, Brémond-Gignac D, Daniel F, Kapoula Z. Effects of Pure Vergence Training on Initiation and Binocular Coordination of Saccades. Invest Ophthalmol Vis Sci. 2017 Jan. 1; 58(1): 329-342).

In vertigo patients of organic origin vergence is poor (see Kapoula Z et al. PLOS One. 2013 Jun. 18; 8(6):e66652).

In children with vertigo symptoms vergence is poor even though there is no organic vestibular cause (Bucci M P et al. J Neurol. 2004 February; 251(2):204-13; Bucci M P et al. Exp Brain Res. 2004 August; 157(3):286-95; Bucci M P et al. Vision Res. 2006 October; 46(21):3594-602).

Thus, vergence disorder could cause vertigo and reciprocally vestibular pathology could cause vergence disorder and maintain vertigo symptoms.

In this context, there is a need for new clinical management protocols for individuals suffering from vertigo, that would take into account the symbiotic interaction between vergence and vestibular function.

In the context of the present invention, the inventors found that individual suffering from vertigo perform differently in vergence tests performed using REMOBI device (a binocular motor stimulation device configured to specifically and physically stimulate vergences and saccades and comprising visual or audiovisual targets placed in real space at eccentricities and depths of a surface) in single step paradigm, when the vergence tests is performed in seated or standing position (see Example 1). They further found that, after 4 rehabilitation sessions using the REMOBI device in double step paradigm alternating seated and standing position, vergence performances of more than half of the individual with vertigo (8/14) were improved. In particular, decrease in latency, increase in amplitude or velocity, reduction in variability or a better coupling between saccade and vergence was observed, in particular in standing position (see Example 1). Moreover, patients reported a clear benefit in their navigation and space relation. The benefits were particularly prevalent in patients with vestibular asthenopia and Meniere's disease (see Example 5).

Therefore, in the case of an individual suffering from vertigo, in particular vertigo from functional origin and notably vestibular asthenopia and Meniere's disease, in step (E1), the person's binocular motricity is preferably stimulated by means of a binocular motricity stimulation device (21) configured to specifically stimulate vergences (FIG. 2a), and optionally also saccades (FIG. 2b) and/or combined movements (FIG. 2c), in seated and in standing (orthostatic quiet stance position) position.

In addition, the vergence parameters calculated in step E8 by the method according to the invention preferably comprise latency and total amplitude of convergences and divergences during vergence tests performed in seated and in standing position, and optionally other binocular coordination parameters.

The following examples merely intend to illustrate the present invention.

EXAMPLES

Example 1: Detection of Vergence and Saccade Abnormalities in Dyslexic Individuals During Reading Using the Method According to the Invention Dyslexic individuals are known to have troubles when reading. Here, dyslexic and non-dyslexic individuals were submitted to a reading test and vergence and saccade parameters were measured during reading.

Patients, Materials and Methods 47 dyslexic (18 female, 29 male; mean age 15.47) and 44 non-dyslexic individuals (22 female, 22 male; mean age 14.77) were recruited from schools in Paris (see Example 2 for full description of subjects).

For the reading test, individuals were seated, and their eyes' movements were recorded using a head-mounted video-oculography device, Pupil Core, enabling binocular recording at 220 Hz per eye (Pupil Labs, Berlin) during reading of the text "L'Alouette", which has no sense (Cavalli E, Colé P, Leloup G, Poracchia-George F, Sprenger-Charolles L, El Ahmadi A. Screening for Dyslexia in French-Speaking University Students: An Evaluation of the Detection Accuracy of the Alouette Test. J Learn Disabil. 2018 May/June; 51(3):268-282).

Based on these measurements, vergence and saccades curves were generated and vergence and saccades parameters measured using the AIDEAL software, which performs the method according to the invention.

Results

Reading results are presented in Table 1 below:

TABLE 1

| Reading results of dyslexic versus non-dyslexic individuals. | | | |
| --- | --- | --- | --- |
| Reading parameter | Dyslexic individual | Healthy individual | P value |
| Right saccade amplitude | 1.92 | 2.26 | 0.000 |
| Right saccades Duration | 81.49 | 61.80 | 0.001 |
| Right saccades Peak Velocity | 93.98 | 85.29 | 0.005 |
| Right Average Velocity | 43.25 | 63.51 | 0.000 |
| Right saccades post-saccadic drift (80 ms) | 0.50 | 0.49 | 0.915 |
| Right saccades post-saccadic drift (160 ms) | 0.80 | 0.72 | 0.640 |
| Disconjugacy of right saccades | 1.44 | 0.97 | 0.037 |
| (Number of Right Saccades-Number of Left Saccades)/ Number of Right Saccades | 0.5371 | 0.6644 | 0.014 |
| % of saccades of regression | 47% | 30% | |
| Reading Mistakes per word | 0.0819 | 0.0319 | 0.000 |
| Reading speed (words per Minute) | 110.86 | 126.35 | 0.000 |

In dyslexics, the reading speed (number of words read per minute) is slower (110.86 in dyslexic on average, versus 126.35 in healthy individuals, p=0.000), the amplitude of the saccades is smaller (1.92 in dyslexic on average, versus 2.26 in healthy individuals, p=0.000), the reading mistakes per word were higher (0.0819 in dyslexic on average, versus 0.0319 in healthy individuals, p=0.000), and a greater proportion of regression saccades (saccades in back, to the left, 47% in dyslexic on average, versus 30% in healthy individuals) were observed. These oculomotor abnormalities are the consequence of the difficulty of reading in large part.

Reading saccades also had abnormal velocity profile, e.g., lower average velocity (43.25 in dyslexic on average, versus 63.51 in healthy individuals, p=0.000), longer duration (81.49 in dyslexic on average, versus 61.80 in healthy individuals, p=0.001) and their eyes were poorly coordinated, showing increased disconjugacy during the saccade (1.44 in dyslexic on average, versus 0.97 in healthy individuals, p=0.037).

Figure 12:
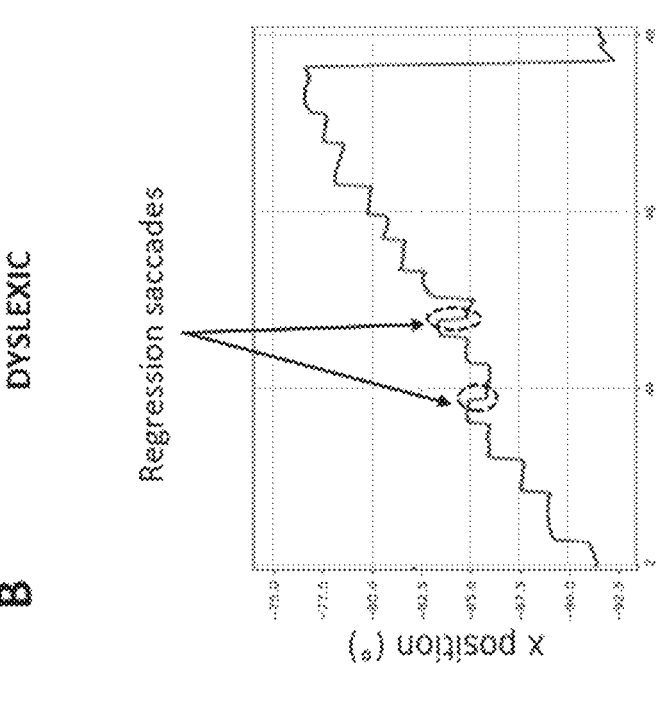
FIG. 12. Exemplary trajectories of the eye movements of a healthy (non-dyslexic, A) and a dyslexic (B) individual during reading of one line of text. In this figure, on the x-axis we have time; in y the conjugate signal of both eyes in degrees, showing the succession of saccades to the right followed by fixations fixing the words one after the other, then the large saccade to the left to start reading the next line. Regression saccades are further present for the dyslexic individual.
Figure 13:
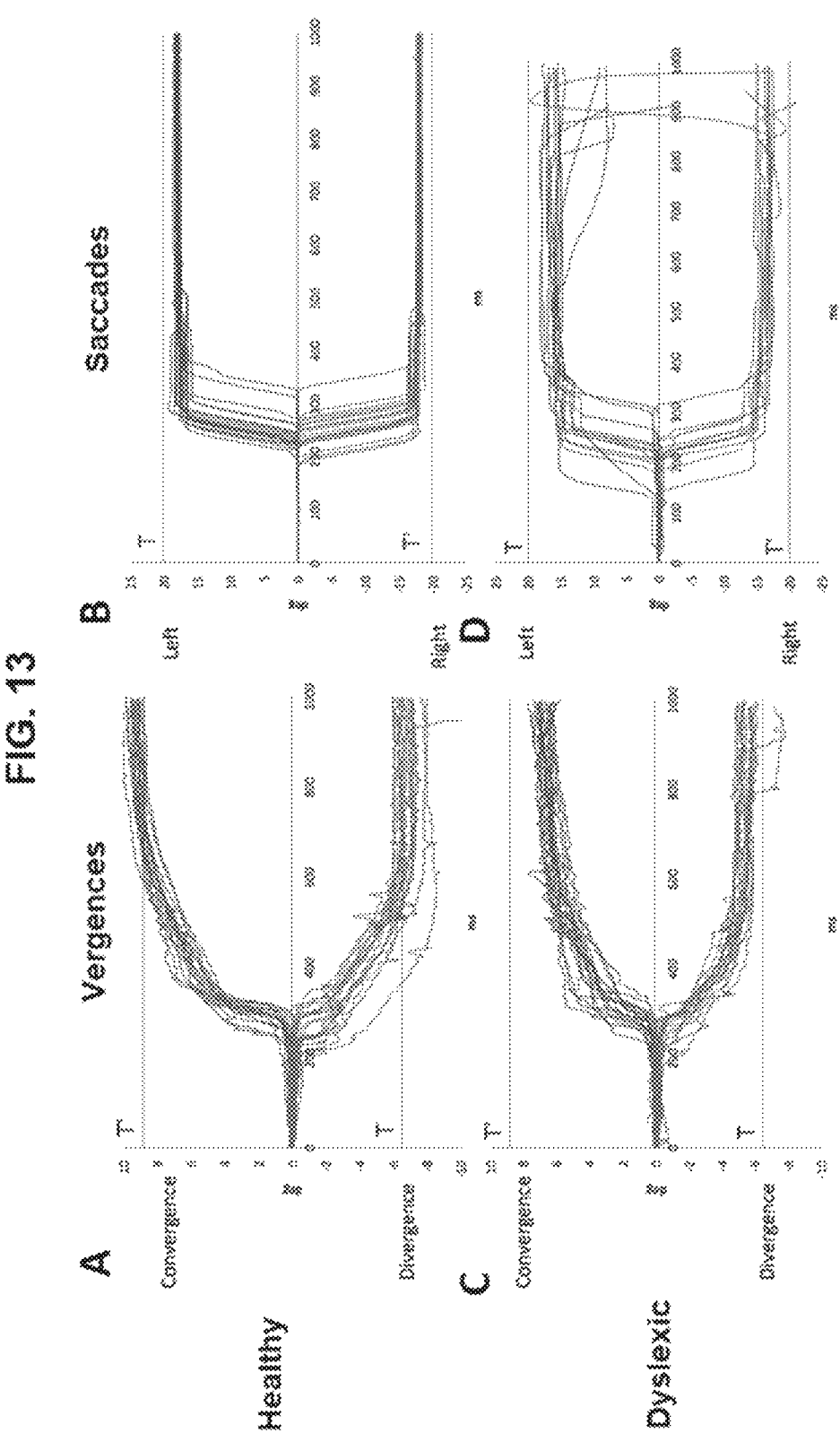
FIG. 13. Example of Individual Vergence and Saccade Trials in healthy and dyslexic individuals. Trajectories of vergence and saccades in an individual healthy control (A,B) and dyslexic (C,D) individual in a vergence and a saccade test. Despite initiating vergence movements quickly towards the target (grey line marked T or T' above and below the x-axis), the dyslexic individual takes longer to reach the vergence target (indeed, longer than measured). Similar difficulties can be seen in the saccade trial (B,D).

FIG. 12 shows exemplary trajectories of the eyes movements of a healthy (non-dyslexic, FIG. 12A) and a dyslexic (FIG. 12B) individual during reading of one line of text.

FIG. 12A illustrates the exploration of the eyes of a reader who does not suffer from any pathology. In this figure, on the x-axis we have time; in y the conjugate signal of both eyes in degrees, showing the succession of saccades to the right followed by fixations fixing the words one after the other, then the large saccade to the left to start reading the next line. As may be seen, the exploration of the healthy individual is quite regular, and does not comprise many regression saccades.

In contrast, in FIG. 12B presenting the same curve for a dyslexic individual, the progression of the eyes is not so regular and comprises regression saccades.

Conclusions

The above data show that dyslexic individuals have troubles when reading, as well as saccade abnormalities.

Example 2: Detection of Intrinsic Vergence and Saccade Abnormalities in Dyslexic Individuals While data presented in Example 1 show that dyslexic individuals have vergence and saccade abnormalities during reading, such data does not permit to conclude whether ocular motor abnormalities during reading are or not at least partly due to intrinsic ocular motor abnormalities.

To be able to draw such conclusion, it is necessary to perform further ocular motor tests, in conditions where vergence and saccades are physically stimulated, thus permitting measure of intrinsic ocular motor coordination.

Such tests have been performed in dyslexic versus non-dyslexic individuals.

Patients, Materials and Methods

Participants 47 dyslexic adolescents (18 female, 29 male; mean age 15.47) and 44 non-dyslexic adolescents (22 female, 22 male; mean age 14.77) were recruited from schools in Paris. Dyslexic adolescents were selected from a school targeted towards dyslexic adolescents based on physician documentation of a dyslexia diagnosis in their school records. Both dyslexic and non-dyslexic adolescents had no known neurologic or psychiatric abnormalities. Healthy controls had no known neurological or psychiatric abnormalities, no history of reading difficulty, no visual impairment, or difficulty with near vision. The investigation adhered to the principles of the Declaration of Helsinki and was approved by our Institutional Human Experimentation Committee (CPP CNRS 18 011). Written consent was obtained from the adolescents and/or their parents after they were given an explanation about the experimental procedure.

Clinical Characteristics of the Participants

Adolescents were asked to rate how much they liked doing certain activities (reading, watching movies, going to museums, etc.) on a scale from one to ten, where one meant they did not like doing the activity at all, and ten meant they loved doing the activity. They were also asked how many hours they spent watching TV, using the computer, playing video games, and on their telephone. They also responded to the Convergence Insufficiency Symptom Survey (CISS), a validated questionnaire for quantifying vergence problems in children and adults (Rouse, M. et al. Validity of the convergence insufficiency symptom survey: a confirmatory study. *Optom Vis Sci* 86, 357-363, doi:10.1097/OPX.0b013e3181989252 (2009)). Their stereoscopic depth discrimination was measured using the Titmus Test (Titmus Stereo Fly Test, Stereo Optical, Essilor Instruments).

Eye Movement Recording Device

For each adolescent, eye movements were recorded binocularly with a head-mounted video-oculography device, Pupil Core, enabling binocular recording at 220 Hz per eye (Pupil Labs, Berlin).

Calibration of the Pupil Labs Device

The standard Pupil Labs calibration (Pupil Capture) was applied using a target that was presented at viewing distance of 1 m. The individual fixated on the center of the target and moved their head rightward, downward, leftward and upward at their own pace. They then repeated the sequence (Kassner, M., Patera, W. & Bulling, A. in *Proceedings of the 2014 ACM international joint conference on pervasive and ubiquitous computing: Adjunct publication.* 1151-1160).

Ocular Motor Tests

Adolescents were asked to sit in front of a horizontal visual-acoustic REMOBI device (see U.S. Pat. No. 8,851, 669 and WO2011073288). The device was placed at eye level, so that the first arc of LEDs was 20 cm from their eyes. Each child is instructed to carefully fixate quickly and accurately on the moving LED, to not attempt to predict a pattern of motion, and to keep their head still during the 2-minute test.

Oculomotor tests were performed in mesopic light conditions. The red LED stimuli were displayed at different distances, laterally or in depth, always in the horizontal plane (0°, FIGS. 1B and 1C). LED characteristics were: nominal frequency 626 nm, intensity 180 mCd, and diameter 3 mm. Adjacent to each LED was embedded a buzzer with the following characteristics: nominal frequency approximately 2048 Hz, sound pressure level 75 dB, diameter 12 mm.

Vergence Test

For each trial the fixation LED (0°) light up at 40 cm, creating a required vergence angle of 9° for a period varying from 1200 ms to 1800 ms. (see FIGS. 1A and 1C) It was followed randomly by the target LED during 2000 ms, appearing always at the central axis (0°) either at 20 cm (calling for a convergence movement of 8°, i.e. from 9° to 17°) or 150 cm (calling for a divergence movement of 7°, i.e. from 9° to 2). The test contained 40 trials (20 trials of convergence, 20 of divergence, pseudo-randomly interleaved) in an overlap paradigm: after an overlap period of 200 ms following the lighting of the target LED, the fixation LED switched off.

Saccade Test

Each trial started with the fixation central LED lighting at 40 cm from the individual for a randomized period ranging from 1200 ms to 1800 ms; it was followed by the lighting of the saccade target LED for 2000 ms at 20° of eccentricity, randomly chosen on the left or on the right. (FIGS. 1A and 1B) There were 40 trials (20 left, 20 right, pseudo-randomly interleaved) in an overlap paradigm.

Data Analysis

Data recorded with the Pupil Labs eye tracker were analyzed with AIDEAL, software developed in the IRIS laboratory (see French patent application filed on May 14, 2020 under number FR2004768, DSO2020003510, 2 mars 2020). The vergence signal was derived by calculating the difference between the two eyes from the individual calibrated eye position signals (i.e., left eye-right eye). The beginning and end of the vergence movements were defined as the time point when the eye velocity exceeded or dropped below 5°/s: these criteria are standard and were applied automatically by the AIDEAL software; the program estimated the initial phasic component as the amplitude between these two initial points. It also calculated the amplitude change during the subsequent 80 ms and 160 ms. The total amplitude was calculated as the sum of the amplitude of the initial phasic component plus the 160 ms component. The total duration was calculated as the duration of the phasic component plus the subsequent 160 ms.

For saccade analysis, AIDEAL treated the conjugate signal, e.g. the L+R eye position/2.

The onset and the offset of the saccade were defined as the time points where the velocity went above or below 10% of the peak velocity; practically, this corresponded to values above or below 40°/s (as the peak velocity of 20° saccades is typically above 400°/s). The total average velocity was defined as the ratio of total amplitude in degrees divided by time in seconds. To evaluate binocular coordination of saccades, or the disconjugacy during saccadic movements, the difference in amplitude between the left and the right eye signal was calculated. The disconjugate drift, or the difference in drift amplitude during the first 80 or 160 ms of fixation, was calculated. These calculations are standard and have been used in previous experiments (Kapoula, Z. et al. *Transl Vis Sci Technol* 5, 8, doi:10.1167/tvst.5.2.8 (2016); Morize, A., et al. *Invest Ophthalmol Vis Sci* 58, 329-342, doi:10.1167/iovs. 16-19837 (2017)).

Trials with blinks or other artifacts were discarded automatically by AIDEAL. For each adolescent (dyslexic and non-dyslexic) the number of saccades and vergence movements measured in the fixation tasks were counted. The percentage of movements rejected were 0% for vergence and 9% for saccades in dyslexic children and 2% for vergence and 3% for saccades in healthy children.

Statistical Analysis

As the measured eye movements data were not normally distributed as determined by the Shapiro-Wilk test, the non-parametric Mann-Whitney U test was utilized for means comparison. All hypothesis testing was two-sided and p-values of $<0.05$ was considered statistically significant. All analyses were performed using SPSS version 25 (IBM Corp. Released 2017. IBM SPSS Statistics for Windows, Version 25.0. Armonk, NY: IBM Corp.).

Results

Participant's Characteristics

Dyslexic adolescents reported spending more hours on the computer per week than non-dyslexic adolescents (30.80 vs 13.54, p=0.000). They also reported liking to read less (4.78 vs 6.57, p=0.011) and liking to go to theaters and films more than non-dyslexic adolescents (8.12 vs 7.24, p=0.036).

Clinical Visual Examination

Dyslexic adolescents had a lower score on the stereoscopic vision test (57.50 vs 25.86, p $<0.001$), indicating difficulty in perceiving depth with very high spatial resolution. They also exhibited higher scores on the Convergence Insufficiency Symptom Survey (24.40 vs 17.68, p=0.008), indicating symptomatic vergence disorders. A score greater than 21 indicates a symptomatic vergence disorder (Rouse, M. et al. *Optom Vis Sci* 86, 357-363, doi:10.1097/OPX.0b013e3181989252 (2009)).

Eye Movement Results

Vergence in Dyslexics Vs Non-Dyslexics

In terms of the initial phasic component of vergence (the time when velocity exceeds or drops below 5°/s), dyslexic adolescents exhibited a longer duration for divergence (42.61 ms, SD 21.02 ms vs 29.64 ms, SD 9.92 ms; p<0.00, p values are all truncated to 2 decimals). They also exhibited an increased peak velocity in both divergence and convergence, meaning their speed during the initial acceleration component of the vergence movement was higher than non-dyslexics (Divergence: 90.68°/s, SD 60.32°/s vs 61.95°/s, SD 76.63°/s; p<0.00; Convergence: 99.33°/s, SD 63.45°/s vs 70.79°/s, SD 42.68°/s; p<0.00). Yet, dyslexics displayed a decreased average velocity during this initial phasic component in both divergence and convergence (Divergence: 32.65°/s, SD 11.19°/s vs 41.32°/s, SD 36.89; p<0.00; Convergence: 35.28°/s, SD 14.20°/s vs 46.00°/s, SD 15.82; p<0.00). Therefore, despite demonstrating a higher peak velocity during the acceleration phase, the subsequent deceleration phase was significantly slower. When examining the total average velocity (the initial phasic component plus the subsequent 160 ms), dyslexics displayed a significantly lower total average velocity for convergence (0.016°/s, SD 0.007 vs 0.194°/s, SD 0.008, p=0.03), but not during divergence (0.013°/s, SD 0.005 vs 0.015°/s, SD 0.005; p=0.29).

In terms of amplitude in the initial phasic component of vergence, there was no significant difference between dyslexics and non-dyslexics (Divergence: 1.47°, SD 0.97 vs 1.22°, SD 0.65; p=0.25; Convergence: 2.18°, SD 1.52 vs 2.18°, SD 1.35; p=0.53). Yet, the later phases of vergence measured during the subsequent 80 and 160 ms were both significantly smaller. For convergence only, dyslexic adolescents exhibited decreased amplitude in both the 80 and 160 ms phases of movement (80 ms: 0.85°, SD 0.43 vs 1.12°, SD 0.47, p<0.00; 160 ms 1.52°, SD 0.71 vs 1.95°, SD 0.87, p=0.01), and divergence movements also trended towards decreased values for the dyslexic population (see Table 2 below).

TABLE 2

Means and standard deviations of vergence parameters in dyslexic and non-dyslexic adolescents. P values are all truncated to 2 decimals. Variables with significant differences between the two populations (p < 0.05) are bolded.

|  | Dyslexic | | Non-dyslexic | | p-value |
| --- | --- | --- | --- | --- | --- |
|  | Average | SD | Average | SD | |
| Divergence Initial Amplitude (deg) | 1.47 | 0.97 | 1.22 | 0.65 | 0.25 |
| Convergence Initial Amplitude (deg) | 2.18 | 1.52 | 2.18 | 1.35 | 0.53 |
| Divergence Total Amplitude (deg) | 2.76 | 1.13 | 2.78 | 1.06 | 0.71 |
| Convergence Total Amplitude (deg) | 3.70 | 1.91 | 4.13 | 1.84 | 0.23 |
| Divergence Latency (ms) | 334.02 | 62.50 | 334.27 | 69.18 | 0.96 |
| Convergence Latency (ms) | 336.51 | 68.20 | 314.29 | 75.10 | 0.21 |
| Divergence Duration (ms) | 42.61 | 21.02 | 29.64 | 9.92 | 0.00 |
| Convergence Duration (ms) | 60.71 | 30.97 | 49.50 | 24.39 | 0.09 |
| Divergence Peak Velocity (deg/sec) | 90.68 | 60.32 | 61.95 | 76.63 | 0.00 |
| Convergence Peak Velocity (deg/sec) | 99.33 | 63.45 | 70.79 | 42.68 | 0.00 |
| Divergence Average Velocity (deg/sec) | 32.65 | 11.19 | 41.32 | 36.89 | 0.00 |
| Convergence Average Velocity (deg/sec) | 35.28 | 14.20 | 46.00 | 15.82 | 0.00 |
| Divergence Total Velocity (deg/sec) | 13.43 | 4.46 | 14.53 | 5.07 | 0.29 |
| Convergence Total Velocity (deg/sec) | 16.21 | 6.73 | 19.41 | 7.72 | 0.03 |
| Divergence amplitude 80 ms after phasic component (deg) | 0.73 | 0.30 | 0.89 | 0.80 | 0.06 |
| Convergence Amplitude 80ms after phasic component (deg) | 0.85 | 0.43 | 1.12 | 0.47 | 0.00 |
| Divergence amplitude 160 ms after phasic component (deg) | 1.29 | 0.59 | 1.56 | 0.68 | 0.06 |
| Convergence amplitude 160 ms after phasic component (deg) | 1.52 | 0.71 | 1.95 | 0.87 | 0.01 |

In terms of total amplitude (adding the initial phase and the amplitude over the subsequent 160 ms), there was no statistically significant difference between the two populations (Divergence: 2.76°, SD 1.13 vs 2.78°, SD 1.06; p=0.710; Convergence: 3.70°, SD 1.91 vs 4.13°, SD 1.84; p=0.23).

In summary, careful analysis of the vergence trajectory over different periods reveals abnormal vergence execution in dyslexics, e.g. a higher peak velocity but abnormal slowing of the velocity during the deceleration phase. Amplitude analysis reveals decreased values during the later phases of convergence (80 and 160 ms).

Saccades in Dyslexics Vs Nondyslexics

There was also a significant difference in several parameters in saccades between dyslexic and non-dyslexic adolescents. For saccades either to the left or to the right, during the initial phase of the movement dyslexic adolescents displayed an increased duration, meaning it took them longer to reach the target (Left: 70.98 ms, SD 14.14 ms vs 64.34 ms, SD 11.55 ms; p<0.00; Right: 68.86 ms, SD 12.01 ms vs 63.15 ms, SD 8.57; p<0.00, p values are all truncated to 2 decimals). Similar to vergence, they also exhibited an increased peak velocity during the initial phase of the movement (Left: 387.89°/s, SD 160.03°/s vs 280.07°/s, SD 95.76°/s; p<0.00; Right: 365.06°/s, SD 159.20°/s vs 277.18°/s, SD 97.03°/s; p<0.00) but a decreased average velocity (Left: 200.56°/s, SD 75.15°/s vs 259.83°/s, SD 61.05°/s; p<0.00; Right: 197.19°/s, SD 80.00°/s vs 252.71°/s, SD 60.37°/s; p<0.00), meaning that, like in vergence, their initial movement towards the target is faster than normal controls, but the subsequent deceleration phase is slowed substantially.

To evaluate binocular coordination during fixation after the saccade, we measured by the disconjugacy of the drifts during the first 80 and 160 ms following the end of the saccade, as these two periods were chosen to represent the two time constants of the ocular movement: the extraocular muscle movement and the stabilization of the eye after the saccade (DA, R., Z, K. & HP, G. in From neuron to action Ch. Holding the eye still after a saccade, 89-96 (Springer, 1990)). For saccades to the right only, dyslexics had an increased disconjugacy during both phases of fixation (80 ms: 0.98, SD 0.96 vs 0.63, SD 0.35, p=0.03; 160 ms: 1.24, SD 1.07 vs 0.80, SD 0.80, p=0.02). Dyslexics displayed an increased disconjugate drift in both phases of fixation for saccades to the left but this observation did not reach statistical significance (see Table 3 below).

TABLE 3

Saccadic parameters in dyslexic and non-dyslexic adolescents. P values are all truncated to 2 decimals. Variables with significant differences between the two populations (p < 0.05) are bolded.

| | Dyslexic | | Non-Dyslexic | | P- |
| --- | --- | --- | --- | --- | --- |
| | Average | SD | Average | SD | Value |
| Left Amplitude (deg) | 16.76 | 3.43 | 16.685 | 1.95 | 0.64 |
| Right Amplitude (deg) | 16.24 | 1.52 | 16.83 | 2.03 | 0.22 |
| Left Total Amplitude (deg) | 17.11 | 1.56 | 17.44 | 2.11 | 0.61 |
| Right Total Amplitude (deg) | 16.92 | 1.37 | 17.64 | 2.23 | 0.25 |
| Left Latency (ms) | 250.13 | 49.09 | 244.72 | 53.75 | 0.12 |
| Right Latency (ms) | 273.34 | 65.61 | 265.56 | 63.09 | 0.36 |
| Left Duration (ms) | 70.98 | 14.14 | 64.34 | 11.55 | 0.00 |
| Right Duration (ms) | 68.86 | 12.01 | 63.15 | 8.57 | 0.00 |
| Left Peak Velocity (deg/sec) | 387.89 | 160.03 | 280.07 | 95.76 | 0.00 |
| Right Peak Velocity (deg/sec) | 365.06 | 159.20 | 277.18 | 97.03 | 0.00 |
| Left Average Velocity (deg/sec) | 200.56 | 75.15 | 259.83 | 61.05 | 0.00 |

TABLE 3-continued

Saccadic parameters in dyslexic and non-dyslexic adolescents. P values are all truncated to 2 decimals. Variables with significant differences between the two populations (p < 0.05) are bolded.

| | Dyslexic | | Non-Dyslexic | | P- |
| --- | --- | --- | --- | --- | --- |
| | Average | SD | Average | SD | Value |
| Right Average Velocity (deg/sec) | 197.19 | 80.00 | 252.71 | 60.37 | 0.00 |
| Left Total Velocity (deg/sec) | 72.08 | 14.76 | 78.22 | 9.63 | 0.09 |
| Right Total Velocity (deg/sec) | 74.14 | 7.28 | 78.86 | 9.49 | 0.04 |
| Left Fixation Disconjugacy 80 ms after saccade (deg) | 0.77 | 0.46 | 0.62 | 0.43 | 0.07 |
| Right Fixation Disconjugacy 80 ms after saccade (deg) | 0.98 | 0.96 | 0.63 | 0.35 | 0.03 |
| Left Fixation Disconjugacy 160 ms after saccade (deg) | 0.97 | 0.64 | 0.74 | 0.46 | 0.08 |
| Right Fixation Disconjugacy 160 ms after saccade (deg) | 1.24 | 1.07 | 0.80 | 0.43 | 0.02 |
| Left Disconjugacy During Saccade (deg) | 2.85 | 1.61 | 2.82 | 1.53 | 0.97 |
| Right Disconjugacy During Saccade (deg) | 2.55 | 1.78 | 2.34 | 1.16 | 0.90 |

The binocular coordination during the saccade (i.e. the amplitude difference between left and right eye) was not significantly different between the two groups (see Table 3). To determine the relationship between vergence and saccades, we examined the cross-correlation between average velocity and the disconjugate drift after the saccade at 80 ms and 160 ms. For all adolescents, (dyslexic and non-dyslexic) we found the average velocity during vergence is significantly negatively correlated with the deconjugate drift following saccades to the left in the first 80 ms (Convergence: r=−0.223; p=0.044; Divergence: r=−0.296; p=0.007) and in the 160 ms following the saccade (Convergence: r=−0.340; p=0.002; Divergence: r=−0.402; p=0.000). Therefore, the lower the velocity was during vergence, the higher the deconjugate drift of the saccades.

When looking at dyslexic and non-dyslexic groups individually, a significant negative correlation between average velocity and the disconjugate drift in the following 160 ms after the saccade was found for dyslexics only during convergence following left saccades (r=−0.355; p=0.027). Correlations for drifts following rightward saccades did not reach significance. Correlations for healthy children only did not reach significance.

Figure 6:
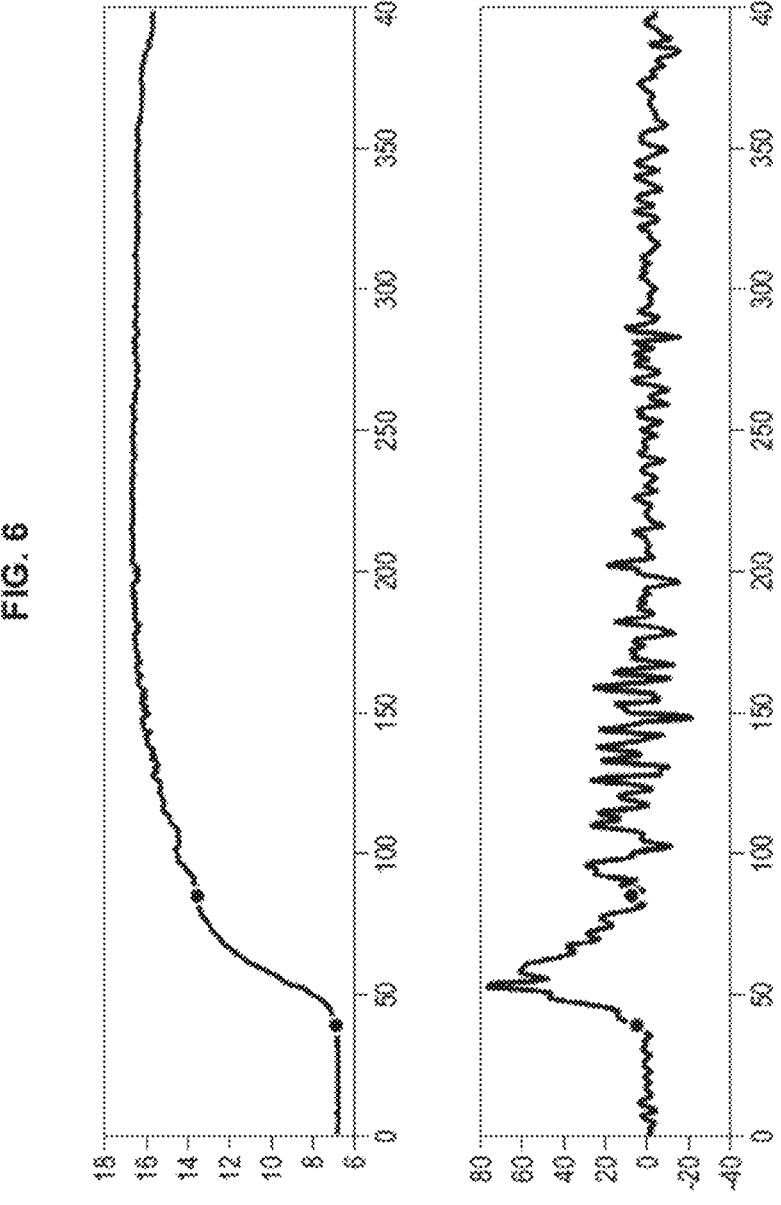
FIG. 6 illustrates a trajectory concerning a convergence movement and below it, the corresponding speed signal.

An example comparing vergence and saccade trajectories in a dyslexic individual and a non-dyslexic individual is presented in FIG. 6.

Discussion

In this study, we demonstrate a novel technique using REMOBI technology to objectively measure saccade and vergence disorders in dyslexics and non-dyslexics binocularly, without uncoupling vergence accommodation. Our study demonstrates subtle velocity abnormalities for both saccades and vergence and increased deconjugate post-saccadic drifts in dyslexics, suggesting inefficient binocular motor control in the dyslexic population. The tests used in this study enable a differential diagnosis of eye movement problems in dyslexia occurring independently from reading: namely, that dyslexics' reading difficulty could be partially a result of poor eye movement control.

High Peak but Slow Average Vergence Velocity in Dyslexics

In terms of vergence, as compared to healthy adolescents, dyslexic adolescents show lower average velocities, suggesting that dyslexic adolescents have overall difficulty making prompt vergence movements, i.e. moving from near to far space and vice versa. This could have implications on their ability to rapidly and accurately perceive depth differences between objects in the three-dimensional space. Psychophysical studies have established that depth perceptual ability relies on quality of vergence eye movements: divergence and convergence (Howard, I. P. & Rogers, B. J. in *Perceiving in Depth* Vol. Volume 2 Stereoscopic Vision (Oxford University Press, 2012)).

Notably, this is the first time the profile of the vergence velocity was studied in the dyslexic population. Interestingly, dyslexic adolescents exhibited an abnormal velocity profile: they demonstrated a more robust initial velocity (peak velocity) but their average velocity is slower; meaning their velocity is abnormally reduced in the later phases of movement for both convergence and divergence. From Hung's model of double control of vergence, we can consider vergence to be modeled as a dual-mode control system (Hung, G. K., Semmlow, J. L. & Ciuffreda, K. J. A dual-mode dynamic model of the vergence eye movement system. *IEEE Trans Biomed Eng* 33, 1021-1028, doi:10.1109/tbme.1986.325868 (1986)). The vergence response can be dissected into transient and sustaining components. The transient portion—the initial component—is assumed to be an open-loop control component of enhanced speed of a vergence response. The sustaining portion—the slow component—is assumed to be driven by a visual feedback, closed-loop control system. This closed-loop control system provides fine-tuning of the response and enables the extraordinary accuracy seen in binocular fixation.

Our observations are in line with Hung's model as they demonstrate group differences in the initial and subsequent vergence components. The initial velocity movement during the transient, phasic phase in dyslexic adolescents is faster than that of healthy controls. However, the subsequent portion of the velocity including the sustaining portion (subsequent 160 ms), which is visually driven, is slowed. We postulate that this is due to delays in sensory visual processing in dyslexics. In previous studies we have reported a similar phenomenon in a healthy population, in which only the visually driven component of vergence is slowed as a result of age (Yang, Q., Le, T. T. & Kapoula, Z. Aging effects on the visually driven part of vergence movements. *Invest Ophthalmol Vis Sci* 50, 1145-1151, doi:10.1167/iovs.08-2474 (2009)). In the dyslexic population, this hypothesis of deficits in the visually-driven, sustaining portion of vergence is also consistent with previous theories regarding deficits in the magnocellular visual pathway that is responsible for processing dynamic, rapidly changing binocular disparity (Stein, J. F., Riddell, P. M. & Fowler, S. Disordered vergence control in dyslexic children. *Br J Ophthalmol* 72, 162-166, doi:10.1136/bjo.72.3.162 (1988)).

Alternatively, abnormal velocity could be related to inappropriate tailoring of the pulse-slide-steps vergence motor command signals sent to extra-ocular muscles rather than to slower visual processing of the disparity and blur of retinal images (Leigh, R. J. & Zee, D. S. Ch. Vergence eye movements, (Oxford University Press, 2015)). In terms of motor control, the velocity of an movement depends on the quality of the movement generator signal located at the brainstem, i.e. in the mesencephalic reticular formation.[28] Inefficiency or dysfunction of the mesencephalic reticular formation in dyslexic adolescents could be at the origin of slower average vergence velocity. Whatever the reason, the impact of slower vergence is that clear single vision cannot be obtained as promptly as for non-dyslexics, i.e., dyslexic adolescents experience a delay in obtaining clear vision when moving their eyes from one depth to the other.

Vergence Velocity and Clinical Tests

It is notable that these vergence results, tested objectively with REMOBI lab equipment, correspond to the clinical testing performed. Dyslexic adolescents tended to have lower scores of stereovision as tested by the Titmus test. They also had higher Convergence Insufficiency Symptom Survey results, indicating symptomatic vergence disorders. As our lab has argued in the past, individualive orthoptic testing can be used as preliminary testing, but it is important to objectively measure vergence, namely any temporal abnormalities, in order to prescribe efficient rehabilitation (Ward, L. M., Gaertner, C., Olivier, L., Ajrezo, L. & Kapoula, Z. Vergence and accommodation disorders in children with vertigo: A need for evidence-based diagnosis. *EClinicalMedicine* 21, 100323, doi:10.1016/j.e-clinm.2020.100323 (2020)).

Slow Average Saccade Velocity and Disconjugate Drifts in Dyslexics

In addition to vergence differences, dyslexics displayed differences in saccades in the left and right directions as compared to healthy controls. Notably, as in vergence, dyslexic adolescents demonstrated normal latency, but showed a faster initial peak velocity and a slower average velocity than non-dyslexics, leading to a longer total duration to reach their target. As saccade duration lasted on average less than 80 ms (see Table 5), and visual processing is approximately of the same duration, visual feedback is less likely to intervene in the control of the ongoing saccade, which is therefore executed under open loop control. In the case of saccades, this abnormality favors a hypothesis of motor inefficiency. It is possible that the slowing of saccades is due to inefficient vergence involvement leading to not only the subsequent deconjugate drift, but also the slowed saccade itself. If vergence control is lost during the initial part of the saccade, when the eyes are rapidly accelerating, a rapid vergence restoration mechanism is activated to reestablish this loss of vergence (Jainta, S. & Kapoula, Z. Dyslexic children are confronted with unstable binocular fixation while reading. *PLOS One* 6, e18694, doi:10.1371/journal.pone.0018694 (2011)). Yet, as we have shown vergence velocity is slowed in dyslexics, the saccade would in turn also be slowed, leaving larger vergence drifts during the subsequent fixation period. In fact, what we call disconjugate drift may be physiologically produced by the vergence system that is slowed in dyslexics and fails to restore vergence during the saccade itself. It has been previously shown that, while vergence normally accelerates the saccade, it can also slow it (Kumar, A. N. et al. Tests of models for saccade-vergence interaction using novel stimulus conditions. *Biol Cybern* 95, 143-157, doi:10.1007/s00422-006-

0073-9 (2006); Zee, D. S., Fitzgibbon, E. J. & Optican, L. M. Saccade-vergence interactions in humans. *J Neurophysiol* 68, 1624-1641, doi:10.1152/jn.1992.68.5.1624 (1992)). Vergence, or disconjugate drifts, during fixation harm visual acuity and therefore, single binocular vision (Westheimer, G. & McKee, S. P. Visual acuity in the presence of retinal-image motion. *J Opt Soc Am* 65, 847-850, doi:10.1364/josa.65.000847 (1975)).

Interestingly, the difference in drifts was not statistically different after saccades to the left. Saccadic Left/Right asymmetries have been the individual of debate as previous studies have shown contradictory results (Tagu, J., Dore-Mazars, K., Lemoine-Lardennois, C. & Vergilino-Perez, D. How Eye Dominance Strength Modulates the Influence of a Distractor on Saccade Accuracy. *Invest Ophthalmol Vis Sci* 57, 534-543, doi:10.1167/iovs. 15-18428 (2016); Petit, L. et al. Strong rightward lateralization of the dorsal attentional network in left-handers with right sighting-eye: an evolutionary advantage. *Hum Brain Mapp* 36, 1151-1164, doi: 10.1002/hbm.22693 (2015); Honda, H. Idiosyncratic left-right asymmetries of saccadic latencies: examination in a gap paradigm. *Vision Res* 42, 1437-1445 (2002); Weber, H. & Fischer, B. Gap duration and location of attention focus modulate the occurrence of left/right asymmetries in the saccadic reaction times of human individuals. *Vision Res* 35, 987-998, doi:10.1016/0042-6989(94)00186-p (1995)). However, most of these conflicting studies have been conducted in adults, rather than dyslexic adolescents. As rightward saccades are controlled by the contralateral ocular motor areas, involving visual, parietal, and frontal cortexes, perhaps the asymmetry in dyslexics could be attributed to left hemisphere dysfunction. Clinically, this finding could be related to dyslexic difficulty in fixating on words as they progress to the right along a line of text while reading. However, as previous studies on Chinese and Arabic speakers with dyslexia have contributed significantly to our understanding of the interplay between reading patterns and dyslexic pathology, futures studies should consider investigating these findings in dyslexics who read using non-Latin script (Siok, W. T., Perfetti, C. A., Jin, Z. & Tan, L. H. Biological abnormality of impaired reading is constrained by culture. *Nature* 431, 71-76, doi:10.1038/nature02865 (2004); Beland, R. & Mimouni, Z. Deep dyslexia in the two languages of an Arabic/French bilingual patient. *Cognition* 82, 77-126, doi:10.1016/s0010-0277(01)00148-2 (2001); Friedmann, N. & Haddad-Hanna, M. Letter position dyslexia in Arabic: from form to position. *Behav Neurol* 25, 193-203, doi:10.3233/ben-2012-119004 (2012)).

Vergence Velocity and Disconjugate Post-Saccadic Drift are Correlated

For the first time to our knowledge, this study indicates problems in saccade velocity and high deconjugate drifts following large amplitude saccades in the dyslexic population. While it has previously been shown that dyslexics have deconjugate post-saccadic drifts during reading, the present study suggests this problem is inherent, as it exists for large saccades tested objectively with the REMOBI device. The results favor the hypothesis previously proposed by our lab: that disconjugate drifts arise from poor vergence control (Jainta, S. & Kapoula, Z. Dyslexic children are confronted with unstable binocular fixation while reading. *PLOS One* 6, e18694, doi:10.1371/journal.pone.0018694 (2011); Stein, J. & Kapoula, Z. Ch. Movements of the eyes in 3d space: deficits of vergence and binocular coordination in dyslexia, (Oxford University Press, 2012)). Further, our lab has previously shown that experimental induction of vergence/accommodation mismatch negatively impacts disconjugate post-saccadic drifts (Daniel, F. & Kapoula, Z. Induced vergence-accommodation conflict reduces cognitive performance in the Stroop test. *Sci Rep* 9, 1247, doi:10.1038/s41598-018-37778-y (2019)). Indeed, the present study argues that these vergence velocity abnormalities and disconjugate post-saccadic drifts are related. To substantiate this hypothesis regarding the physiologic link between vergence and saccades further, we examined the cross-correlation between some parameters. We found that the lower the velocity was during vergence, the higher the deconjugate drift of the saccades. This finding favors our hypothesis of a possible causal link between low vergence velocity capacity and poor binocular coordination after the saccade, or disconjugate drift.

When splitting the data of dyslexics and non-dyslexics, a significant negative correlation between average velocity and the disconjugate drift in the following 160 ms after the saccade was found for dyslexics only during convergence following left saccades. These deficits in saccades and vergence confirm that the dyslexic adolescent population exhibits difficulty in both controlling vergence along the median plane and maintaining vergence stability during fixation after saccades (seen in the increased disconjugate drift).

No Latency Abnormality in Dyslexics

Contrary to previous studies in our lab, we did not find any latency abnormality in dyslexics for vergence or saccades. However, contrary to our previous experiments, in this study, we used the visual-acoustic REMOBI device, which provides a sound stimulus 50 ms before LED onset. Further research on dyslexics comparing eye movements to audio-visual vs visual targets are currently being conducted in our laboratory.

Baseline Questionnaires

What else, outside of clinical and objective measures, could be associated with these eye movement abnormalities in the dyslexic population? Dyslexic adolescents tended to spend many more hours on the computer per week than non-dyslexic adolescents. It has been thought that dyslexic adolescents perform better when they are able to read and interact with a screen, so this finding may support their preference for screen learning.[41-43] Dyslexic adolescents also tended to like to go to theaters and films more than non-dyslexic adolescents, and, perhaps not surprisingly, liked reading less than non-dyslexic adolescents. We postulate that dyslexic adolescents also like to watch films more because they find reading too fatiguing. An open question that remains is to what extend prolonged used of computers aggravates the intrinsic vergence and binocular coordination problems of dyslexics.

Next Steps

As we have shown that dyslexic adolescents have poor eye movement in both vergence and saccades as compared to non-dyslexic adolescents, how can this new data inform the dyslexic community's efforts to build rehabilitation and alternative learning programs for those affected?

Traditionally, dyslexic adolescents have been assigned to orthoptic rehabilitation, during which they perform exercises over many sessions designed to rehabilitate their eye movements. This helps many adolescents; however, of the 47 dyslexic adolescents studied, 34 had been to an orthoptist or were currently enrolled in orthoptic rehabilitation, yet continued to exhibit objective eye movement deficits and their clinical manifestations of those deficits. Are there any other methods that can be used to help them overcome their persistent deficits? Using computers instead of paper has been one strategy the dyslexic community has used to facilitate easier reading and writing in their population (Berninger, V. W., Nagy, W., Tanimoto, S., Thompson, R. & Abbott, R. D. Computer Instruction in Handwriting, Spelling, and Composing for Students with Specific Learning Disabilities in Grades 4 to 9. Comput Educ 81, 154-168, doi:10.1016/j.compedu.2014.10.005 (2015); Tanimoto, S., Thompson, R., Berninger, V. W., Nagy, W. & Abbott, R. D. Computerized Writing and Reading Instruction for Students in Grades 4 to 9 With Specific Learning Disabilities Affecting Written Language. *J Comput Assist Learn* 31, 671-689, doi:10.1111/jcal.12110 (2015); van der Leij, A. Dyslexia and early intervention: what did we learn from the Dutch Dyslexia Programme? *Dyslexia* 19, 241-255, doi:10.1002/dys.1466 (2013)). However, spending so much time reading on a screen can have some side effects: namely, increasing visual stress, which could accentuate reading problems (Jaiswal, S. et al. Ocular and visual discomfort associated with smartphones, tablets and computers: what we do and do not know. *Clin Exp Optom* 102, 463-477, doi:10.1111/cxo.12851 (2019); Sheppard, A. L. & Wolffsohn, J. S. Digital eye strain: prevalence, measurement and amelioration. *BMJ Open Ophthalmol* 3, e000146, doi:10.1136/bmjophth-2018-000146 (2018); Mork, R., Falkenberg, H. K., Fostervold, K. I. & Thorud, H. M. S. Visual and psychological stress during computer work in healthy, young females-physiological responses. *Int Arch Occup Environ Health* 91, 811-830, doi:10.1007/s00420-018-1324-5 (2018); Collier, J. D. & Rosenfield, M. Accommodation and convergence during sustained computer work. *Optometry* 82, 434-440, doi:10.1016/j.optm.2010.10.013 (2011)).

On the other hand, perhaps these preliminary results related to eye movement deficits could be useful in planning retraining exercises. Previous studies using a double step vergence paradigm on the REMOBI machine have shown lasting improvements in reading saccades, fixations, and vergence measurements (Daniel, F., Morize, A., Bremond-Gignac, D. & Kapoula, Z. Benefits from Vergence Rehabilitation: Evidence for Improvement of Reading Saccades and Fixations. *Front Integr Neurosci* 10, 33, doi:10.3389/fnint.2016.00033 (2016); Ward, L. M., Gaertner, C., Olivier, L., Ajrezo, L. & Kapoula, Z. Vergence and accommodation disorders in children with vertigo: A need for evidence-based diagnosis. *EClinicalMedicine* 21, 100323, doi:10.1016/j.eclinm.2020.100323 (2020); Kapoula, Z. et al. Objective Evaluation of Vergence Disorders and a Research-Based Novel Method for Vergence Rehabilitation. *Transl Vis Sci Technol* 5, 8, doi:10.1167/tvst.5.2.8 (2016); Morize, A., Bremond-Gignac, D., Daniel, F. & Kapoula, Z. Effects of Pure Vergence Training on Initiation and Binocular Coordination of Saccades. *Invest Ophthalmol Vis Sci* 58, 329-342, doi:10.1167/iovs. 16-19837 (2017); Kapoula, Zoï et al. Efficient Rehabilitation of Vergence Accommodation in Adolescents: A Case Study. J Clin Stud Med Case Rep 6:074). Future research should repeat these experiments to verify audiovisual vergence retraining as a viable new rehabilitation technique. It may even be possible to use this method as a predictive test of dyslexic pathology using machine learning algorithms.

Conclusion

Dyslexic adolescents exhibit slower vergence and saccades, with a velocity profile that shows a higher peak velocity in the beginning of the movement, but slow deceleration in the subsequent phase of movement towards targets in the three-dimensional space as compared to non-dyslexics. Though other studies have reported differences in saccadic and vergence eye movements in dyslexic adolescents, this study demonstrates, for the first time to our knowledge, an objective difference in the velocity profile of vergence and saccades in the dyslexic adolescent population. Slow average vergence velocity and disconjugate drifts following saccades can be causally related. Our study suggests dyslexics' poor control of vergence dynamics alters saccade speed and induces disconjugate post-saccadic drifts. These deficits in both vergence and saccadic movement provide an oculomotor basis for their reading difficulties: as it is more difficult to accurately and quickly locate the words in the three-dimensional space, it is more difficult to read.

Further, by demonstrating that these deficits persist when making large degree movements to audiovisual stimuli, this study opens up the possibility for novel therapeutic rehabilitation techniques. The proposed testing method assess purely motor problems independently from reading, which could become a useful clinical tool. Notably, the eye movement targets in this experiment mimic movements in everyday life: the targets were placed horizontally in the three-dimensional space at eye level and were preceded by a beep, which provides some warning and intersensory facilitation. This is an exciting area of research: though orthoptic training has been considered the standard of care rehabilitation for the dyslexic population, perhaps there are new avenues to design rehabilitation programs to train dyslexic adolescent eye movements to respond more quickly and accurately to these audiovisual stimuli.

Finally, and most importantly, we would like to highlight that reading is a multisensory activity that is fundamentally based around the visual system, of which eye movement is an integral component. Although we do not claim these eye movement problems represent the sole pathology in dyslexia, we believe the fragile nature of dyslexic adolescents' eye movements provide an inadequate basis on which to build efficient reading skills. These subtle eye movement deficits may represent a symptom of larger motor coordination disorders that may be associated with dyslexia and other learning disabilities. Therefore, we argue that these subtle eye movement testing should be added as differential diagnostic criteria and used for evaluation and rehabilitation in the dyslexic population.

Example 3: Machine Learning Classification of Dyslexic Vs Non-Dyslexic Individuals on the Basis of Saccades and Vergences Parameters Tested with REMOBI and Analyzed with AIDEAL In order to further confirm the relevance of vergence and saccade parameters measured during vergence and saccade tests using REMOBI and calculated using AIDEAL (software implementing the method according to the invention), machine learning classification of dyslexic vs non-dyslexic individuals (29 dyslexic and 32 non-dyslexic adolescents) on the basis of the properties of their eye saccades, i.e. the latency, amplitude, speed, drift etc. parameters produced by AIDEAL after REMOBI stimulation (see Example 2 for details concerning REMOBI stimulation and AIDEAL processing of measured eyes movements) was attempted.

A KNeighborsClassifier was used as machine learning algorithm.

Results are presented in Table 4 below.

TABLE 4

Accuracy, specificity and sensitivity of classification of 61 individuals (29 dyslexic and 32 non-dyslexic) using KNeighborsClassifier based on saccade parameters calculated by AIDEAL using eye movements measured during a saccade test using REMOBI.

| Accuracy | Specificity | Sensitivity | Model | Penalty | C |
|---|---|---|---|---|---|
| 84.17% | 87.54% | 81.33% | KNeighborsClassifier | n.a | n.a |

These preliminary results show that saccade parameters calculated by AIDEAL based on REMOBI saccade test can excellently predict dyslexic individuals with 81% sensitivity (81% of dyslexic individuals are indeed classified as dyslexic) and 88% specificity (88% of non-dyslexic individuals are indeed classified as non-dyslexic).

To refine these results, the Lasso logistic regression was applied; this made it possible to identify that the most discriminating saccade parameters in this limited population are: average velocity of saccades, peak velocity of saccades, and disconjugacy during saccade.

The same approach was used for vergence parameters using two distinct well-known machine learning algorithms have been tested: support vector machine, and logistic regression.

Results are presented in Table 5 below.

TABLE 5

Accuracy, specificity and sensitivity of classification of 61 individuals (29 dyslexic and 32 non-dyslexic) using support vector machine or logistic regression based on vergence parameters calculated by AIDEAL using eye movements measured during a vergence test using REMOBI.

| Accuracy | Specificity | Sensitivity | Model | Penalty | C |
|---|---|---|---|---|---|
| 81.48% | 77.58% | 86.9% | support vector machine | l2 | 1 |
| 81.48% | 78.11% | 86.77% | logistic_regression | l2 | 10 |

The Support Vector machine learning model as well as the logistic regression method show a sensitivity of almost 87% to identify dyslexics and a specificity of about 78% to identify non-dyslexics. The application of the Lasso method indicates that the parameters calculated by AIDEAL that are the most discriminating for vergence are: average velocity of vergences, peak velocity of vergences, and duration of vergences.

These preliminary results confirm the relevance of measuring saccade and vergence parameters (in particular at least one of saccades and vergences average and peak velocity, disconjugacy during saccades and vergences duration) for the functional exploration as a diagnostic aid of dyslexic individuals.

Figure 14A:
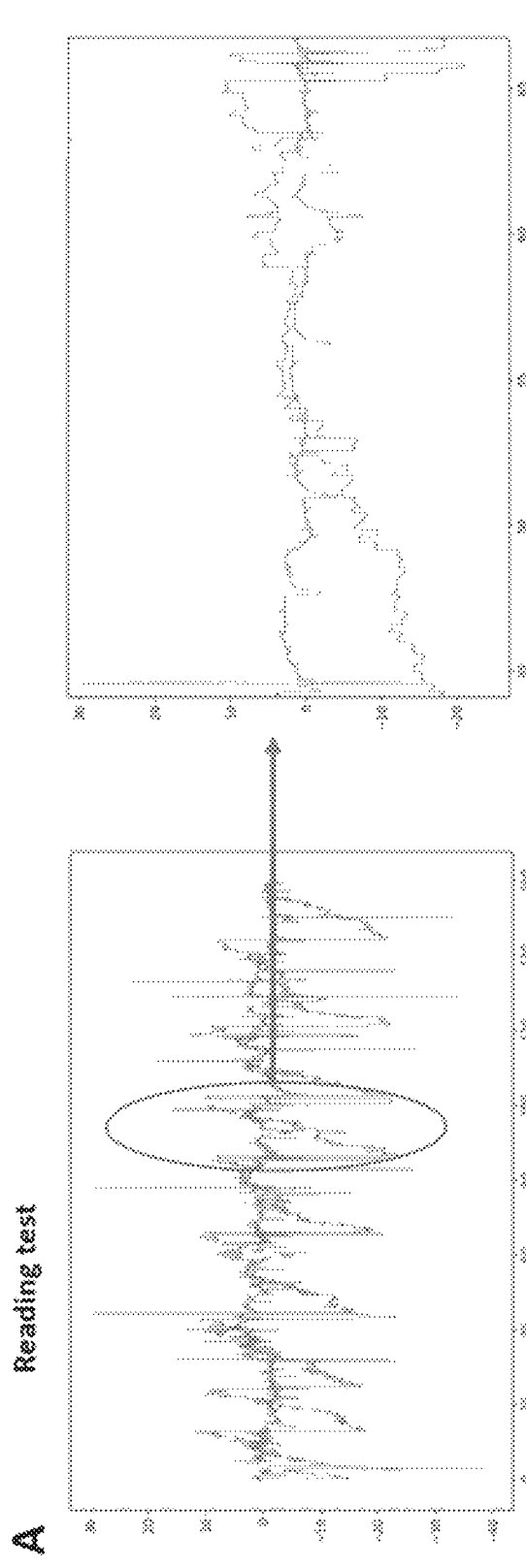
FIG. 14. Functional exploration of a 16-years old dyslexic individual using a vergence test, a saccade test, a reading test and an image analysis test. (A) Curves of the eyes movements during reading. In this figure, on the x-axis we have time; in y the conjugate signal of both eyes in degrees, showing the succession of saccades to the right followed by fixations fixing the words one after the other, then the large saccade to the left to start reading the next line. (B) Vergence trajectories during a vergence test. (C) Saccades trajectories during a saccade test. (D) Eyes movements during an image analysis test.

Example 4. Functional Exploration of Individuals Suffering from a Learning Disorder Using the Method According to the Invention Functional exploration with a vergence test, a saccade test, a reading test and an image analysis test was performed in several individuals suffering from a learning disorder. Results obtained for a 16-years old dyslexic individual are presented in FIG. 14:

FIG. 14A shows eyes movements during reading (see Example 1 for description of the reading test).

Figures 14B, 14C:
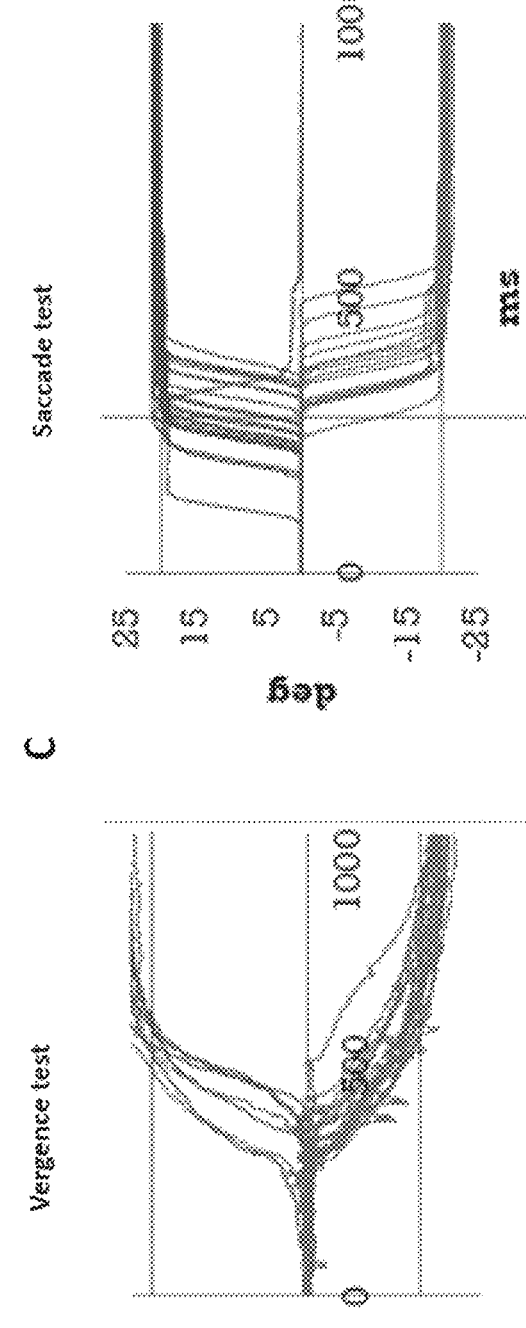

FIG. 14B shows vergence trajectories during a vergence test (see Example 1 for description of the vergence test).

FIG. 14C shows saccade trajectories during a vergence test (see Example 1 for description of the saccade test).

Figure 14D:
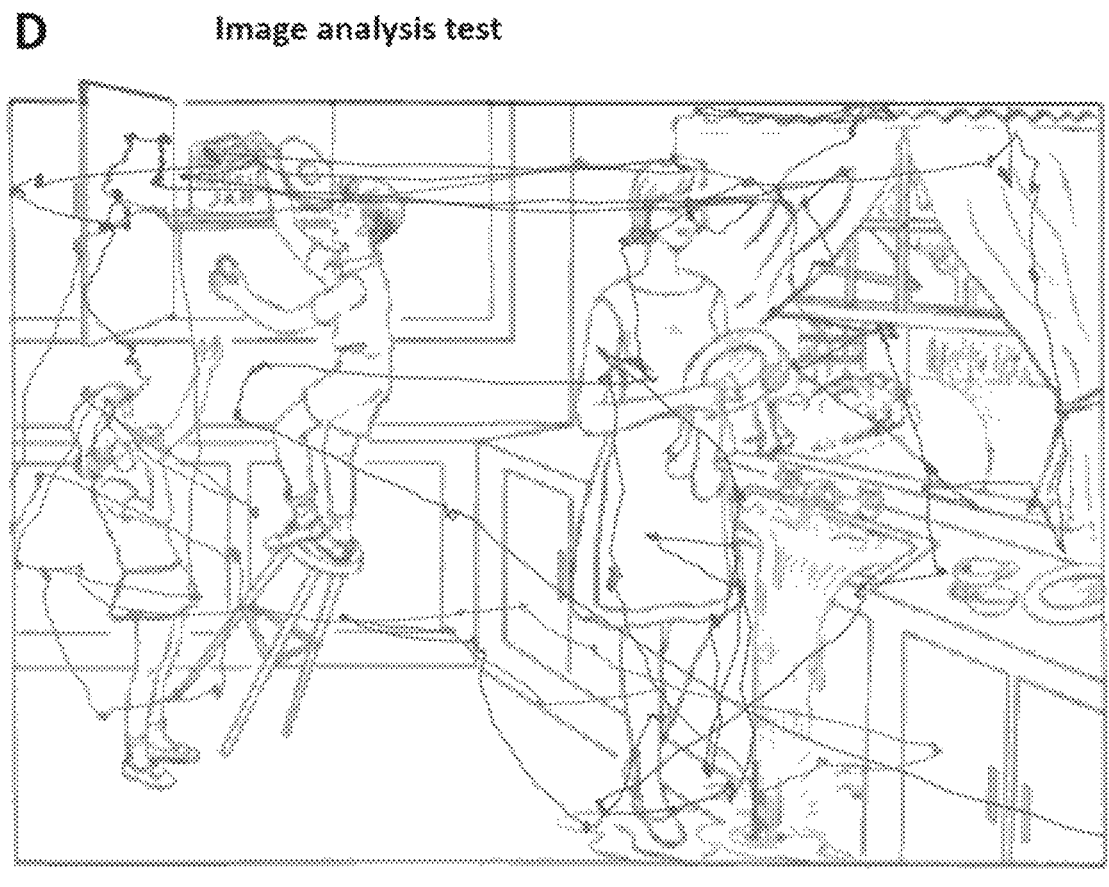

FIG. 14D shows eyes movements during an image analysis test.

The individual is questioned about what is represented in the image and what story the image discloses. The sections of the image fixated by the eyes are also analyzed (the eyes trajectories may be reported on the image to see what parts of the image have been fixated and in which order) and compared to the verbal reports and understanding of the image provided by the individual. This type of test is used typically by neurologists and neuropsychologists for functional exploration of the attention and cognitive executives process. Comparison of verbal reports of the patient with the eye movement exploration enables better understanding on the deployment of the image analysis by the patient. Interestingly, some key parts of the image could be not commented by the person while still his/her eyes were fixating or vice versa.

FIG. 14 shows that, in this dyslexic individual, vergences and saccades are normal; although eye movements during reading are very disturbed. Here it is shown that the problem of eye movements during reading (back and forth between words) are related to the language disorder and not to intrinsic binocular motricity troubles. In the neurological test of the image, the exploration is normal.

Figure 15A:
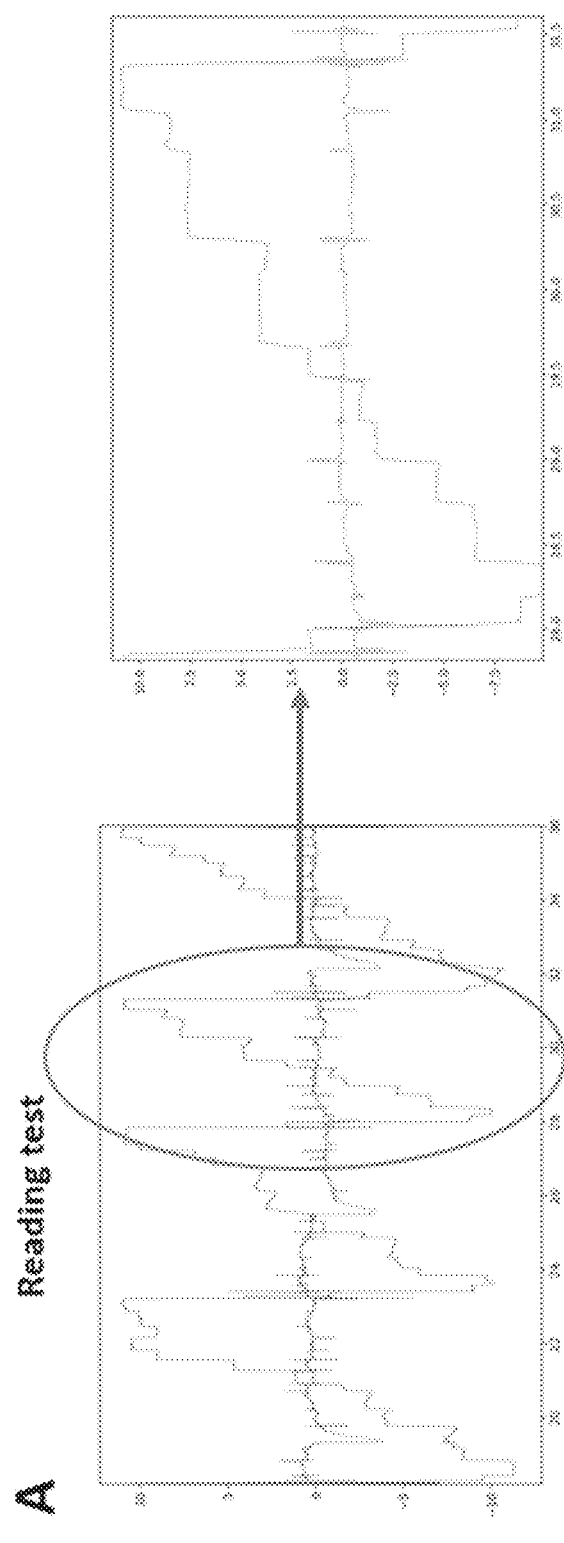
FIG. 15. Functional exploration of a 19-years old dyspraxic individual using a vergence test, a saccade test, a reading test and an image analysis test. (A) Curves of the eyes movements during reading. In this figure, on the x-axis we have time; in y the conjugate signal of both eyes in degrees, showing the succession of saccades to the right followed by fixations fixing the words one after the other, then the large saccade to the left to start reading the next line. (B) Vergence trajectories during a vergence test. (C) Saccades trajectories during a saccade test. (D) Eyes movements during an image analysis test.
Figures 15B, 15C:
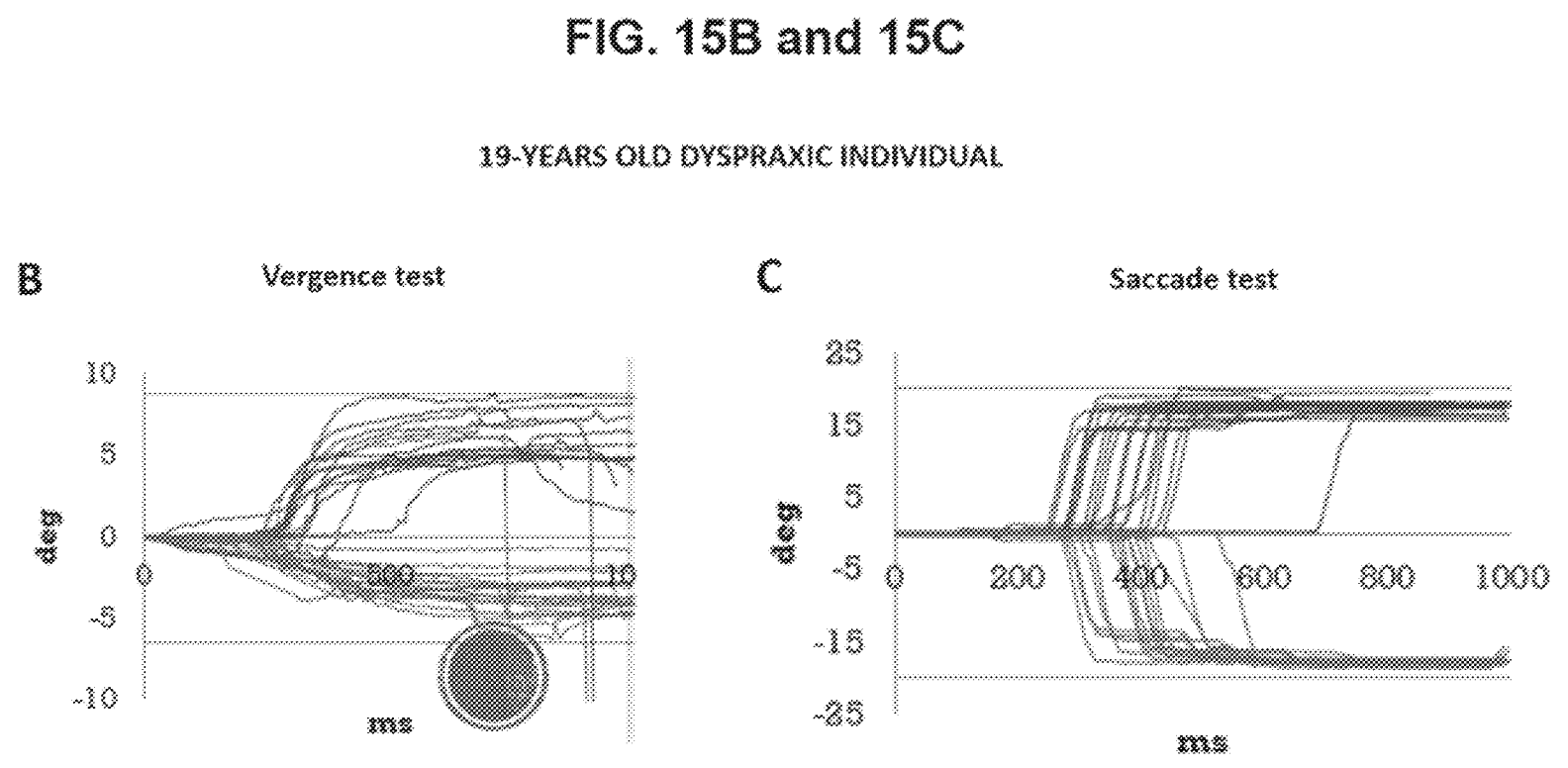
Figure 15D:
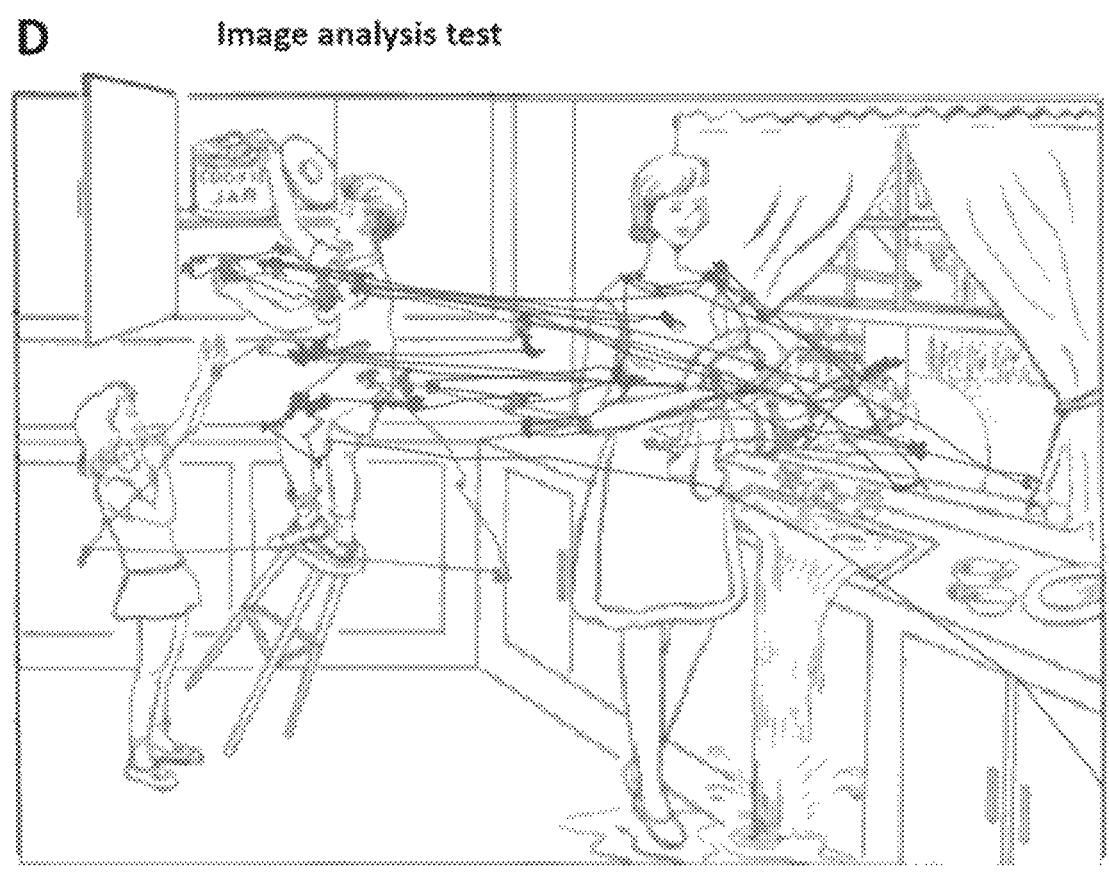

Results obtained for a 19-years old dyspraxic individual are presented in FIG. 15, with the same type of data presented in A, B, C and D as in FIG. 14.

FIG. 15 shows that, in this dyspraxic individual, vergences and saccades are variable in the REMOBI tests, the reading pattern is near-normal, exploration during the neurological image reading test is very biased and partial.

Figure 16A:
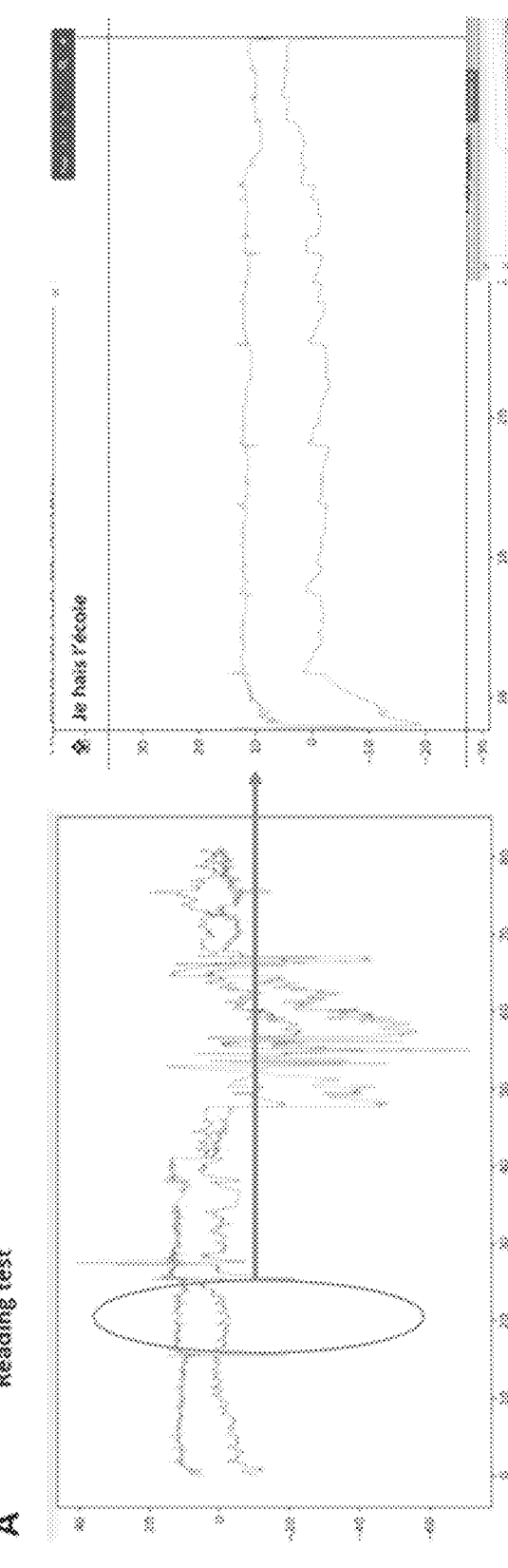
FIG. 16. Functional exploration of a 12-years old dysphasic individual using a vergence test, a saccade test, a reading test and an image analysis test. (A) Curves of the eyes movements during reading. In this figure, on the x-axis we have time; in y the conjugate signal of both eyes in degrees, showing the succession of saccades to the right followed by fixations fixing the words one after the other, then the large saccade to the left to start reading the next line.
Figures 16B, 16C:
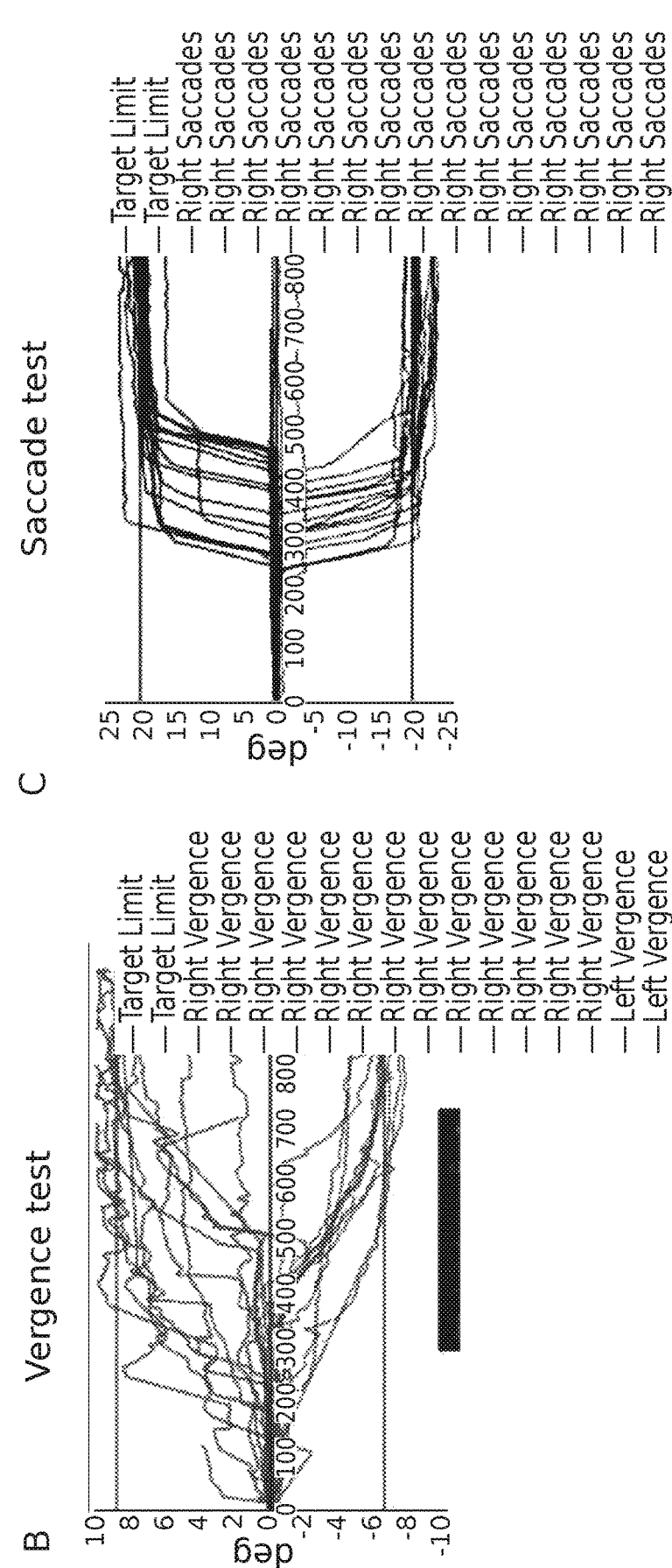
Figure 16D:
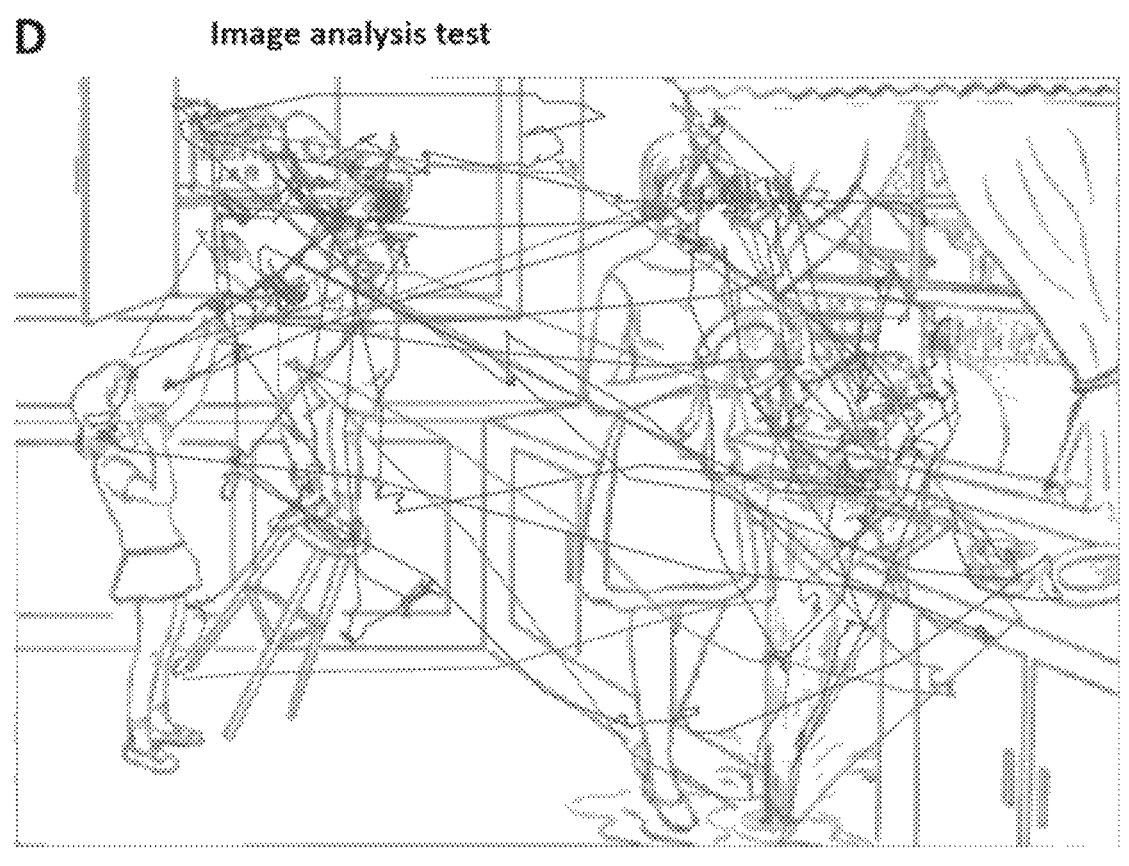

Results obtained for a 12-years old dysphasic individual are presented in FIG. 16, with the same type of data presented in A, B, C and D as in FIG. 14.

FIG. 16 shows that, in this dysphasic individual, very variable vergences and saccades are observed, as well as disturbed reading (regressive saccades). Moreover, normal semantic exploration of image and risk identification is observed, even if, according to the neurologist, the child sometimes has difficulty finding words.

The above results show that functional exploration based on a reading test, a vergence test, a saccade test, and an image analysis test permits to identify the presence or absence of intrinsic binocular motricity abnormalities, as well as the presence or absence of neurological deficits, thus showing the general usefulness of the methods according to the invention for the clinical management of individuals with learning disorders.

Example 5: Anomalies of Vergence in Patients with Vertigo: Diagnosis and Neuro-Rehabilitation with REMOBI Patients, Materials and Methods Patients Fourteen vertiginous patients participated in the study. The "vertigo" symptom was the essential criterion of inclusion. These patients were initially assessed on the ENT plan and underwent a complete orthoptic examination. Vestibular function was assessed by videonystagmoscopy (VNS) in complete darkness. None of these patients were in acute attacks of vertigo. In other words, none of them had spontaneous nystagmus that could be observed with bare eyes. The ocular fixation index was therefore correct, that is to say that the visual fixation completely inhibited any spontaneous vestibular nystagmus observed under VNS.

Remobi, Vergence Test and Rehabilitation

In order to objectively evaluate the presence of abnormalities of vergences, we used the device REMOBI. REMOBI (U.S. Pat. No. 8,851,669), is a trapezoid-shaped horizontal device, equipped with visual-acoustic elements (diodes and buzzers) and embedded software. REMOBI is a device that contains specific and different algorithms, on the one hand for the assessment (diagnosis of anomalies of vergences), on the other hand, for their neuro-rehabilitation of vergence movements. The patient's eye movements were recorded in this study with the EyeSeeCam video-oculography, binocular with a frame rate of each eye at 220 Hz (see eyeseecam.com, Munich).

Test for the assessment of vergences: the vergence movements were tested with the following paradigm: at each test a fixation diode was presented in the median plane at 40 cm of the subject during 1500 ms, preceded by a short beep which served as a warning attentional; then a second diode appeared 1200 to 1800 ms after the beginning of the first presentation, is located at 1.50 m from the subject, or located 20 cm from the subject. In the first case, a divergence movement had to be made a diode to fix further away.

In the second case, a convergence movement had to be made to fix a diode closer (see FIG. 1C). This vergence test consisted of 40 randomly interpolated trials containing 20 convergence and 20 divergence trials.

Vergence rehabilitation protocol: for the rehabilitation of vergence, we used another embedded algorithm at REMOBI, the so-called Vergence protocol in double step, detailed in the study by Kapoula, Z. et al. *Transl Vis Sci Technol* 5, 8, doi:10.1167/tvst.5.2.8 (2016). During this protocol, the subject must make a vergence movement towards the first target diode. This target, however, is presented only for a very short time and is replaced by a second target, even closer to convergence training and even more distant for divergent training, forcing the subject to quickly reprogram the initial movement (see FIG. 4). The results brought by Kapoula, Z. et al. *Transl Vis Sci Technol* 5, 8, doi:10.1167/tvst.5.2.8 (2016) in students with vergence abnormalities demonstrated the efficiency of this method; indeed, after 5 sessions of 35 min we confirmed an amplification and acceleration of convergences and divergences, lasting 18 months later. In this study, 4 rehabilitation sessions were performed with the REMOBI device by the service orthoptist. The sessions were held weekly. Eye movements were not recorded during these sessions, each lasting 20 minutes.

The rehabilitation of the vergences was done by alternating either the sitting position or the standing position. Each time the REMOBI device was placed at eye level. In the standing position, the person leads the synergy between vergences and postural balance in a more active way, which results in a real reeducation combining the gaze and the vestibular and postural function.

The vergence test (assessment) presented above, including oculomotor recording by video-oculography, was performed before the rehabilitation and 1 month after the end of the 4 rehabilitation sessions.

Posture Test

The body sway was measured with the small DynaPort MiniMod® (McRoberts B.V. The Hague, The Netherlands) device (74 g) equipped with three intransverse, sagittal and coronal orthogonally mounted accelerometers (AXXL202, AnalogueDevices, Norwood MA, USA), placed on a belt at the lumbosacral level and near the center of mass of the body was evaluated. The frequency of sampling is set at 100 Hz. This device is known to be easy to use in the elderly, during various activities such as cycling, sitting, standing, and recently during quiet upright.

Postural parameters: We measured the following parameters: (1) standardized area (in mm2/s), area of the ellipse region containing 95% of the information points in $mm^2$, divided by the duration of the measurement, (2) the Root-Mean-Square of the Medio-Lateral Body Sway (RMS of M/L in mm), (3) the Root-Mean-Square of the Antero-Posterior Body Sway (RMS of A/P inmm), (4) the Root-Mean-Square of the Medio-Lateral velocity (in mm/s), (5) the Root-Mean-Square of the Antero-Posterior velocity (in mm/s). These parameters are obtained in g from the raw information of gravity acceleration. After the information is filtered high-pass, the velocity is calculated in the direction of A/P and M/L by means of the acceleration signal integration and displacement by means of the velocity signal integration.

Data Analysis

Data recorded with the Pupil Labs eye tracker were analyzed with AIDEAL, software developed in the IRIS laboratory (see French patent application filed on May 14, 2020 under number FR2004768, DSO2020003510, 2 mars 2020). The vergence signal was derived by calculating the difference between the two eyes from the individual calibrated eye position signals (i.e., left eye–right eye). The beginning and end of the vergence movements were defined as the time point when the eye velocity exceeded or dropped below 5°/s: these criteria are standard and were applied automatically by the AIDEAL software; the program estimated the initial phasic component as the amplitude between these two initial points. It also calculated the amplitude change during the subsequent 80 ms and 160 ms. The total amplitude was calculated as the sum of the amplitude of the initial phasic component plus the 160 ms component. The total duration was calculated as the duration of the phasic component plus the subsequent 160 ms.

For saccade analysis, AIDEAL treated the conjugate signal, e.g. the L+R eye position/2. The onset and the offset of the saccade were defined as the time points where the velocity went above or below 10% of the peak velocity; practically, this corresponded to values above or below 40°/s (as the peak velocity of 20° saccades is typically above 400°/s). The total average velocity was defined as the ratio of total amplitude in degrees divided by time in seconds. To evaluate binocular coordination of saccades, or the disconjugacy during saccadic movements, the difference in amplitude between the left and the right eye signal was calculated. The disconjugate drift, or the difference in drift amplitude during the first 80 or 160 ms of fixation, was calculated. These calculations are standard and have been used in previous experiments (Kapoula, Z. et al. *Transl Vis Sci Technol* 5, 8, doi:10.1167/tvst.5.2.8 (2016); Morize, A., et al. *Invest Ophthalmol Vis Sci* 58, 329-342, doi:10.1167/iovs.16-19837 (2017)).

Trials with blinks or other artifacts were discarded automatically by AIDEAL.

Results

Patients Characteristics

Table 6 below present patients characteristics:

TABLE 6

Patients characteristics. Among the patient complaints, this table lists four types of vertiginous symptoms: Positional vertigo (vertigo triggered and felt during a supine position), Vestibular Athenopia (Set of relatively permanent visual and movement-related symptoms), Discreet vertigo (brief, episodic vertigo, perceived several times a day), and Chronic vertigo (recurrent vertigo with a rotational nature and evolving by seizures). The vestibular state gathers the observations made under videonystagmoscopy, the eye being filmed in the dark, under infrared camera. It indicates either the objective characteristics of an asymmetry of the vestibular balance or, in the absence of objective signs, a subjective notion of sensory discomfort related to movement: the presence of spontaneous nystagmus indicates an uncompensated vestibular state, and hyporeflectivity is the residual sign of vestibular hypofunction observable during stimulation during the rotational pulse test protocol.

| | Gender and age | Main complaint | Age of vertigo symptoms | Fusion amplitudes | PPC (cm) | Vestibular state |
|---|---|---|---|---|---|---|
| 1 | M 76 | Positional vertigo | 3 weeks | strabic | 8 | Hypersensitivity |
| 2 | F 38 | Vestibular Athenopia | 5 weeks | C'25 C18 D'10 D2 | 5 | Hypersensitivity |
| 3 | M 79 | Vertigo and instability | 3 years | C'18 C8 D'12 D4 | 7 | Spontaneous right |
| 4 | M 58 | Vertigo and diplopie | 2 weeks | C'30 C20 D'12 D4 | 10 | Left hyporeflectivity |
| 5 | F 55 | Vestibular Athenopia | 6 weeks | C'35 C8 D'12 D4 | 8 | Hypersensitivity |
| 6 | F 63 | Discreet vertigo | 8 years | C'20 C8 D'12 D4 | 7 | Right hyporeflectivity |
| 7 | F 52 | Vestibular Athenopia | 2 months | C'35 C18 D'12 D10 | 5 | Nys. Sp. Vert. Inf. idiop. |
| 8 | M 64 | Positional vertigo | 10 days | C'20 C16 D'10 D2 | 5 | Hypersensitivity |
| 9 | M 40 | Discreet vertigo | 3 weeks | C'14 C8 D'10 D2 | 5 | Left hyporeflectivity |
| 10 | F 53 | Discreet vertigo | 15 days | C'30 C4 D'6 D2 | 5 | Hypersensitivity |
| 11 | F 33 | Vestibular Athenopia | 3 months | C'18 C18 D'12 D4 | 3 | Hypersensitivity |
| 12 | F 48 | Discreet vertigo | 5 months | C'35 C14 D'8 D2 | 3 | Right hyporeflectivity |
| 13 | M 61 | Chronic vertigo | 4 years | C'30 C4 D'6 D4 | 15 | Left hyporeflectivity |
| 14 | M 65 | Chronic vertigo | 8 years | C'0 C10 D'10 D10 | 7 | Right hyporeflectivity |

Examples of Eye Movement Results:

FIGS. 17A and 17B show the trajectories of the vergences of patient 5. Clinically, this patient complained of sensitivity to optic flow generating nausea appeared a few weeks before the first consultation, impressions of instability fleeting, of feeling of permanent flutter and discomfort in rapid movements of the head and eyes.

FIG. 17A shows the trajectories of its convergences (traced upwards) and the trajectories of its divergences (traced downwards) during the 2.5 min of vergence test performed before rehabilitation. The bold lines indicate the position of the respective target that the eyes should reach. This figure shows a strong hypometry especially for convergence.

FIG. 17B shows the trajectories of the patient 1 month after the 4 rehabilitation sessions. There is a significant acceleration and amplification of the convergence, the movement initially the most deficient. For divergence, there is a reduction in latency. Subjectively, the patient reported greater ease of visual exploration of her environment, a greater sense of stability, and increased confidence when walking.

FIG. 18A presents the results of patient 14, suffering from an old and well documented left Meniere's disease. He had undergone classical vestibular rehabilitation (consisting of 9 rotary chair sessions). This rehabilitation was beneficial and avoided surgery with its labyrinthine risk. However, episodically, small attacks of low intensity and well tolerated by the patient reappeared; indeed, the periodically reproduced vestibular examination showed a state of marked left deficit with right directional gravity.

Interestingly, we see in FIG. 18A a paucity of vergences. The patient tries to converge by performing earlier jerky movements, of low amplitude, reaching neither the target of the convergence (bold line at high) nor the target of the divergence (bold line down). We then conclude in the existence of a major deficit of all vergences for this patient suffering from several years of Meniere's disease.

A major improvement in vergence trajectories is observed after rehabilitation (FIG. 18B).

Vergence problems exist in 39% of the population, but in the presence of vestibular pathology, as in this study, nearly 100% of patients have problems with vergence. Fifty percent of the patients, 8 of the 14 patients studied, experienced an improvement in the quality of their vergences: in only four REMOBI neuro-rehabilitation sessions, the latency times decreased, the amplitudes or the speed increased, the movements became more regular and the saccade-vergence couple improved. Patients report better comfort in their relationship to space and their ability to move. The benefits were particularly significant in patients with vestibular asthenopia and Meniere's disease.

Eye Movement Results

Observation of all subjects indicates a significant increase of the amplitude of divergence or convergence in the standing position compared to the seated condition (see FIGS. 19A & 19B).

Also, there was a statistically significant difference in the latency of divergence when comparing the results of before and after rehabilitation (p<0.01, see FIG. 20).

Analysis of a Movement According to Origin of Vertigo:

In the following analysis we separated patients with functionally origin of vertigo from all the others whose vertigo symptoms were related to organic results. These additional analyses indicated significant differences that differed from the two groups.

When considering the data for the patients with organic origin of the vertigo there is a statistically significant higher amplitude of divergence in standing than the seated condition (p=0.0277, see FIG. 21A). Also, we find a significantly lower latency of the divergence in the post rehabilitation testing in standing condition relating to the pre rehabilitation testing (p=0.0277, see FIG. 21B).

For the subjects with the functional disorder that is Hyper Sensibility, there is a statistically significant higher amplitude of the divergence in standing in the post rehabilitation testing when compared to the pre rehabilitation testing (p=0.0277, see FIG. 21C).

Also, the latency of divergence in standing condition decreased significantly in the post rehabilitation condition compared to the pre rehabilitation testing (p=0.046, see FIG. 21D).

Results on Posture:

Unfortunately, for technical issues, postural measurements were done only during pre-rehabilitation tests.

Considering all patients, they did not show any significant results.

Considering the two groups in contrast:

For the hypersensitivity group (or organic group), on observation one observes that the activation of the medio lateral body sway was statistically significant when actively performing vergence eye movements compared to when fixating near or far (see FIG. 22)

Hypo group with organic origin of vertigo patients was not significantly different in posture between conditions, but there was a significant correlation between posture parameter and the eye movements.

In hyporeflectivity patients, mediolateral body sway increased when the amplitude of convergence increases (see FIG. 23A) or when latency of convergence decreases (see FIG. 23B). Correlation was found between the latency of convergence and the mean power frequency, the longer the latency of the conversions the shorter the mean power frequency (see FIG. 23C).

Discussion

The above results showed improvements particularly for divergence and more particularly in the standing position.

This is important as indeed the presence of vertigo in patients with their fear restricts somehow the capacity to move the eyes from near to far space which is done with the divergence movement before even undertaking any action.

The results show that transition from near to far space is done with shorter preparation time (shorter latency) and larger amplitude. The fact that such improvements are seen mostly at the standing position is also important because it indicates some part of multi-sensory facilitation of the binocular eye movement control by the vestibular and somatosensory signals coming from the ears and the body while in the standing position. Thus, these observations correlate with the subjective reports from several patients reporting better body self-control and more confidence while ambulating in the space in everyday life.

Further analysis of the postural and eye movement results shows that patients with functional origin of vertigo show smaller acceleration of ML body sway while doing vergence eye movements than while fixating. Such observations have been made previously in elderly with a falling history (Matheron E, Yang Q, Delpit-Baraut V, Dailly O, Kapoula Z. Active ocular vergence improves postural control in elderly as close viewing distance with or without a single cognitive task. Neurosci Lett. 2016 Jan. 1; 610:24-9) or even in patients with bilateral vestibular loss (Kapoula Z, Gaertner C, Yang Q, Denise P, Toupet M (2013) Vergence and Standing Balance in Subjects with Idiopathic Bilateral Loss of Vestibular Function. PLOS ONE 8(6): e66652).

Thus, many patients with functional origin of vertigo clearly can benefit from vergence eye movement rehabilitation as done with the REMOBI technology. The results from patients with organic origin confirm the link between eye movements and posture and indicate fragile link in these cases. Also, the mean power frequency is believed to be an indicator that less energy needed to keep posture stable (see Matheron E, Yang Q, Delpit-Baraut V, Dailly O, Kapoula Z. Active ocular vergence improves postural control in elderly as close viewing distance with or without a single cognitive task. Neurosci Lett. 2016 Jan. 1; 610:24-9). Presumably the patients capable to trigger their convergence with shorter latency, are also capable to control their postural stability by deploying less energy.

Conclusions

All patients who experienced vertigo, regardless of their origin, consistently showed vergence disorders. This mediocre quality of vergence eye movements observed in the course of a vertiginous patient history is explained by the reciprocity highlighted between vestibular function and that of vergences. A specific rehabilitation of vergence movements (double step process) with the multi-sensory, audio-visual REMOBI device stimulating movements of the eyes in the real 3D space allows to recover the lost quality of these vergence movements, namely in terms of temporality, but also in some cases in terms of velocity and accuracy. This subjective patient reports highlight their improved self-confidence in ambulating in space during their everyday activity. Although the study is pilot, given the massive research evidence for a symbiosis between vergence and vestibular function, the vestibular reeducation devoted to the treatment of vertigo cannot therefore neglect the specific work of binocular eye movements. The REMOBI &AID-EAL technology invented is the only one enabling measure and rehabilitation of binocular vergence eye movements to targets in real 3D space without the known side effects of devices such as screens or virtual reality.

Theoretically, vergence disorders in these patients confirm the natural symbiosis that exists between vergence and vestibular function. Persistent abnormalities of vergence may contribute to the maintenance or recurrence of vertigo symptoms. The neuro-rehabilitation protocol with REMOBI (standing-seated) is integrative, stimulating both the binocular visuo-motor system, the cortical (frontal parietal) and subcortical network controlling this motor function, the musculoskeletal system as a whole, using stimuli in real space in three dimensions, as in everyday life. It allows the improvement of the temporality of the vergence and thus a better interaction between vestibular and postural functions.

The invention claimed is:

1. A method of processing data representative of a person's binocular motor skills, the method comprising the following steps:

stimulating a person's binocular motricity by means of a binocular motricity stimulation device configured to specifically stimulate saccades, vergences or a combination of both or of a text or image reading test;

acquiring a movement of the right eye and the left eye of a person during the stimulation and, if applicable, a stimulation signal from the binocular motor stimulation device; the method comprising the following steps carried out in a processing unit;

determining from the movement of the left eye and the right eye several effective trajectories of the eyes in response to each stimulation, an effective trajectory corresponding to a saccade and/or a vergence movement of the eyes;

determining, for each stimulation, a representative trajectory of the eyes by processing all the effective trajectories for a given stimulation so as to obtain trajectory representative of said stimulation;

for each stimulation, comparing each effective trajectory with the corresponding representative trajectory by calculating a distance between said effective trajectory and the theoretical trajectory and, if the distance is greater than a fixed threshold, eliminating said effective trajectory, so as to eliminate the erroneous effective trajectories furthest from the representative trajectory and thus obtain selected trajectories for each stimulation;

processing each selected trajectory so as to obtain saccade and/or vergence parameters, the parameters being characteristic of a possible pathology of a person.

2. The method as claimed in claim 1, comprising a step of displaying an image of the stimulation device on which the trajectories of eye movement are represented.

3. The method as claimed in claim 1, wherein the effective trajectory corresponding to a saccade is obtained by calculating a conjugate signal defined by averaging the position of the left eye with the position of the right eye.

4. The method as claimed in claim 1, wherein the effective trajectory corresponding to a vergence is obtained by calculating a non-conjugated signal defined by the difference of the position of the left eye with the position of the right eye.

5. The method as claimed in claim 1, in which the movement of the right eye and the left eye are acquired with targets presented in 3D real space, the method comprising a step of transforming the movement of the right eye and the left eye into degrees.

6. The method as claimed in claim 1, in which a saccade parameter is the saccade peak velocity, or the average velocity.

7. The method as claimed in claim 1, wherein a saccade parameter is the amplitude of a saccade, the amplitude being defined between the onset of the saccade and the offset of the saccade, the onset of the saccade being defined by the time at which the saccade has a velocity of x % of the peak velocity of the saccade, the offset of the saccade being defined by the time after peak velocity at which the saccade has a velocity of x % of the peak velocity, x being between 5 and 15.

8. The method as claimed in claim 1, in which the visual test consists of subjecting the person to a first visual stimulus and then subjecting him/her to a second visual stimulus located at a different place from the first visual stimulus, a saccade parameter being a latency defined by the duration between the instant of activation of the second visual stimulus and the onset of the trajectory of the eyes to pass from the first visual stimulus to the second visual stimulus.

9. The method as claimed in claim 1, in which a saccade parameter is the saccade duration defined by the time between the offset of eye movement and the onset of eye movement.

10. The method as claimed in claim 1, in which a saccade parameter is the amplitude of the difference between the two eyes between the onset of the saccade and the offset of the saccade.

11. The method as claimed in claim 1, wherein a saccade parameter is one of the dis-conjugation parameters: obtained on the basis of the signal of the difference between the position of the left eye and the right eye.

12. The method according to claim 11, wherein a dis-conjugation parameter is one of the following parameters:

amplitude of the dis-conjugation expressed in degrees of the defined saccade: amplitude of the difference between the two eyes between the onset and the offset of the saccade;

drift 1 expressed in degrees: amplitude of the dis-conjugation between the offset of the saccade and up to 80 ms after the offset of the saccade;

drift 2 expressed in degrees: amplitude of the dis-conjugation between the offset of the saccade and up to 160 ms after the offset of the saccade.

13. The method as claimed in claim 1, wherein a vergence parameter is the amplitude of a vergence, the amplitude being defined between the onset of the vergence and the offset of the vergence, the onset of the vergence being defined by the instant at which the vergence has a velocity of x % of the peak velocity of the vergence, the offset of the vergence being defined by the instant after peak velocity at which the vergence has a velocity of x % of the peak velocity, x being between 5 and 15.

14. The method as claimed in claim 1, in which the visual test consists of subjecting the person to a first visual stimulus and then subjecting him/her to a second visual stimulus located at a different place from the first visual stimulus, a vergence parameter being a latency defined by the duration between the instant of activation of the second visual stimulus and the onset of the trajectory of the eyes to pass from the first visual stimulus to the second visual stimulus.

15. The method as claimed in claim 1, wherein a vergence parameter is the duration of vergence defined by the time between the offset of eye movement and the onset of eye movement.

16. The method as claimed in claim 1, wherein a vergence parameter is the amplitude of the difference between the two eyes between the onset of the vergence movement and the offset of the vergence movement.

17. The method as claimed in claim 1, wherein a vergence parameter is the amplitude of the vergence drift during the 80 ms or 160 ms after the offset of the vergence movement.

18. The method as claimed in claim 1, wherein a visual test is a reading test, the trajectories being progressive rightward saccades and/or regression saccades i.e. returns to the previous word.

19. The method as claimed in claim 1, wherein the person is an individual suffering from a learning disorder, preferably a dyslexic individual.

20. The method according to claim 19, wherein:

in step of stimulating a person's binocular motricity, the person's binocular motricity is stimulated by means of a binocular motricity stimulation device configured to specifically stimulate vergences, saccades, and by a text reading test, and the step of processing each selected trajectory comprises calculating:

a preferred combination of vergence and saccade parameters during vergence and saccade tests respectively, in particular:

i) average velocity of convergences, divergences, and left and right saccades, ii) duration of convergences, divergences, and left and right saccades, iii) disconjugacy 80 ms and/or 160 ms after right and left saccades, or after right saccades only, iv) combination of i) and ii), v) combination of i) and iii), vi) combination of ii) and iii), and vii) combination of i), ii) and iii); and/or average velocity of saccades, disconjugacy 80 ms and/or 160 ms after right saccades, number or proportion of regression saccades, and reading speed during a text reading test.

21. The method as claimed in claim 1, wherein the person is an individual suffering from vertigo, preferably vertigo with functional origin, in particular vestibular asthenopia or Meniere's disease.

22. The method according to claim 21, wherein:

in step, the person's binocular motricity is stimulated by means of a binocular motricity stimulation device configured to specifically stimulate vergences in seated and in standing position, and treating each selected trajectory comprises calculating latency and total amplitude of convergences and divergences during vergence tests performed in seated and in standing position.

\* \* \* \* \*